(12) United States Patent
Cohen et al.

(10) Patent No.: US 12,412,646 B2
(45) Date of Patent: Sep. 9, 2025

(54) HEALTHCARE INFORMATION ANALYSIS AND GRAPHICAL DISPLAY PRESENTATION SYSTEM

(71) Applicant: T6 Health Systems LLC, Chestnut Hill, MA (US)

(72) Inventors: Lewis S. Cohen, Chestnut Hill, MA (US); Larissa Roux, Vancouver (CA); Morad Hameed, Vancouver (CA); Hubert Bandurski, Oakville (CA); Igor Muravyov, Brookline, MA (US)

(73) Assignee: T6 Health Systems LLC, Chestnut Hill, MA (US)

( * ) Notice: Subject to any disclaimer, the term of this patent is extended or adjusted under 35 U.S.C. 154(b) by 0 days.

(21) Appl. No.: 17/686,316

(22) Filed: Mar. 3, 2022

(65) Prior Publication Data

US 2022/0189594 A1 Jun. 16, 2022

Related U.S. Application Data

(63) Continuation of application No. 16/833,376, filed on Mar. 27, 2020, now Pat. No. 11,282,594, which is a
(Continued)

(51) Int. Cl.
*G16H 10/60* (2018.01)
*G06F 3/0482* (2013.01)
(Continued)

(52) U.S. Cl.
CPC .......... *G16H 10/60* (2018.01); *G06F 3/0482* (2013.01); *G06F 3/04842* (2013.01); *G16H 15/00* (2018.01)

(58) Field of Classification Search
CPC ........ G16H 40/63; G16H 15/00; G16H 20/30; G16H 80/00; G16H 30/20; G16H 10/60;
(Continued)

(56) References Cited

U.S. PATENT DOCUMENTS

2002/0055855 A1* 5/2002 Cule ................ G16H 15/00
705/2
2002/0170565 A1* 11/2002 Walker .............. G16H 15/00
128/920
(Continued)

FOREIGN PATENT DOCUMENTS

WO WO-9619774 A1 * 6/1996 ........... G06F 19/325

OTHER PUBLICATIONS

A. Sarcevic, et al., "A paper-digital interface for information capture and display in time-critical medical work," 2012 6th International Conference on Pervasive Computing Technologies for Healthcare (PervasiveHealth) and Workshops, San Diego, CA, USA, 2012, pp. 17-24 (Year: 2012).*
(Continued)

*Primary Examiner* — Joseph D Burgess
(74) *Attorney, Agent, or Firm* — Nutter McClennen & Fish LLP

(57) ABSTRACT

Systems, methods, and computer-readable media for analyzing and presenting healthcare information are described. Some embodiments may include a system configured to receive healthcare information relating to a patient and to generate a patient profile. The patient profile may include a physiological status as well as a physiological assessment and a treatment assessment based on the automatic and dynamic analysis of the healthcare information. The healthcare information and the patient profile may be updated and/or accessed in real-time or substantially real-time through client logic devices in communication with the system. In this manner, a healthcare professional may enter healthcare information for a patient that is readily accessible by other healthcare professionals through the system. The system may present navigation objects that include a plurality of navigation layers selectively displayed based on
(Continued)

user input. In addition, information objects may be displayed to users based on user navigation selections.

18 Claims, 53 Drawing Sheets

Related U.S. Application Data continuation of application No. 14/800,448, filed on Jul. 15, 2015, now Pat. No. 10,636,516.

(60) Provisional application No. 62/068,518, filed on Oct. 24, 2014, provisional application No. 62/024,980, filed on Jul. 15, 2014.

(51) Int. Cl.
*G06F 3/04842* (2022.01)
*G16H 15/00* (2018.01)

(58) Field of Classification Search
CPC ....... G16H 50/50; G06F 3/0482; G06F 3/011; G06F 3/04817
See application file for complete search history.

(56) References Cited

U.S. PATENT DOCUMENTS

| | | | |
|---|---|---|---|
| 2008/0098333 A1* | 4/2008 | Champion | G16H 50/70 715/849 |
| 2010/0050110 A1* | 2/2010 | Hughes | G16Z 99/00 715/781 |
| 2012/0041330 A1* | 2/2012 | Prichep | A61B 5/30 600/544 |
| 2013/0013342 A1* | 1/2013 | Morris | G16H 10/20 705/3 |
| 2014/0081655 A1* | 3/2014 | Schoenberg | G16H 40/67 705/2 |

OTHER PUBLICATIONS

Mohyuddin, W. A. Gray, H. Bailey, C. Jordan and D. Morrey, "Wireless Patient Information Provision and Sharing at the Point of Care using a Virtual Organization Framework in Clinical Work," 2008 Sixth Annual IEEE International Conference on Pervasive Computing and Communications (PerCom), Hong Kong (Year: 2008).*

Z. Zhang et al., "The Five Ws for Information Visualization with Application to Healthcare Informatics," in IEEE Transactions on Visualization and Computer Graphics, vol. 19, No. 11, pp. 1895-1910, Nov. 2013, doi: 10.1109/TVCG.2013.89 (Year: 2013).*

* cited by examiner

| Quick Search | |
|---|---|
| Name | |
| THOMAS, Michael | Consult Other / Documenting Physician / Documenting Resuscitation Nurse / Emergency Physician • / General Surgery / Hand Surgery • / Handover Care |
| REYNOLDS, Elaine | |
| SIMMS, Robert | |
| MURAVYOV, Igor | |
| HAMEED, Norad | Orthopedics |
| KIDD, Bryan | Pediatrics |
| WELLINGTON, Alexan... | Plastics |
| DUNDE, Kathleen | Spine |
| RAYA, Lena | Surgery |
| MESSI, Chad | Vascular |
| GOGGINS, Pat | Trauma Junior |
| LUCCA, Antonio | Documenting Resuscitation Nurse, Res... |
| RAIOLA, Mark | Resuscitation Nurse |
| LEONARD, Mary | Resuscitation Nurse |
| TIMS, Maya | Resuscitation Nurse |

1504

1509

Team & Roles

Archive / Support / Team / Census / ED / New Patient

System Type: Demo
User: Demo User
Roles: RN, DP, TTL, DPN
TS: v0.212 R50.1951.105
Latest Metadata: v47

Log Out

For informational purposes only and not intended for diagnostic use.

FIG. 15E

| | Information relayed about pre-hospital findings or events |
|---|---|
| Injury kinematics | • High energy blunt torso trauma<br>• Multiple high velocity GSWs<br>• Blast injury |
| Signs indicating significant prehospital blood loss | • Significant prehospital hemodynamic instability<br>• Prehospital cardiopulmonary arrest |
| | Primary and secondary survey findings |
| Injury pattern | RUQ GSW or bullet location with a bullet retained in the same quadrant and hemodynamic instability<br>Upper quadrant abdominal GSW with a horizontal shift trajectory across the abdominal midline and hemodynamic instability<br>Entry wound in the back with a bullet in the body and hemodynamic instability<br>Partially stable or unstable (Tile B or C) pelvic fracture<br>An injury requiring adjunctive use of angioembolization to achieve hemostasis<br>Multiple injuries spanning across more than one anatomical region or body cavity that each require surgery with or without angioembolization |
| Overall injury/disease burden | Associated significant pre-existing medical comorbidities<br>High ISS (>25; 25-35; n=19)<br>Associated severe traumatic brain injury<br>Associated bilateral pulmonary contusions<br>Associated multiple long bone fractures<br>Anticipated that >60 min (60-90 min) will be required to complete definitive surgery |
| Degree of physiological insult in the ED | Significant hemodynamic instability (SBP <90 mmHg; 90-90 mmHg; n=10; And >12.5 (12.5-12.5) U of PRBCs were administered in the ED<br>And coagulopathy<br>And hypothermia, acidosis, and coagulopathy Hypothermia (T <34°C; 34-35°C; n=6)<br>Acidosis (pH <7.2; 7.2-7.2; n=6)<br>Coagulopathy (PT >19 sec or PTT >60 sec; n=1 each) T ≤35.5°C and BD >5 mmol/L<br>Hypothermia and coagulopathy<br>Hypothermia, acidosis, and coagulopathy*<br>A low Revised Trauma Score (≤5; 5-6; n=3) |
| | Amount and/or type of resuscitation provided preoperatively |
| Volume of resuscitation fluid administered | A large volume of crystalloids<br>A large volume of PRBCs (>10 U; 2-16; n=3)<br>A large volume or PRBCs and hypothermia and coagulopathy<br>A large volume of crystalloids (>2 L) and acidosis (pH <7.2) |
| A thoracotomy was performed for resuscitation of a penetrating thoracic injury with a witnessed post-injury cardiac arrest | |
| | Significant clinical deterioration after angioembolization of a major liver or spleen injury<br>Hospital facility and/or staff resources |
| | When a trauma patient presents to a rural hospital with signs of physiologic derangement<br>Civilian mass casualty incident |

STREAMLINES CLINICAL DOCUMENTATION
- simultaneously documents trauma assessment and resuscitation
- eliminates duplication of data entry
- portability

GUIDES BEST PRACTICE
- utilizes accumulating clinical data to trigger injury-specific clinical practice guidelines
- displays high priority alerts
- provides data-driven meaningful support to team members

PROMOTES COMPLETE AND SAFE CARE
- generates injury-specific smart checklists
- ensures complete care in time-challenged and complex environments
- provides time-stamped record of detailed action

ENHANCES COMMUNICATION & TEAM DYNAMICS
- displays resuscitation data
- displays clinical practice guidelines, imminent threat alerts, and checklists
- enhances cohesion and shared mental mode among trauma team

GENERATES DATA TO DRIVE PERFORMANCE
- synchronizes with electronic registries
- reports on trauma system performance and outcomes
- microcosts clinical processes to link value and quality of trauma care

CONTRIBUTES TO RESEARCH AND PUBLIC HEALTH
- adaptable data fields allow for innovative clinical trauma research
- identifies opportunities for high risk and population based injury prevention

FIG. 25

HEALTHCARE INFORMATION ANALYSIS AND GRAPHICAL DISPLAY PRESENTATION SYSTEM

CROSS REFERENCE TO RELATED APPLICATIONS

This application claims priority as a continuation application to U.S. patent application Ser. No. 16/833,376 filed on Mar. 27, 2020, which claims priority as a continuation application to U.S. patent application Ser. No. 14/800,448 filed on Jul. 15, 2015, which claims the benefit of U.S. Provisional Application Nos. 62/024,980 filed on Jul. 15, 2014 and 62/068,518 filed on Oct. 24, 2014, the contents of which are incorporated by reference in their entirety as if fully set forth herein.

BACKGROUND

Advances in policies, assessment, and assurance aspects of injury prevention, pre-hospital care, acute care, and rehabilitation services have been driven by the systematic collection and analysis of injury data in mandated trauma registries. As front line providers of clinical care, trauma care professionals have ready access to and a profound understanding of such injury data. As such, trauma care professionals have a substantial role in the interpretation of these data to policy makers, the design and advocacy of injury control strategies, and the ultimate development of injury control policy.

Nowhere is comprehensive, data-driven care more important than in the first six hours after injury or an acute illness (for example, stroke, acute coronary syndromes and severe sepsis). The outcome of a trauma or an acute illness is critically dependent on the provision of timely, evidence-based and complete care, for example, before hemorrhage and other forms of shock cause potentially irreversible organ injury or death. Such care often requires seamless coordination across disciplines and between multiple healthcare entities in order to focus the highest standards of care and the rapid and efficient deployment of resources in times of great crisis.

Although trauma systems have made great strides in pre-hospital care and in the creation of highly functional trauma teams and trauma centers, there are still profound gaps in patients' access to uniformly high quality injury care and there are still great opportunities to improve safety and efficiency in the complex environment of acute trauma care. For instance, data generated at the point-of-care that could be used to inform complex decision-making or to improve health system performance is often not collected, lost, or not analyzed due to constraints in time or analytic power, and the chaotic environment of initial care. In addition, new developments in the understanding of the principles and practice of trauma care are often not accessible in a timely manner and are therefore not applied in circumstances when they might prevent a complication or save a life. Accordingly, patients would benefit from a system capable of collecting, analyzing, and presenting data generated at the point-of-care through timely and accurate techniques.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a healthcare information presentation system may include a client computing device comprising a processor and a non-transitory, computer-readable storage medium in operable communication with the processor. The computer-readable storage medium may include one or more programming instructions that, when executed, cause the processor to receive healthcare information from a server computing device in communication with the client computing device, present a navigation object on a display device in operable communication with the processor, the navigation object comprising a plurality of navigation levels including a primary navigation level and a secondary navigation level, each of the primary navigation level and the secondary navigation level comprising at least one selection area, receive a primary selection of a primary selection area of the primary navigation level, present at least one secondary selection area of the secondary navigation level based on the primary selection; receive a secondary selection of the at least one secondary selection area, and present at least one healthcare information object on the display device based on the secondary selection.

In an embodiment, a computer-implemented method for presenting healthcare information may include, by a processor of a client computing device, receiving healthcare information from a server computing device in communication with the client computing device, presenting a navigation object on a display device of the client computing device, the navigation object comprising a plurality of navigation levels including a primary navigation level and a secondary navigation level, receiving a primary selection of a primary selection area of the primary navigation level, presenting at least one secondary selection area of the secondary navigation level based on the primary selection, receiving a secondary selection of the at least one secondary selection area, and presenting at least one healthcare information object on the display device based on the secondary selection.

In one aspect, the primary navigation level and the secondary navigation level may be configured as concentric circles. In another aspect, the at least one healthcare information object may include a clinical practice guideline. In a further aspect, the at least one primary selection area may include at least two of an archive selection area, a support selection area, a team and roles selection area, a census selection area, an emergency department selection area, and a new patient selection area. In one aspect, the navigation object may be configured for a trauma event and the at least one primary selection area comprises at least two of a start selection area, a primary selection area, a secondary selection area, a flow sheet selection area, a review selection area, and a transfer selection area. In another aspect, the secondary selection area may be configured to access patient information for a trauma event and may include an arrival secondary selection area and a treatments on scene secondary selection area In an embodiment, a healthcare information analysis system may include a processor and a non-transitory, computer-readable storage medium in operable communication with the processor. The computer-readable storage medium may contain one or more programming instructions that, when executed, cause the processor to receive point-of-care healthcare information associated with a patient in substantially real-time collected via at least one of a plurality of mobile computing devices; analyze the healthcare information to generate a patient profile of the patient, the patient profile comprising a physiological status, a physiological assessment, and a treatment assessment, and generate at least one graphical user interface element associated with the patient profile for presentation at a plurality of display devices.

In one aspect, the plurality of display devices may include a monitor device, such as an overhead monitor device. In one aspect, the healthcare information may include at least one of surgeries, symptoms, type of injury, severity of injury, mechanism of trauma, and trauma location. In an embodiment, the system may be configured to be used for trauma healthcare services and/or surgical healthcare services. In an embodiment, the plurality of mobile computing devices comprise a smartphone and a tablet computing device. In one aspect, the healthcare information comprises user input and device input. In one aspect, the graphical user interface element comprises a dashboard, such as a dashboard configured to receive health information user input through at least one field. In one aspect, the dashboard is configured to present a graphical representation of a body of the patient for indicating an injury to the patient.

In an embodiment, a computer-implemented method for analyzing and presenting health information may include, by a processor, receiving point-of-care healthcare information associated with a patient in substantially real-time collected via at least one of a plurality of mobile computing devices, analyzing the healthcare information to generate a patient profile of the patient, the patient profile comprising a physiological status, a physiological assessment, and a treatment assessment, and generating at least one graphical user interface element associated with the patient profile for presentation at a plurality of display devices.

In an embodiment, a computer-readable storage medium having computer-readable program code configured to generate at least one healthcare assessment embodied therewith may include computer-readable program code configured to receive point-of-care healthcare information associated with a patient in substantially real-time collected via at least one of a plurality of mobile computing devices, computer-readable program code configured to analyze the healthcare information to generate a patient profile of the patient, the patient profile comprising a physiological status, a physiological assessment, and a treatment assessment, and computer-readable program code configured to generate at least one graphical user interface element associated with the patient profile for presentation at a plurality of display devices.

In an embodiment, a graphical user interface for use in a healthcare environment to assist with treating patients may include a plurality of primary graphical objects, each of the plurality of primary graphical objects being associated with information regarding a patient, and a plurality of secondary graphical objects associated with the primary graphical objects such that selection of a primary graphical object effects presentation of at least one of the plurality of secondary graphical objects. In one aspect, the primary graphical objects may include a primary navigation level and the secondary graphical objects comprise a secondary navigation level. In another aspect, the primary graphical objects may be presented as an inner circle and the secondary graphical objects may be presented as an outer circle relative to the inner circle. In a further aspect, the graphical user interface may be configured for a trauma event and the plurality of primary graphical objects may include at least two of a start selection area, a primary selection area, a secondary selection area, a flow sheet selection area, a review selection area, and a transfer selection area.

BRIEF DESCRIPTION OF THE DRAWINGS

The above and other objects of the present invention will become more readily apparent from the following detailed description taken in connection with the accompanying drawings.

FIG. 10 depicts an illustrative trauma system dashboard according to a fourth embodiment.

FIGS. 11B and 11C depict an illustrative template configured directed toward airway assessment according to some embodiments.

FIGS. 11D and 11E depict an illustrative template directed toward trauma investigation according to some embodiments.

FIGS. 15A-15F depict various illustrative screens included in the health information application according to some embodiments.

FIG. 18B depicts illustrative key patient indicators according to some embodiments.

FIGS. 20A-20B depict an illustrative screen according to some embodiments for viewing and/or adding vitals and other patient information.

FIG. 25 depicts illustrative and non-limiting examples of technological advantages of a healthcare embodiment of the system.

DETAILED DESCRIPTION

Figure 1:
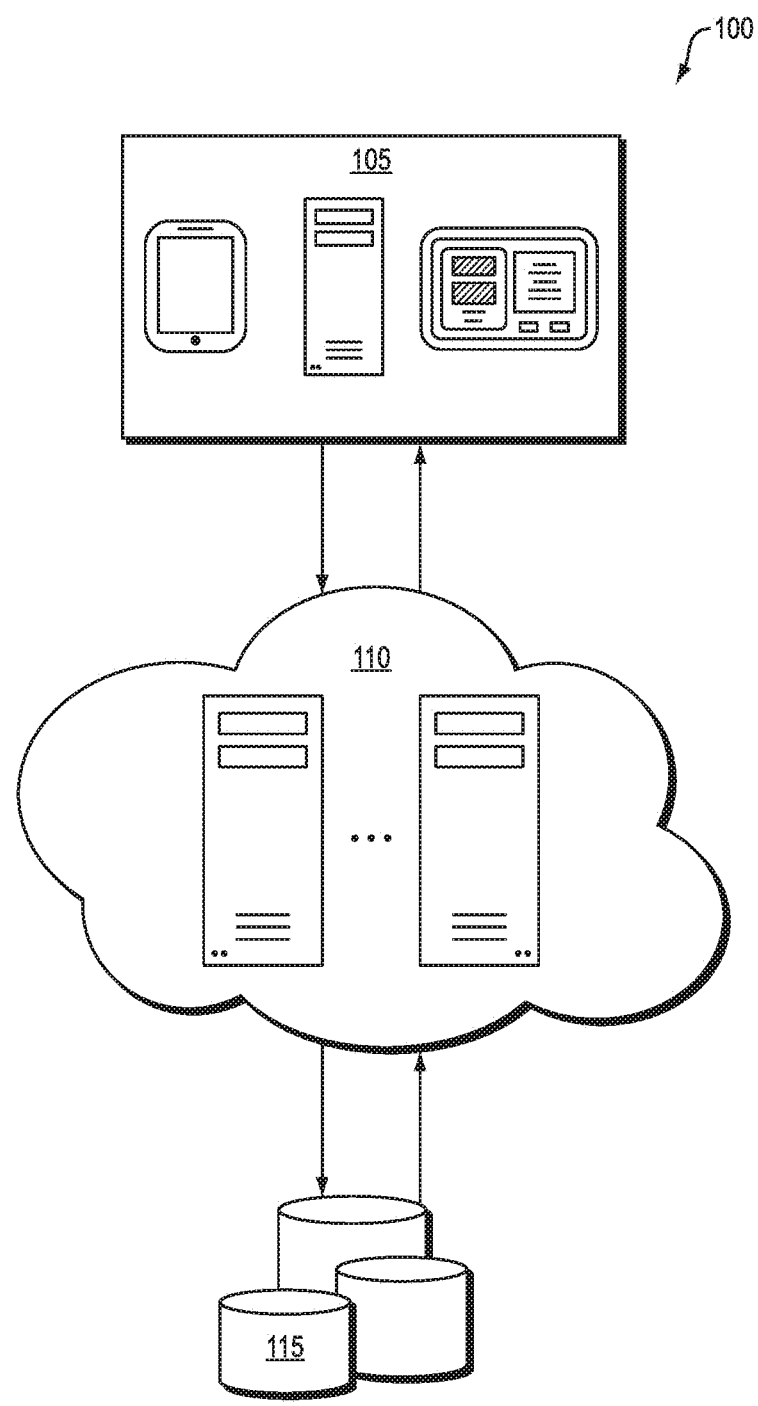
FIG. 1 depicts an illustrative healthcare information analysis and presentation system according to a first embodiment

The present disclosure generally relates to systems, methods and non-transitory computer-readable media for collecting and analyzing healthcare information and generating and presenting healthcare assessments in real-time or substantially real-time. In particular, some embodiments provide a healthcare information analysis and presentation system (the "system") that is configured to analyze, examine, search, investigate, consider, evaluate, and/or otherwise process healthcare information and to generate various physiological assessments and treatment assessments based on the healthcare information. In some embodiments, the system can generate graphical user interface (GUI) elements configured to present healthcare information, physiological assessments, and/or treatment assessments on a display device, such as a display device of a mobile computing device or display monitor in a manner that allows medical professionals to efficiently, effectively, and accurately provide healthcare to patients in a manner not available using conventional processes and technology.

Healthcare information may generally include information associated with a patient receiving treatment through a healthcare entity. Non-limiting examples of healthcare information may include, without limitation, age, gender, weight, height, medications, surgeries and other medical procedures (for example, diagnostic tests, diagnostic imaging tests, or the like), occupation, past and current medical conditions, family history, patient description of health condition, healthcare professional description of health condition, symptoms, type of injury, severity of injury, mechanism of trauma, trauma location, healthcare professionals providing or assigned to provide care, or the like. A healthcare entity may generally include any entity capable of providing healthcare to a patient, including a hospital, a medical clinic, an outpatient facility, a doctor's office, a surgical center, a diagnostic facility, a medical specialist, an ambulance, an emergency room, a medical trauma team, a surgical team, or the like.

In some embodiments, a patient profile of a patient generally includes information associated with the real-time or substantially real-time health status of a patient, for example, at the point-of-care by a healthcare entity. A patient profile may include information associated with physiological characteristics and treatment information of the patient. Illustrative and non-restrictive examples of information included in a patient profile may include patient physical characteristics and logistical information (e.g., height, weight, age, address, etc.), injuries, admission time, procedures performed and/or scheduled to be performed on the patient, diagnostic tests performed and/or scheduled to be performed on the patient, medical conditions, allergies, pregnancy status, patient medical status (e.g., "in shock," hypothermic, conscious/unconscious, responsive, etc.).

A physiological assessment may generally include any valuation, appraisal, evaluation, estimation, ranking, diagnosis, prognosis, and/or other calculation configured to indicate the physiological status of the patient based on the patient profile. For example, a physiological assessment may be generated indicating that a patient is likely experiencing a difficult airway condition based on information in the patient profile.

A treatment assessment may generally include any valuation, appraisal, evaluation, estimation, ranking, and/or other calculation configured to determine a course of treatment for the patient based on the patient profile and the physiological assessment. Non-limiting examples of treatment assessments may include diagnostic testing, surgical procedures, medication, and any other type of treatment regimen for addressing medical issues indicated by the patient profile and/or the physiological assessment.

The system configured according to some embodiments described herein provides multiple technological advantages and technical features. One non-limiting technological advantage and technical feature is the efficient capture of medical and patient data within standard processes of care, which may be analyzed in real-time or substantially real-time to provide effective and efficient point-of-care decision-making. Another non-limiting technological advantage and technical feature is the ability for all healthcare professionals involved in the assessment and/or treatment of a patient to document and retrieve medical and patient information in real-time or substantially real-time at the point-of-care on separate computing devices and/or display devices. For example, a trauma nurse may update patient information from a mobile computing device in an emergency room and the updated patient information may be immediately available for access by a member of an operating team in the process of receiving the patient for surgery.

A further technological advantage and technical feature is the ability to provide healthcare professionals with medical assessments and/or treatment determinations in real-time or substantially real-time at the point-of-care based on an analysis of information in the patient profile. For instance, the system may analyze the physiological information of a patient in view of historical medical data to determine a physiological status of the patient (e.g., cardiac arrest) and potential treatment regimens (e.g., medications, medical procedures). In this manner, the system is able to provide more effective and efficient medical evaluations and treatment recommendations to medical professionals compared to those available using existing processes and technologies (see FIG. 25 for illustrative and non-limiting examples of technological advantages of a healthcare embodiment of the system)

The system provides multiple technological advances over and provides multiple technical features not present in traditional paper-based systems, conventional computer-based systems, and/or hybrid paper- and computer-based systems. Paper-based systems, such as conventional clinical charting techniques, are not capable of providing a user interface for interactive access to healthcare information, processes, or the like. In particular, traditional paper-based healthcare information systems rely on patient files with collections of charts and past medical records. Such patient files are not capable of being automatically or dynamically updated and do not provide access to a patient's complete medical history. Accordingly, healthcare professionals are not capable of accessing all of the information necessary to efficiently make accurate and reliable medical assessments using such paper-based medical files. In addition, healthcare professionals are not able to efficiently access the information that they need, as obtaining information requires physically searching through multiple documents, charts, and other files. Conventional computer-based systems suffer from much of the same deficiencies as paper-based systems, except that the healthcare provider is interacting with a computer screen instead of a paper file.

Although a computer is able to locate and process information much faster, such conventional computer-based systems are not configured to present the information in an efficient, meaningful way that assists healthcare professionals with making faster and more accurate decisions for patient care. Conventional computer-based systems require healthcare professionals to go through myriad tedious drop-down selections, pages, and search queries in order to access information. Conventional computer-based systems are able to present information faster, however, they are not able to present meaningful information that assists healthcare professionals with efficiently sharing information and making quick and accurate decisions.

In contrast, the methods and systems described according to some embodiments reduce the time and cognitive effort required for healthcare professionals to access, quantify, and assess healthcare information. For example, an emergency room physician is better able to make efficient and accurate decisions about treatment options for a trauma patient using the methods and systems described according to some embodiments in comparison to conventional healthcare information techniques. In addition, the methods and systems described according to some embodiments assist healthcare professionals with effectively and dynamically sharing information, for example, between departments, healthcare facilities, or the like in a meaningful way that leads to faster and better healthcare decision making. For example, methods and systems described according to some embodiments would allow a trauma surgeon preparing to operate on a car accident victim to quickly and intuitively access the accident and on-site treatment information with one GUI selection and then to access the diagnostic imaging results with a second GUI selection without having to search through multiple documents or pages and/or to ask a colleague for the information, as would be required using a conventional healthcare information system. In another example, clinicians at the point of care may have access to patient-specific, evidence based practice guidelines and checklists. In a further example, trauma teams can review an overhead GUI interface to check on key physiological data and essential tasks during the course of treatment and resuscitation. In this manner, the system may streamline non-verbal communication by effectively displaying healthcare information, clinical practice guidelines, alerts, key patient indicators, process checklists, or the like. Such shared overhead or computing device graphical user interface projects may operate, among other things, to promote team cohesion and a shared mental mode among a disparate team of healthcare professionals treating a patient.

A system according to the present teachings may be configured to transform healthcare information into a format that is easily accessible to medical professionals. For instance, the system may be configured to transform healthcare information into medical assessments and into objects, object values, and/or characteristics of objects displayed on a graphical user interface. In some embodiments, the system may be configured to transform information into color schemes configured to indicate process steps, stabilization of a patient, or the like. In this manner, information may be transformed into graphical interface objects and/or characteristics thereof that may be used to allow medical professionals to more efficiently, effectively, and accurately provide patient care, especially in time-sensitive trauma situations, than is possible using conventional techniques and processes.

The system presents novel software tools and user interfaces that solve technical problems relating to providing medical care to patients, particularly in the real-time environment of trauma care. A non-limiting example of a technical problem that is solved by the system is providing efficient and effective access to all of the information necessary to treat a patient from a single point of access. Using conventional technology, such information is located in disparate locations, including paper charts and separate databases (e.g., vitals, demographic information, trauma event information, or the like). Thus, the use of such conventional technology can result in consuming valuable time to obtain the necessary information for treating a patient. For example, a physician in an emergency room may have to consult a paper chart or an electronic chart accessible through a computing device to obtain information concerning how the patient's injuries occurred. The treating physician may then have to consult another source to determine the patient's current vitals and yet another source to locate what medications and/or fluids, if any, the patient has received. The treating physician may then have to also consult with another source to determine which diagnostic tests have been completed and the results thereof. During this time, the treating physician may not have access to accurate information regarding how much time has elapsed since the trauma event or where the patient is in the treatment process.

A system according to various embodiments of the present teachings solves these technical problems, as well as multiple others, by centralizing the information relating to the patient and any treatment thereof and presenting this information to medical professionals in a user friendly and efficient manner. The system also provides readily accessible timing information concerning the trauma event and/or treatment and where the patient is in the treatment process from a central access point. The system also solves the technical problem of allowing a user to efficiently navigate in an intuitive way through all of the information available within the system. As described below, patient information and treatment processes are accessible through easy-to-use, intuitive, and effective navigation tools and information presentation interfaces. In this manner, medical professionals are able to more completely, accurately, and efficiently access information required to treat patients. As such, the systems according to the present teachings provide a technological advantage over current techniques and technology.

For example, in a trauma care setting, the system may be configured to: streamline the collection of clinical data at the point of care during trauma resuscitation and other acute clinical contexts to support relevant and complete documentation; link point-of-care data to other clinical data sources and resources for best practices; provide real-time data analytics to support clinical decision-making; enhance the communication of multidisciplinary health care teams; and create, in real-time, deep data sets to inform safety, performance improvement, and research.

As is well known in the art, the first 6 hours after severe injury or after the onset of other critical illnesses is a time period, where collection of data regarding the injury and making a decision how to treat the patient based on the collected data is of critical importance. The system may be configured for collection of standardized, high-resolution data by both physicians and nurses and to collect both point data from initial trauma surveys as well as minute-to-minute longitudinal data that can be used to display physiological trends. The system may be configured for the real-time analysis of both single point-in-time assessments and longitudinal data to provide more efficient and effective clinical assessments and to identify physiologic instability earlier during the course of illness. The system may include data warehouses and a big data analytics strategy that may provide regular and customized reports on quality of care and outcomes. The system may generate and maintain a deep data set, with significantly greater volume and detail than conventional trauma registries. As a result, the system can identify new predictive scores and previously unrecognized opportunities to improve patient safety and quality of care.

FIG. 1 depicts an illustrative healthcare information analysis and presentation system according to a first embodiment. As shown in FIG. 1, the healthcare information analysis and presentation system (the "system") 100 may include one or more server logic devices 110 (or server computing devices), which may generally include a processor, a non-transitory memory or other storage device for housing programming instructions, data or information regarding one or more applications, and other hardware, including, for example, the central processing unit (CPU) 2505, read only memory (ROM) 2510, random access memory (RAM) 2515, communication ports 2540, controller 2520, and/or memory device 2525 depicted in FIG. 25 and described below in reference thereto.

In some embodiments, the programming instructions may include a healthcare information analysis and presentation application (the "healthcare information application") configured to, among other things, receive and analyze healthcare information and generate patient profiles and graphical user interface (GUI) elements associated with the patient profiles. The healthcare information application may be configured to receive, process, analyze, present, control, or otherwise manage healthcare information for various healthcare services, conditions, facilities, specialties, entities, providers, or the like. Although emergency room or "trauma" healthcare services are used as an example herein, embodiments are not so limited, as the system and healthcare information application may be used in connection with any healthcare services or facilities capable of operating according to some embodiments, including, without limitation, hospitals, outpatient facilities, surgical facilities (including emergency general surgery (EGS)), doctor's offices, medical specialists offices, diagnostic imaging centers, oncologist facilities, dental offices, nursing homes, or the like.

The server logic devices 110 may be in operable communication with client logic devices 105 (or client computing devices), including, but not limited to, mobile computing devices, such as laptop computers, smartphones, personal digital assistants (PDAs), tablet computing devices, mobile medical equipment, wearable measurement devices, or any other mobile computing device now known or developed in the future. In some embodiments, the client logic devices may also include server computing devices, personal computers (PCs), kiosk computing devices, medical equipment, televisions, display monitors. The client logic devices 105 and the server logic devices 110 may communicate within the system using various communication and data transfer protocols, such as any of the various protocols known to those having ordinary skill in the art. Non-limiting examples of such protocols include Bluetooth, hypertext transfer protocol (HTTP), Ethernet, WiFi, Health Level 7 International (HL7), cellular communication protocols (e.g., 3G, 4G, LTE, etc.).

In some embodiments, the healthcare information application may be accessible through various platforms, such as a client application, web-based application, over the Internet, and/or a mobile application (for example, a "mobile app" or "app"). According to some embodiments, the healthcare information application may be configured to operate on each client logic device 105 and/or to operate on a server computing device accessible to logic devices over a network, such as the Internet. All or some of the files, data and/or processes used for analysis of healthcare information and/or the generation of patient profiles and associated GUI elements may be stored locally on each client logic device 105 and/or stored in a central location and accessible over a network.

In some embodiments, one or more data stores 115 may be accessible by the client logic devices 105 and/or server logic devices 110. The data stores 115 may include healthcare information, healthcare assessment processes, historical information, and/or the like. Non-limiting examples of data stores 115 may include healthcare information and management systems (HIMS), electronic medical record (EMR) systems, radiology information systems (RIS), picture archiving and communications system (PACS), medical registries, the National Trauma Data Bank (NTDB) (United States), the National Trauma Registry (NTR) (Canada), medical information repositories, or the like.

Although the one or more data stores 115 are depicted as being separate from the logic devices 105, 110, embodiments are not so limited, as all or some of the one or more data stores may be stored in one or more of the logic devices.

A healthcare professional may enter healthcare information (e.g., "clinical data" or "data") into the system 100 using the healthcare information application through a client logic device 105. The healthcare information may be entered at the point-of-care, for example, in an ambulance transporting the patient to a healthcare facility, in the emergency room of a hospital, or within a patient examination room of a private medical practice. The healthcare information may be available through the client logic devices 105 in real-time or substantially real time after being entered into the system 100. For instance, the healthcare information application may analyze healthcare information entered by a first medical professional using a first client logic device 105 and generate a medical diagnosis and a treatment assessment that is stored in a storage device within the system 100. A second medical professional may access the healthcare information, medical diagnosis, and/or treatment assessment using a second client logic device 105 in real-time or substantially real time after the healthcare information has been entered into the system 100 by the first medical professional.

Figure 2:
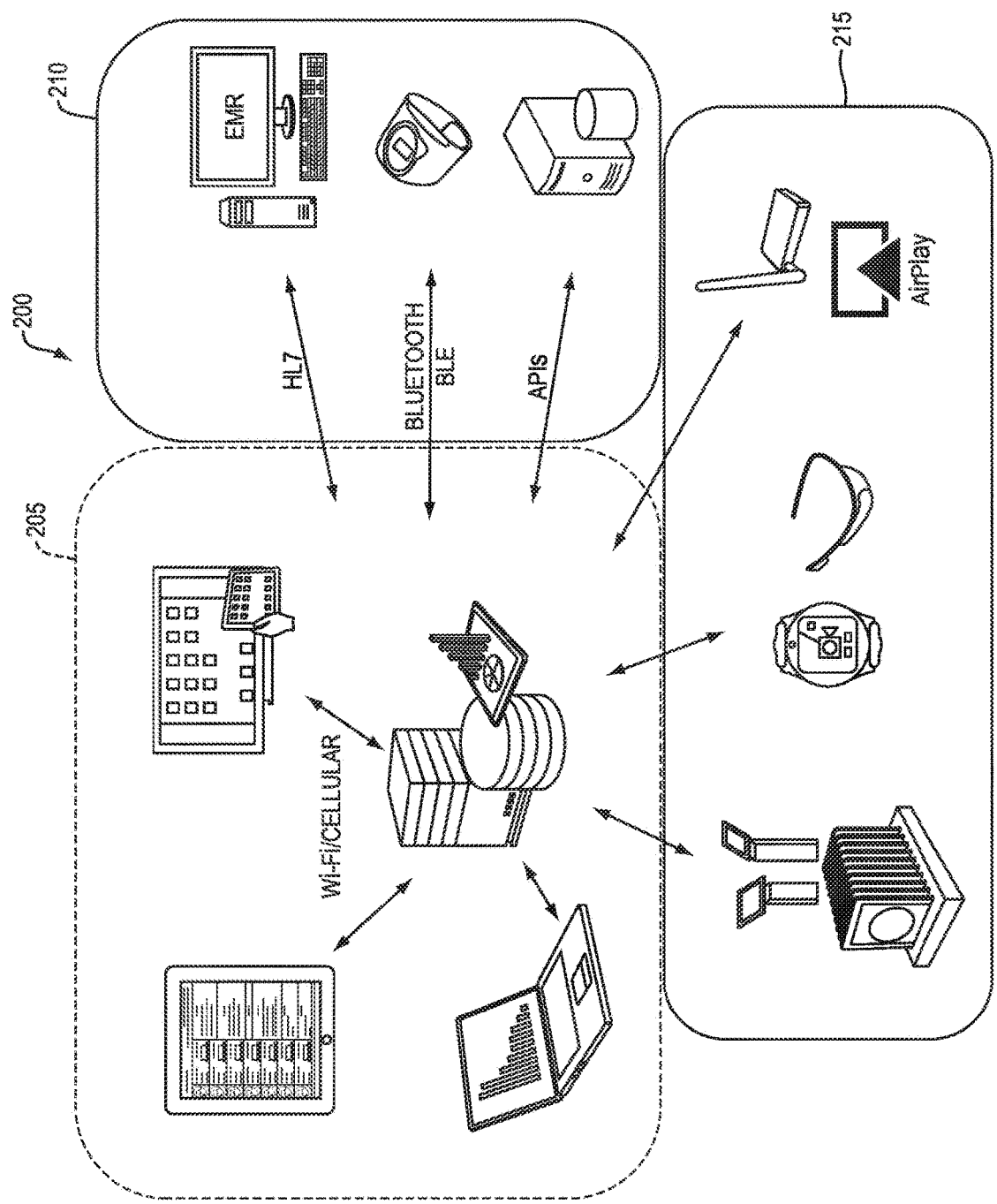
FIG. 2 depicts a schematic diagram of a system according to some embodiments.

FIG. 2 depicts a schematic diagram of a system according to some embodiments. As shown in FIG. 2, a system 200 may include various core system components 205. In some embodiments, the core system components 205 may include servers (e.g. servers 110 depicted in FIG. 1) and data storage devices configured to execute the healthcare information application and to receive and store healthcare information. The core system components 205 may also include client computing devices (e.g., client logic devices 105 depicted in FIG. 1) configured to execute or access the healthcare information application. The client computing devices may be configured to enter health information into the system 200 through the healthcare information application. For instance, a client computing device may be a tablet computing device (e.g., iPad® manufactured by Apple Inc. of Cupertino, California, United States) executing a client version of the healthcare information application configured to present a data entry interface on a display component of the tablet computing device. A user may enter healthcare information using the data entry interface. In another instance, a user may access a healthcare information presentation interface generated by the healthcare information application to access and view healthcare information associated with one or more patients.

The core components 205 may be in communication with healthcare entity computing systems 210, such as a HIMS, an EMR system, medical devices and equipment, and computing devices. In some embodiments, at least a portion of the core components 205 may be configured to transmit/receive data (i.e., healthcare information) to/from the healthcare entity computing systems 210 through various protocols (e.g., Bluetooth, HTTP, Ethernet, WiFi, HL7, etc.) and interfaces (e.g., application programming interfaces (APIs)). For instance, a core component 205 server may receive healthcare information from a healthcare entity computing systems 210 medical device or server in communication with a medical device. In one example, a hospital may use a blood pressure monitor configured to wirelessly communicate patient blood pressure readings to a server computing device of a central healthcare entity computing system 210. The blood pressure readings may be transmitted as healthcare information to the core components 205. In another example, a server computing device of the core components 205 may poll healthcare entity computing systems 210 seeking updated information for storage in a storage device of the core components 205.

The core components 205 may be in communication with various peripheral devices 215, such as communication devices (e.g., hubs, routers, etc.), mobile computing devices, wearable or personal measurement devices (e.g., devices or sensors configured to measure various physiological characteristics of a user, such as heart rate, oxygen levels, temperature, etc.). The peripheral devices 215 may be configured to receive, generate, and/or transmit healthcare information to the core components 205. For instance, a peripheral device 215 may be configured as a wearable heart rate monitor that may transmit heart rate information about a user to the core components 205, such as a server computing device configured to store the heart rate information in a digital patient record.

Figure 3:
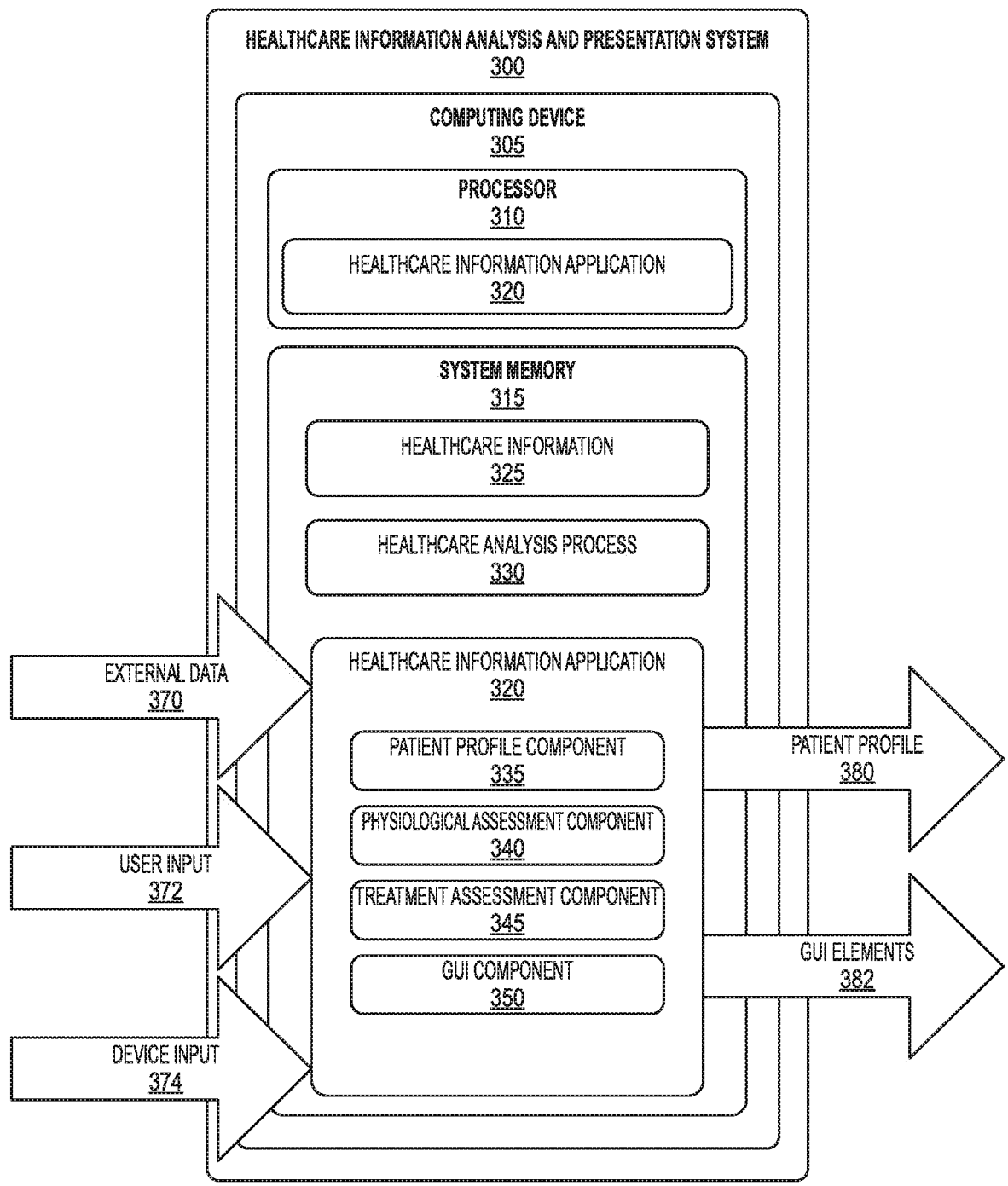
FIG. 3 depicts an illustrative healthcare information analysis and presentation system according to some embodiments.

FIG. 3 depicts an illustrative healthcare information analysis and presentation system according to some embodiments. As shown in FIG. 3, a healthcare information analysis and presentation system (or system) 300 may include a computing device 305 having a processor 310 and system memory 315. The computing device 205 may include any type of computing device, such as the client logic device 105 and server logic devices 110 described in reference to FIG. 1. The processor 310 may be configured to execute a healthcare information application 320. The healthcare information application 320 may be configured to receive external data 370, user input 372, and/or device input 374, for instance, through the processor 310 and/or as stored or cached as local healthcare information 325 in the system memory 315.

The external data 370 may include information from any data source accessible by the system 300, including, without limitation a healthcare entity computing system, a HIMS, an EMR system, a RIS, a PACS, the NTDB, the NTR, and/or any other type of data store having healthcare information, a health information library and/or cloud, a third-party database, or the like.

In some embodiments, the external information 220 may include any information associated with a patient, treatment, or a diagnostic test, including, without limitation, any information associated with the physical and/or mental condition of a patient, symptoms, medical history, medications, family history, diseases, illnesses, conditions, surgeries, medical procedures, medical diagnostic tests, vital signs, lab results, associated healthcare providers, demographic information, allergies, responses to treatment, responses to medication, health insurance information, medical claims, medical costs, diagnostic processes, healthcare protocols, or the like.

The user input 372 may include data, such as healthcare information, entered into the system 300 by a user. For example, user input 372 may be provided by a user through a GUI interface of the healthcare information application 320 presented on a display component of a client logic device. The user input 372 may be received by the healthcare information application 320 and stored as healthcare information 325.

The device input 374 may include input generated by a device, such as medical devices or equipment (e.g., blood pressure device, heart rate sensor, body weight scale, thermometer, etc.), a peripheral device (e.g., a wearable measurement device or sensor), or the like. In some embodiments, a device configured to generate device input 374 may be in communication with the system 300 and/or the computing device 305, streaming the device input 374 in real-time or substantially real-time.

The healthcare information application 320 may include various modules, programs, applications, routines, functions, processes, or the like ("components") to perform functions according to some embodiments described herein. In some embodiments, the healthcare information application 320 may include a patient profile component 335, a physiological assessment component 340, a treatment assessment component 345, and/or a GUI component 350.

In some embodiments, the components 335-350 may be configured to access and/or receive the external data 370, user input 372, device input 374, healthcare information 325, and/or healthcare analysis process 330 as described according to some embodiments herein.

The patient profile component 335 may be configured to generate a patient profile 380 using, among other things, the healthcare information 325. The patient profile 380 may include admission information for the patient, such as time of admission, reason(s) for admission, treating facility, initial evaluation information, initial diagnosis, initial course of treatment, or the like. The patient profile 380 may also include demographic and medical history information concerning a patient, including, without limitation, age, height, weight, name, address, occupation, gender, medical conditions (e.g., diabetic, HIV+, allergies), pregnancy status, or the like. The patient profile 380 may include admission information for the patient, such as time of admission, reason(s) for admission, treating facility, initial evaluation information, initial diagnosis, initial course of treatment, or the like.

The patient profile 380 may include a physiological status, a physiological assessment, and/or a treatment assessment associated with a patient. The physiological status may include the physical condition (e.g., "patient vitals") of a patient based on the health information. The physiological status may be formed from various physiological elements or fields configured to provide information about the physical condition of a patient. For example, the physiological fields may include the temperature, blood pressure, heart rate, responsiveness, and/or the like. In another example, the physiological fields may include one or more injuries associated with the patient (e.g., laceration on face, burn on 45% of torso, tenderness on forearm, etc.) and the source or mechanism of the injuries (e.g., automobile accident, fall, etc.).

The physiological assessment may include diagnoses of the patient by a healthcare professional and/or the generation of a diagnosis automatically and dynamically through the physiological assessment component 340 of the healthcare information application 320. Illustrative physiological assessments may include, without limitation, a prognosis (e.g., predictive and prognosis scores), severity of injury scores (e.g., ISS), severity of illness scores (e.g., APACHE), transfusion requirements (e.g., ABC and TASH scores), clinical practice guidelines (CPGs), injury determination (e.g., burn, laceration, etc.), and/or a determination that a patient is experiencing shock, hypothermia, an allergic reaction, a difficult airway condition, cardiac arrest, or the like.

In some embodiments, the physiological assessment component 340 may be configured to perform analytics on or to otherwise analyze the healthcare information 325 using the healthcare analysis process 330 to generate a physiological assessment. In some embodiments, the healthcare analysis process 330 may include rules, algorithms, processes, and other analytical mechanisms configured to diagnose a patient based on the patient profile 380 and/or external data in real-time or substantially real-time. For example, a patient may be admitted into a hospital emergency room and a healthcare professional may provide user input 372 to the healthcare information application 320 concerning the patient physical condition, injuries, or the like. Device input 374 may also be received by the healthcare information application 320 through medical devices and equipment configured to measure the patient's physical condition (e.g., "patient vitals"). The healthcare information application 320 may store the user input 372 and device input 374 as healthcare information. The patient profile component 335 may generate a patient profile 380 from the healthcare information. The physiological assessment component 340 may analyze the patient profile 380 using the healthcare analysis process 330, including, without limitation, diagnostic algorithms (e.g., difficult airway algorithms, blunt force trauma algorithms, cardiac trauma algorithms), comparisons with historical data obtained through external data 370 (e.g., compare patient profile with healthcare information of other patients), injury prediction scores, prognostic scores, or the like. The physiological assessment component 340 may analyze the patient profile 380 to generate trends associated with the healthcare information.

The treatment assessment may include a treatment and/or diagnostic regimen or plan for the patient by a healthcare professional and/or automatically and dynamically through the treatment assessment component 345 of the healthcare information application 320. For instance, the healthcare information application 320, through the treatment assessment component 345, may determine a treatment regimen for a diagnosed medical condition of the patient based on the patient profile. In some embodiments, the treatment assessment component 345 may be configured to perform analytics on or otherwise analyze the patient profile 380 using the healthcare analysis process 380 to generate a treatment assessment or plan for the patient. The healthcare analysis process 380 may include various processes, algorithms, decision trees, or the like to determine a course of treatment for a patient based on their physical condition and the diagnoses included in their physiological assessment. For example, the treatment assessment component 345 may determine that a patient requires a certain diagnosis test to determine the cause of a physical condition (e.g., abdominal pain), requires a massive blood transfusion, or is a candidate for a particular procedure (e.g., appendectomy).

The GUI component 350 may be configured to provide GUI elements 382 that are graphical user interface elements and/or objects that can facilitate the entry of healthcare information 325 and can present to a user graphical representations of the patient profile 380 and any associated healthcare information, diagnosis, or treatment plan. The healthcare information application 320 may be configured to present the GUI elements 382 on a display component of a client computing device communicating with the system 300. For example, a GUI element 382 may include a data entry interface for entering healthcare information associated with a patient, such as the patient's demographic and admissions information. In another example, a GUI element 382 may include a graphical representation of the progress of a patient through treatment, such as a trauma assessment and/or a surgical procedure. In a further example, a GUI element 382 may include a graphical representation of a patient's body with graphical indicators of medical conditions associated therewith. In a still further example, a GUI element 382 may include a patient dashboard displayed on a display device (e.g., television monitor, display monitor, etc.) in the healthcare facility, such as in an operating room, nurses' station, or waiting room. In some embodiments, a GUI element 382 may include a navigation object, for example, including a plurality of navigation levels.

In some embodiments, the GUI component 350 may be configured to present a graphical representation of the body of the patient, for example, with indicators of injury, treatments, or the like arranged thereon. In some embodiments, the GUI component 350 may be configured to present the graphical representation of the body of the patient or portions thereof (e.g., an arm, a leg, etc.) responsive to the healthcare information application 320 receiving certain healthcare information. For example, the GUI component 350 may present an image of an arm responsive to healthcare information indicating injury to the arm such that a user may indicate and/or provide further information using a graphical representation of the body part. In this manner, a user of the system 300, such as a healthcare professional, may interface with the system 300 using GUI interfaces and objects (e.g., data entry fields) to access and provide healthcare information. In some embodiments, the GUI component 350 may be configured to manage navigation of GUI screens and objects and to present GUI objects based on device input 374, for example, such as presenting a particular secondary navigation level of a navigation object based on selection of an area on a primary navigation level.

The system 300 may be configured as a mobile-device based platform designed for use by front line clinicians for the collection of data when providing healthcare services to patients. A non-limiting example of healthcare services include trauma assessment and resuscitation. In a trauma configuration, the system 300 may include modules that span trauma resuscitation in the first 6 hours (including nursing and physician documentation), the initial operation, the tertiary survey at 24 hours (a comprehensive assessment and final documentation of injuries), and the discharge summary (a module which summarizes a patient's course in hospital including complications and other outcomes). These key points of data capture characterize the main events in a trauma patient's treatment and recovery. The vast majority of data entered into the system 300 may be defined and standardized for ready integration into local and national trauma registries. Injury and other diagnostic fields, and key interventions may also be coded according applicable conventions, such as the Injury Severity Score (ISS) and the International Classification of Diseases (ICD) systems.

Figure 4:
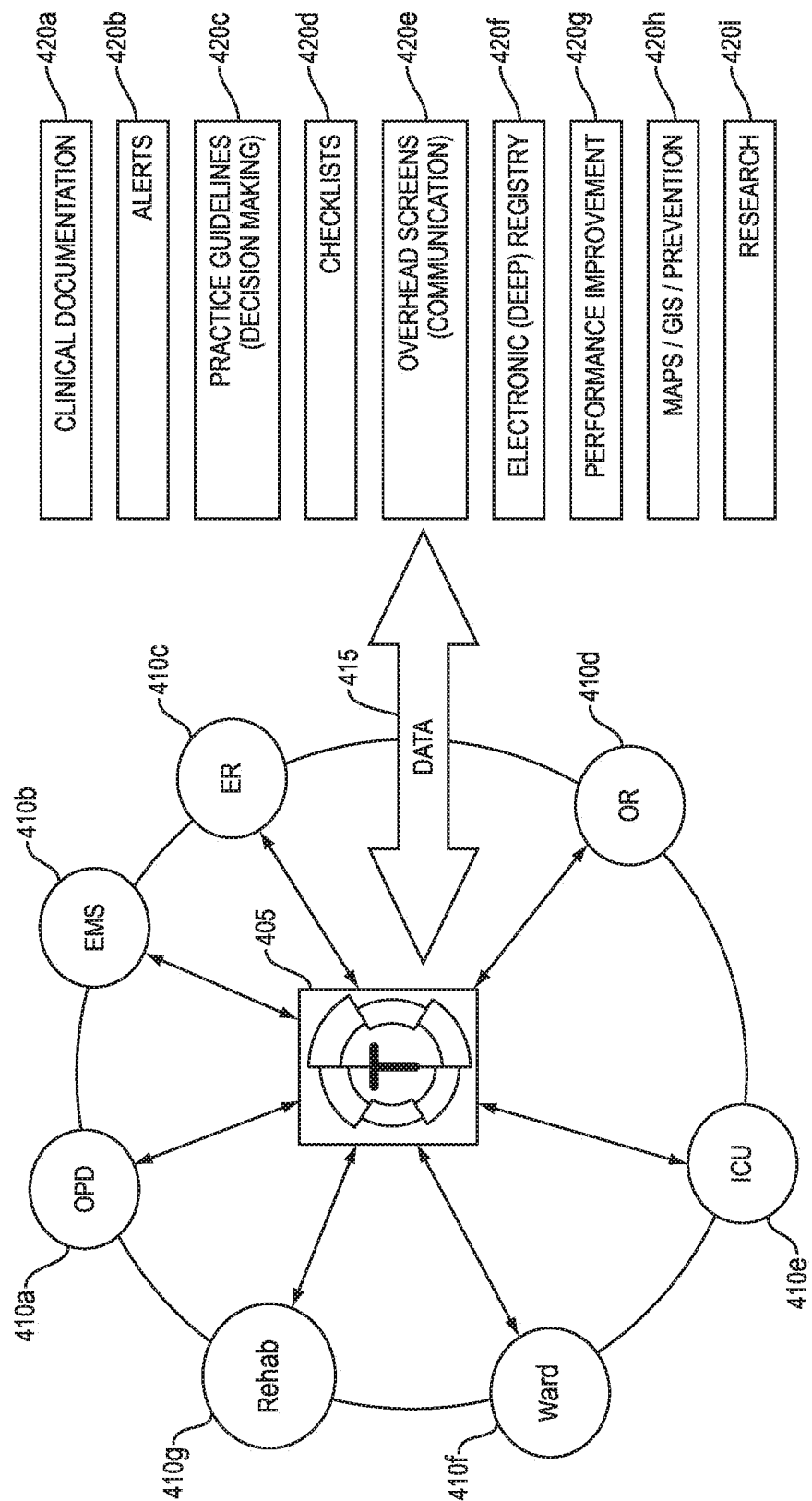
FIG. 4 depicts an illustrative data flow for a healthcare information analysis and presentation system configured for trauma assessment within a healthcare facility according to some embodiments.

FIG. 4 depicts an illustrative data flow for a healthcare information analysis and presentation system (or system) configured for trauma assessment within a healthcare facility according to some embodiments. As shown in FIG. 4, the system 405 may be accessible to various departments 410*a*-*g* of a healthcare facility, such as a hospital. For example, the system may be used within an outpatient department (OPD) 410*a*, emergency medical services (EMS) 410*b*, an emergency room (ER) 410*c*, an operating room (OR) 410*d*, an intensive care unit (ICU) 410*e*, a medical ward (e.g., oncology ward) 410*f*, or rehabilitation services ("rehab") 410*g*. In some embodiments, the healthcare information 325 and patient profiles 380 associated with the system 405 may be updated in real-time or substantially in real-time and available in the healthcare facility departments 410*a*-*g*. For instance, the physical condition of a patient (e.g., sudden loss of blood pressure) in the ER 410*c* may be viewed by a healthcare professional in the OR 410*d* as the patient is being moved to the OR 410*d* for surgery.

Data 415, such as healthcare information 325, healthcare analysis processes 330, and/or patient profiles 382, may be used for various functions 420*a*-*i*. The system 405 may include a clinical documentation 420*a* function through which medical professionals may document healthcare assessments (e.g., trauma assessments) and resuscitations simultaneously and in real-time on separate client computing devices, filling in non-overlapping and complementary data fields that may be accessed through multiple client computing devices and/or overhead monitors. The integrated documentation system may use a combined data set, created from trauma resuscitation records of multiple healthcare professionals, trauma registries, and other external data, in combination with healthcare information generated by the system 400 (e.g., physiological assessments and treatment assessments). In this manner, duplicate documentation efforts experienced in conventional systems may be reduced or even eliminated. The clinical documentation 420*a* may be output data to printable resuscitation documents (i.e., reports) with reported fields and formats tailored to healthcare professional and/or legal documentation requirements.

The system 405 may be configured to generate various alerts 420*b* based on the patient profile 380 and associated healthcare information 325. The alerts 420*b* may facilitate point-of-care decision support, for instance, for trauma teams. In some embodiments, the healthcare information application 320, for example, through the physiological assessment component 340, may be configured to recognize highly critical situations based on the healthcare information 325, the patient profile 380, the user input 372, and/or the device input 374 and to generate alerts 420*b* responsive thereto. In some embodiments, the alerts 420*b* may include heightened user prompts (e.g., GUI alert components displayed on a GUI interface) or clinical practice guidelines.

Practice guidelines 420*c*, such as clinical practice guidelines, injury-specific guidelines, and associated findings may be presented through a GUI interface on a display component of a client logic device. The practice guidelines 420*c* may be determined based on the healthcare information 325 and patient profile 380. For instance, the patient profile 380 may indicate (e.g., through analysis by the treatment assessment component 345) that one or more clinical practice guidelines or injury-specific practice guidelines may provide appropriate treatment for a trauma patient's injuries.

Checklists 420*d* may be generated by the healthcare information application 320 responsive to specific clinical circumstances. In some embodiments, the checklists 420*d* may be assembled automatically by the healthcare information application 320 according to an individual constellation of injuries and presented on a GUI interface for review at critical phases in the trauma resuscitation. In some embodiments, the checklists 420*d* may self-populate during the process of regular care and documentation as a checklist item is completed. In some embodiments, completion of checklist items may generate time-stamped documentation of completed items and detailed action during the process of trauma care. In general, the checklists 420*d* are configured to be highly relevant to individual clinical circumstances, to limit their content to important and frequently omitted steps in clinical care, and to self-populate when tasks are accomplished during the regular processes of care. In some embodiments, the checklists 420*d* may be configured to guide a medical professional team, such as a trauma team, through a systematic and complete approach to patient treatment. In some embodiments, checklists 420*d* may be specific for a patient's condition.

The healthcare information 320 and GUI elements 382 may be presented on one or more monitors 420*e*, such as overhead monitors located at various locations throughout the hospital. The information displayed on the monitors 420*e* may be updated by the healthcare information application 320 in real-time or substantially real-time to facilitate providing up-to-date and dynamic information in a dashboard format. The display of updated information through the monitors 420 may facilitate, among other things, team communication and optimization of trauma team responsiveness and use of resources.

The system 400 may generate and utilize an electronic registry 420*f* for analyzing healthcare information and diagnosing patients. In some embodiments, the electronic registry 420f may be updated in real-time or substantially real-time and may include dynamic healthcare information of current patients as well as historical information from trauma registries (i.e., a "deep" registry including a greater volume and more detailed information than conventional registries or other medical databases). A "deep" electronic registry 420f may facilitate identification of new predictive scores and previously unrecognized opportunities to improve patient safety and quality of care.

The data 415 may be used by the healthcare information application 320 to provide performance improvement 420g functions configured to improve the efficiency, efficacy, quality, and cost-effectiveness of care provided through a healthcare facility. In some embodiments, performance improvement 420g may be implemented through benchmarking based on economic value of the healthcare services provided. In some embodiments, performance improvement 420g may be at least partially based on the long-term outcomes of trauma patients, including their ability to return to work, reintegrate into society, and achieve high quality of life.

The healthcare information application 320 may be configured to analyze the healthcare information 325 to provide mapping functions 420h. For example, the mapping functions 420h may generate maps for various medical conditions or traumas using healthcare information (e.g., de-personalized healthcare information). The maps, such as geographic information system (GIS) maps, may demonstrate patterns of medical conditions or traumas that may be used to further understand and even prevent certain medical conditions and/or traumas.

As described above, the data 415 may be stored in various electronic registries 420f, such as a trauma registry (e.g., NTDB, NTR, etc.). A research function 420i may use these and similar registries and/or databases to perform research for various purposes, including improved patient diagnosis and treatment. In some embodiments, the research function 420i may be used by the system 400 to allow for the improvement of the healthcare analysis processes 330, the physiological assessment component 340, and/or the treatment assessment component 345 (i.e., to "learn").

Figure 5A:
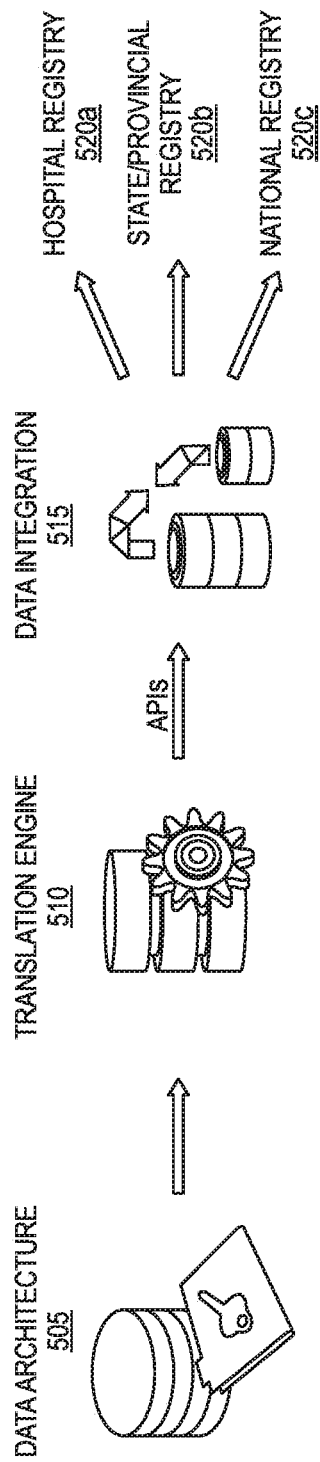
FIGS. 5A and 5B depicts an illustrative data flow for a healthcare information analysis and presentation system data integration according to some embodiments.
Figure 5B:
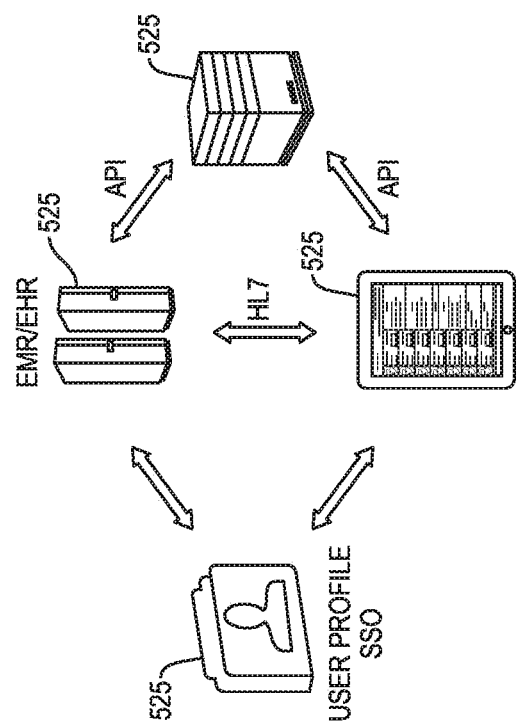

FIGS. 5A and 5B depict an illustrative data flow for a healthcare information analysis and presentation and data integration system according to some embodiments. As shown in FIG. 5A, the system data architecture 505 may include a flexible architecture that can be integrated with various existing platforms and processes, including third party systems. In some embodiments, the system data architecture 505 may process data using one or more translation engines 510 configured, for example, to translate the health information and other data as stored within the system data architecture into formats capable of being integrated with other platforms, databases, and the like. The system may use two-way communication interfaces, such as the RESTful API or H7, to achieve data integration 515 to third party systems 520a-c while maintaining and adhering to strict security processes. This framework for the exchange, sharing and integration of patient data, can allow hospitals to realize the benefits of systems according to various embodiments of the present teachings as well as existing legacy information systems without major re-investment in new technologies. As shown in FIG. 5B, a single sign-on (SSO) authentication 525 allows for seamless authentication and authorization of users from a client computing device 530 for integration of data supporting IT in integrated system and role management, and providing users with one username and password to access various applications, such as EMR/HER 535 and/or system data and applications 540.

Figure 6A:
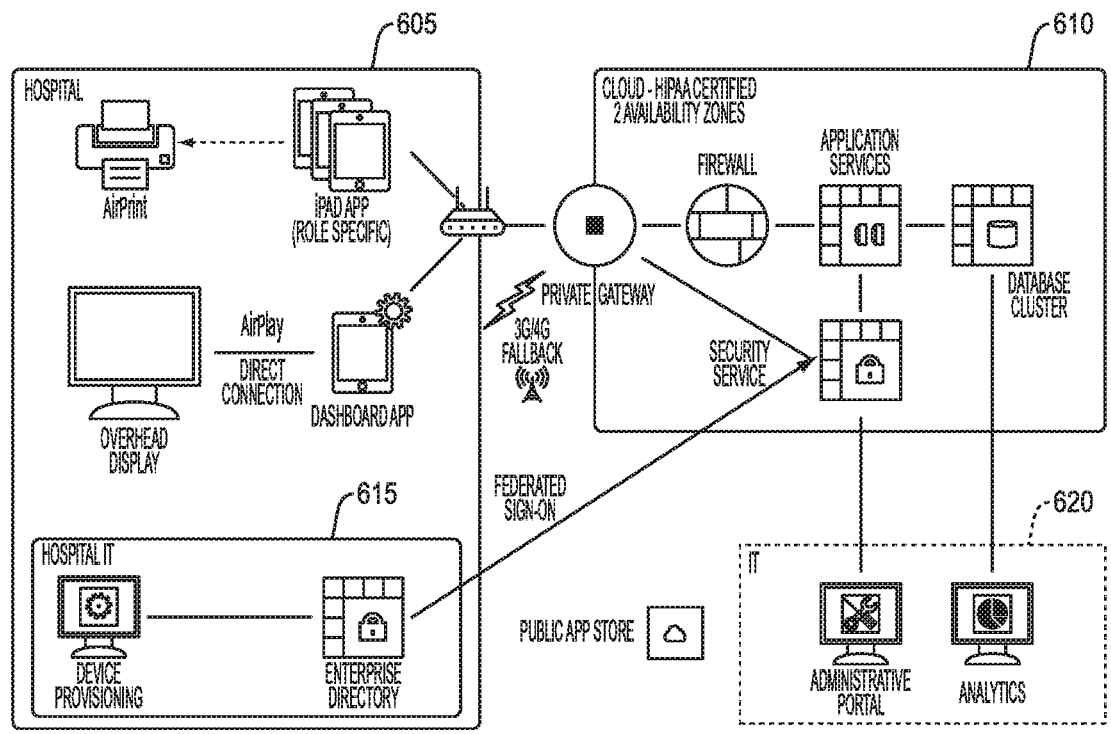
FIGS. 6A and 6B depict illustrative security and privacy models for the health information analysis and presentation system according to some embodiments.
Figure 6B:
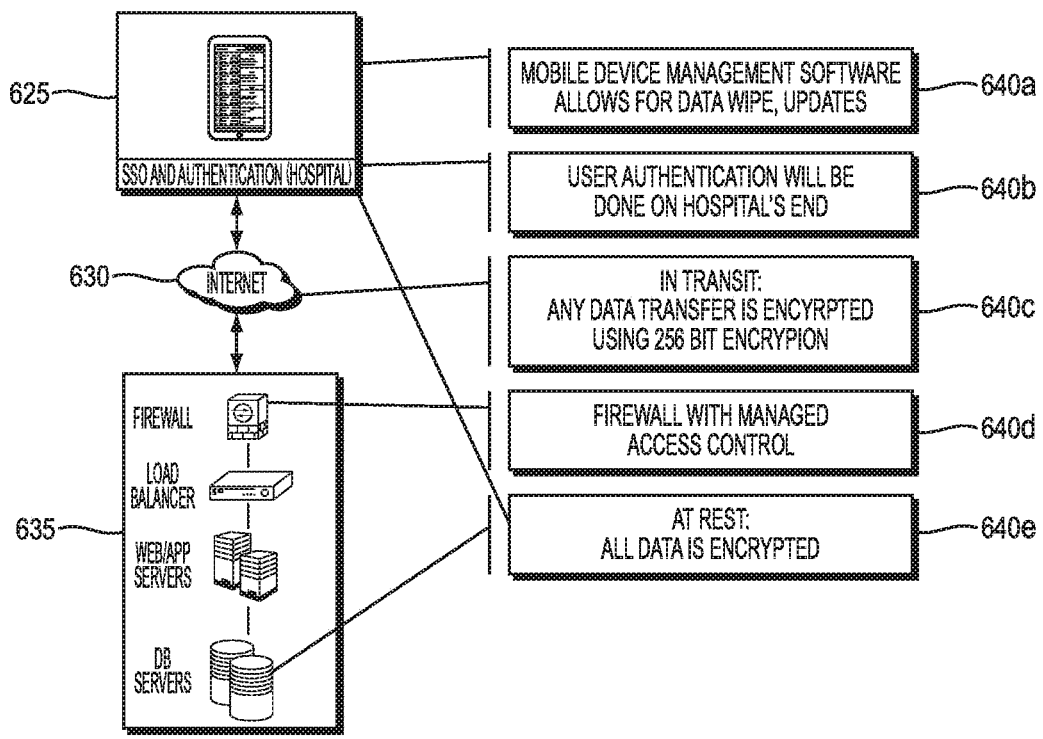

FIGS. 6A and 6B depict illustrative security and privacy models for the health information analysis and presentation system (or system) according to some embodiments. The system may implement an integrated security and privacy model configured to support security and data protection at every single interaction point, including, for example, client logic devices within a healthcare facility 605, healthcare facility IT infrastructure 615, distributed computing systems (e.g., a cloud system) 610, and system IT infrastructure 620. The system may support security and HIPAA compliancy protocols known to those having ordinary skill in the art. Non-limiting examples of implemented security features within the system according to some embodiments include SSO and integrated user profiles, internal Wi-Fi authentication, mobile device management processes, on-device data encryption, firewall protection, data encryption in transit and at rest using specifications known to those having ordinary skill in the art. As shown in FIG. 6B, security functions may be implemented at various levels within the system, such as a system in which a client mobile computing device 625 operating at a healthcare facility (e.g., a hospital) may be in communication with the system 635 through a network, such as the Internet 630. For example, mobile device management 640a may allow for data wipes and updates of the client mobile computing device 625. User authentication 640b may be done at the healthcare facility, for example using SSO authentication and all data "at rest" may be encrypted 640e. In some embodiments, all data "in transit," such as data being transmitted through the Internet 630 may be encrypted 640c, for example, through 256 bit encryption. The system 635 may implement a firewall 640d with managed access control and may encrypt 640e all data "at rest."

As described above, the system may generate GUI elements for receiving and/or presenting healthcare information and patient profiles. In some embodiments, the GUI elements may include user interfaces (or screens, windows, "dashboards," or the like).

Figure 7:
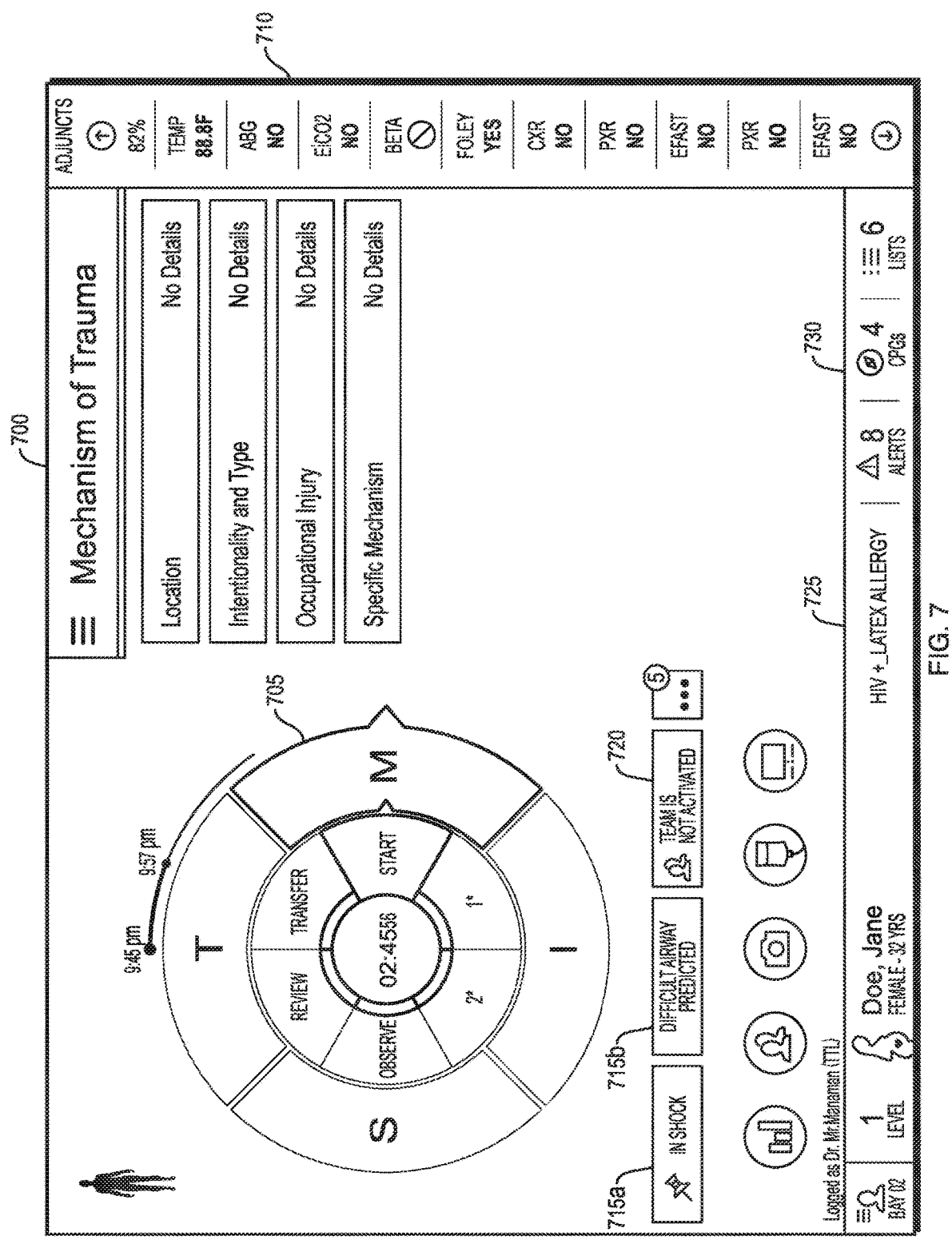
FIG. 7 depicts an illustrative trauma system dashboard according to a first embodiment.

FIG. 7 depicts an illustrative trauma system dashboard according to a first embodiment. As shown in FIG. 7, a trauma system dashboard 700 may include a trauma lifecycle element 705 configured to provide information associated with where the patient is in the trauma care timeline. The trauma lifecycle element 705 may indicate the duration of time since the patient was admitted and which steps have been completed, such as determining the mechanism of the trauma (M), determining injuries (I), survey (S), and transport (T). The dashboard 700 may include various patient profile information fields 710, 725, such as patient vitals and tests completed 710 and patient demographic information and medical conditions 725. In some embodiments, the dashboard 700 may present physiological and/or treatment assessments 715a, 715b and functions 730, such as alerts, protocols, and checklists automatically and dynamically generated by the healthcare information application 320. The dashboard may also present information associated with medical professionals and/or teams 720 that have been involved with the patient.

Figure 8:
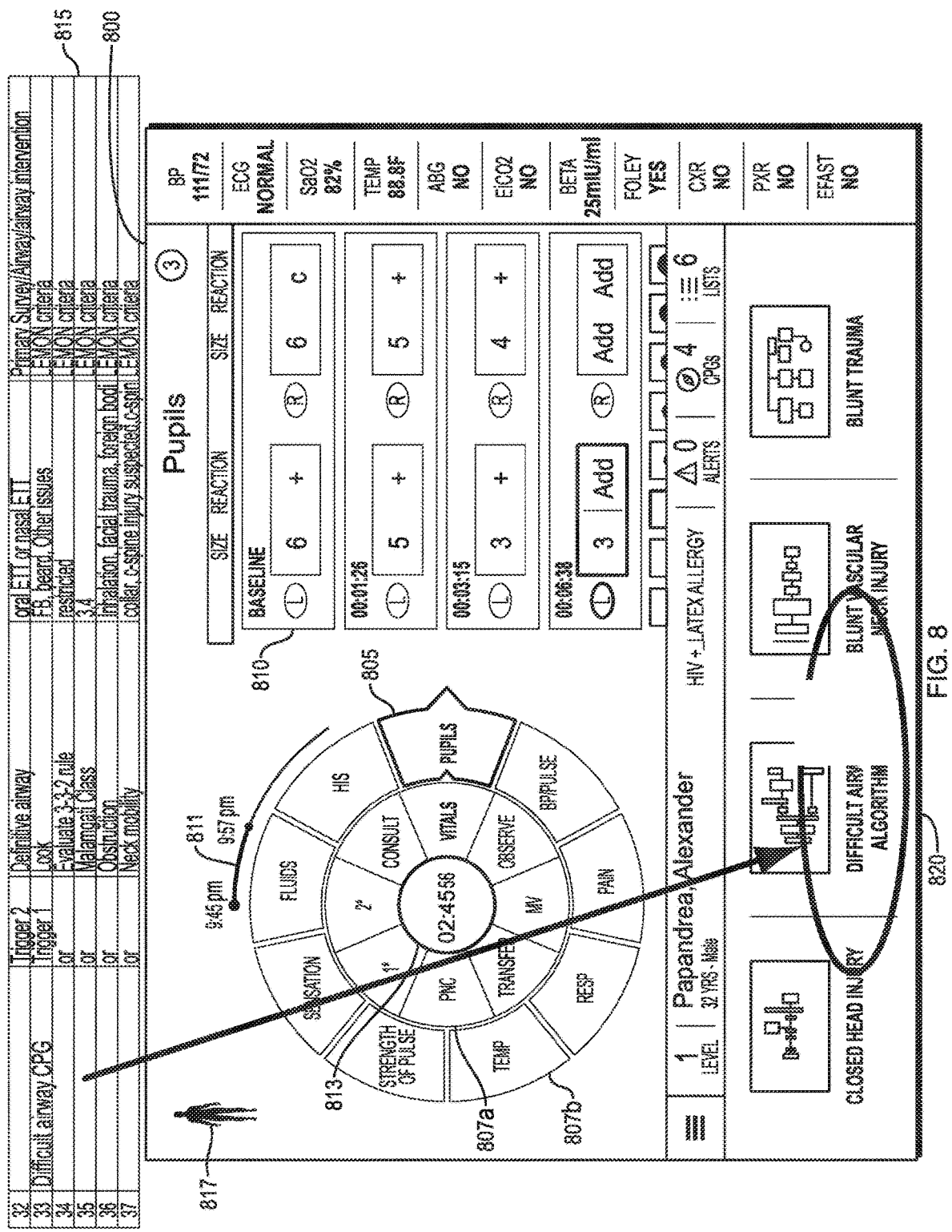
FIG. 8 depicts an illustrative trauma system dashboard according to a second embodiment.
Figure 9:
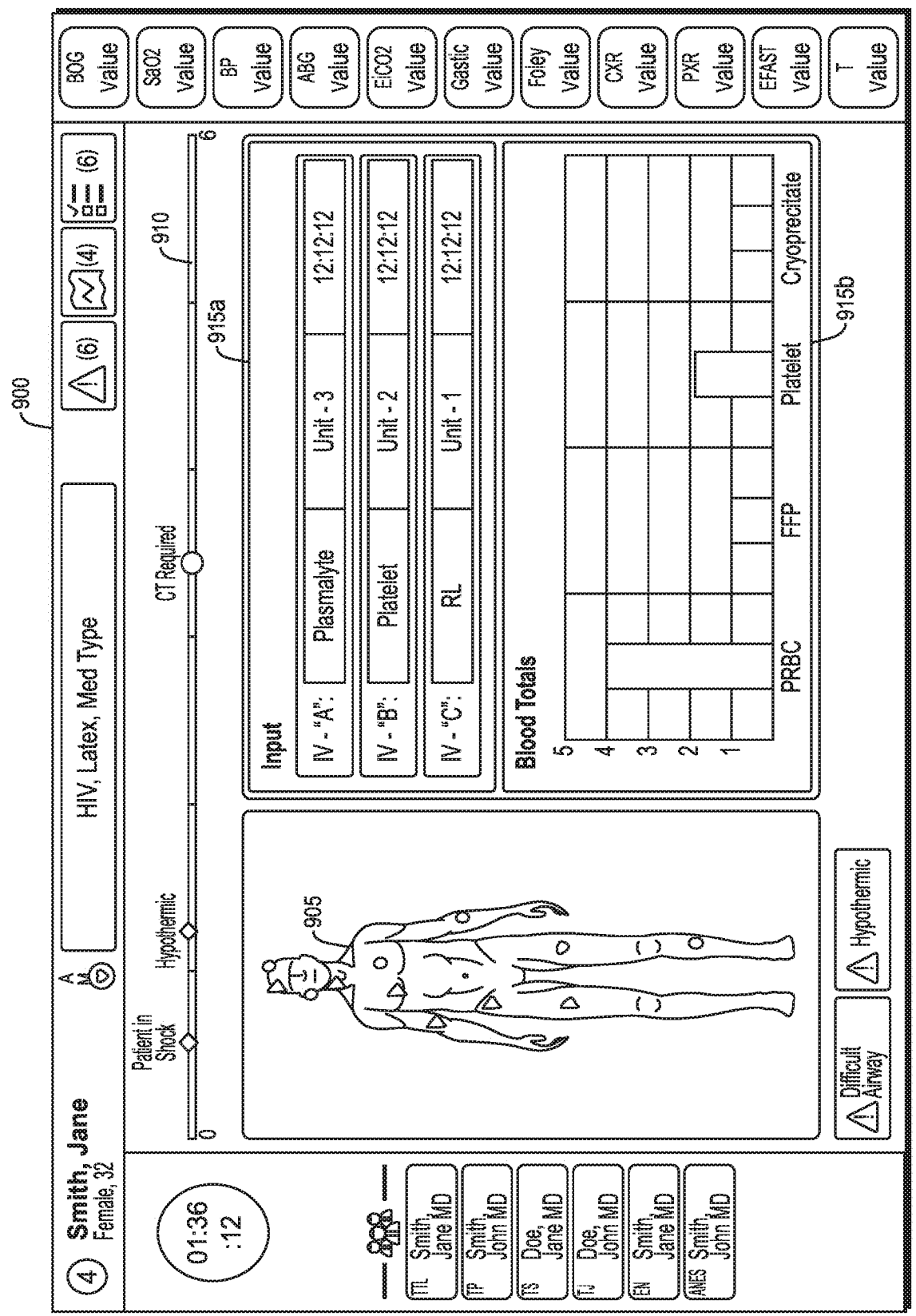
FIG. 9 depicts an illustrative trauma system dashboard according to a third embodiment.
Figure 10:
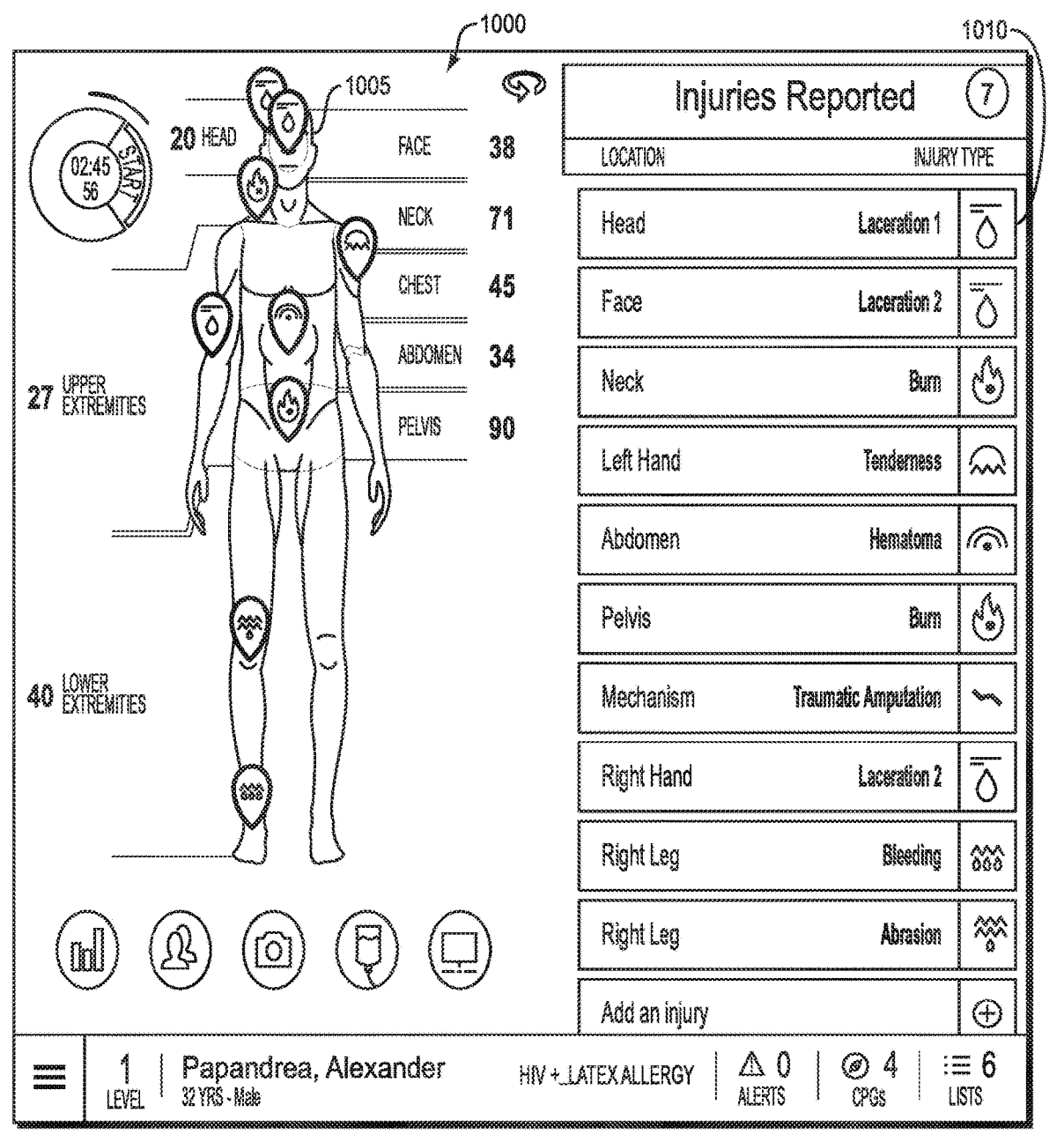

FIG. 8 depicts an illustrative trauma system dashboard according to a second embodiment. As shown in FIG. 8, a trauma system dashboard 800 may include a patient profile navigation element 805 configured to allow users to access information objects configured to provide information about the physiological status of the patient, including a primary navigation level 807a and a secondary navigation level 807b. A user may select a physiological status item or selection area, such as "pupils," to cause information elements (status fields) 810 and other information objects associated with the item to be presented on the dashboard 800. In FIG. 8, selection of "pupils" on the patient profile element selection areas 805 has caused status fields 810 associated with the status of the patient's pupils to be presented on the dashboard. Healthcare information recorded in the database patient profile 815 may prompt the appearance of injury-specific clinical practice guidelines 820 on the dashboard. In addition, trends and historical data associated with the healthcare information depicted in the dashboard 800 may be graphically presented thereon. In some embodiments, the trauma system dashboard 800 may include a time elapsed information object 811 and/or timer 813 configured to indicate the time that has elapsed since an event, such as patient admission, trauma event, surgery, shock, or the like. In some embodiments, one or more of the selection areas 805 may be associated with a different time elapsed information object 811 and/or timer 813. In some embodiments, the trauma system dashboard 800 may include a patient graphical representation selection object 817 that may allow a user to access a graphical representation of the patient, for example, such as depicted in FIGS. 10, FIG. 9 depicts an illustrative trauma system dashboard according to a third embodiment. The dashboard 900 may be configured as an overhead dashboard (e.g., displayed on a common overhead monitor) to be viewed simultaneously by multiple members of a medical team, such as a trauma or surgical team. The dashboard 900 may include a graphical representation of the patient 905 which may include various medical conditions, injuries, or the like arranged thereon as well as a timeline 910 of the patient's medical conditions, diagnostic tests, procedures, or the like. The dashboard 900 may be configured to provide healthcare information associated with the volume of resuscitation fluids, including blood products, administered at a given point time 915a, 915b.

FIG. 10 depicts an illustrative trauma system dashboard according to a fourth embodiment. The dashboard 1000 may include a graphical representation of the body of the patient 1005 configured to allow a medical professional to enter healthcare information associated with injuries to the patient. A list of injuries 1010 may be reported through the dashboard 1000. For example, a user may select a portion of the body (e.g., the left arm) of the graphical representation of the body of the patient 1005, e.g., by touching that portion, and may be presented with a menu of injury types and be prompted to select an injury type (e.g., laceration, burn, bleeding, sensitivity, skin discoloration, rash, abrasion, etc.) as well as information associated with the injury, such as the severity or degree of the injury. In other embodiments, rather than presenting a menu to the medical professional, the selection of an anatomical portion of the graphical representation of the body can allow the medical professional to type in an injury into a text field presented to the medical professional.

Figure 11A:
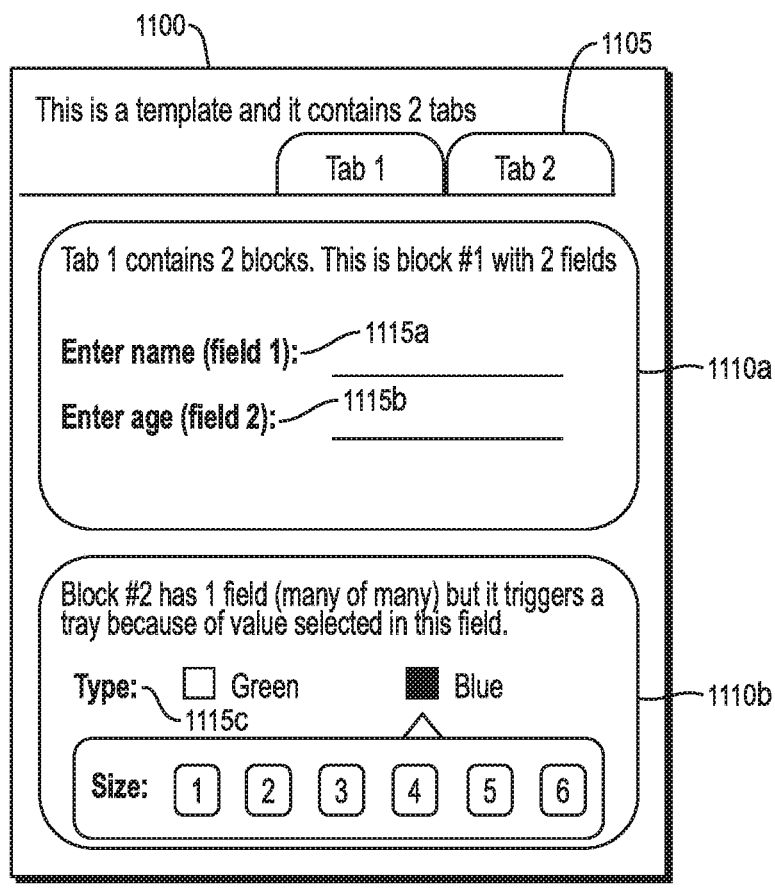
FIG. 11A depicts an illustrative GUI template according to some embodiments.

In some embodiments, the GUI elements and interfaces may be configured based on GUI templates using a construction engine executed by the healthcare information application. A user may configure a GUI interface, such as a dashboard, using the construction engine. FIG. 11A depicts an illustrative GUI template according to some embodiments. As shown in FIG. 11A, a template may include tabs 1105, blocks 1110a, 1110b and fields 1115a-c. In some embodiments, each screen or dashboard rendered on a display component is a template 1100. A template 1100 can contain one or more tabs 1105, each tab 1105 can contain one or more blocks 1110a, 1110b of content, and each block 1110a, 1110b can contain one or more fields 1115a-c. Each field 1115a-c may provide a user with an option to select an associated value, for example, through typing a text or a number, making one or more selections, selecting an icon, etc. In some embodiments, selection of a value may cause the appearance of a window or other GUI object requesting more information and/or a function, such as a checklist, protocol guideline, or alert.

Figures 11B, 11C, 11D, 11E:
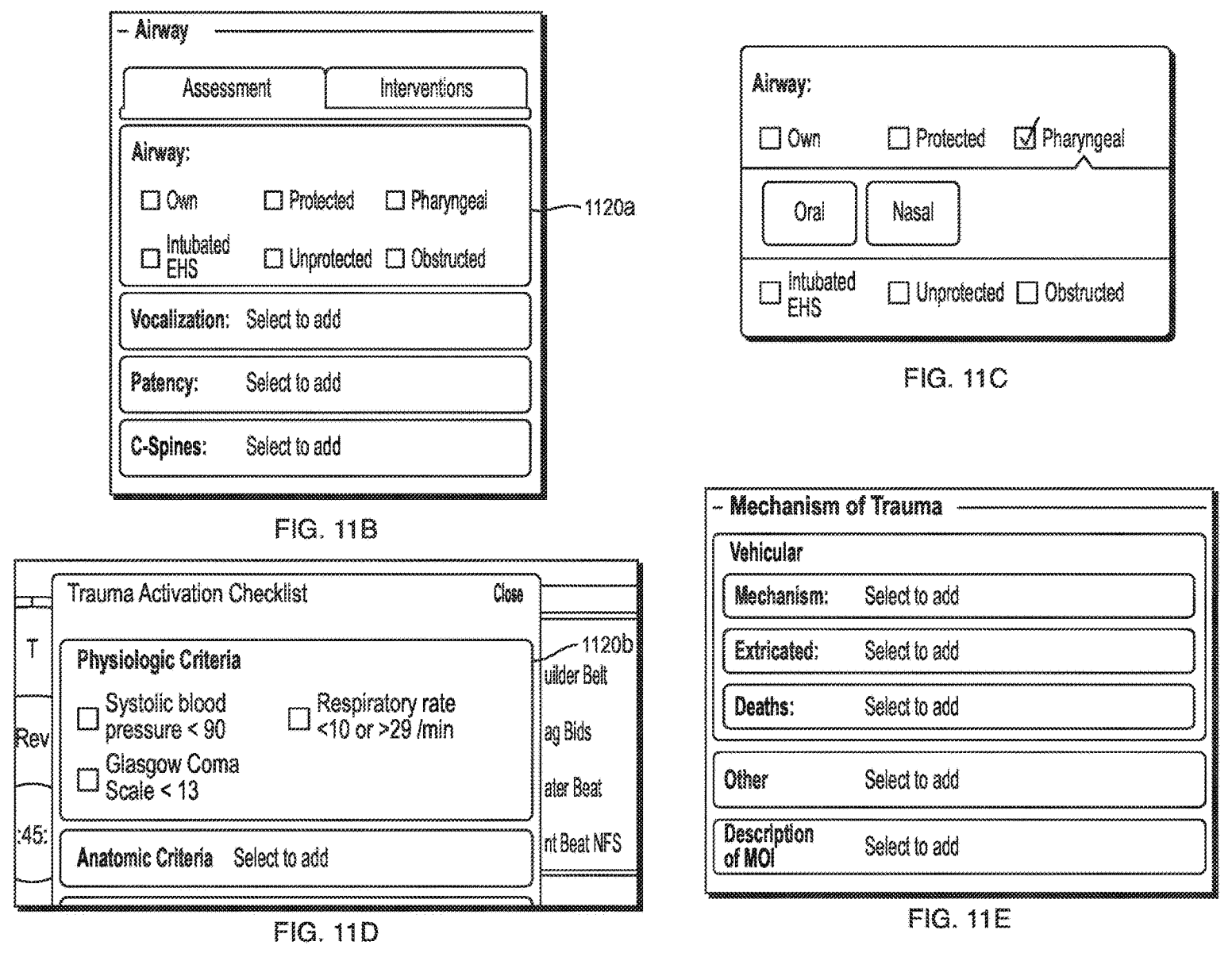

Through the use of templates, users may configure dashboards using known GUI and data objects, such as fields. FIGS. 11B and 11C depict illustrative templates directed toward airway assessment according to some embodiments. FIGS. 11D and 11E depict illustrative templates directed toward trauma investigation according to some embodiments. In some embodiments, a user may select various elements, such as an airway element 1120a, a physiological criteria element 1120b, or the like to include on a GUI. Although FIGS. 11A-11E depict a plurality of elements, only the airway element 1120a and the physiological criteria element 1120b are labeled to simplify the figures. A user may select an element 1120a, 1120b and link it to data and/or selection of a category. For instance, the physiological criteria element 1120b may be linked to the systolic blood pressure of a patient and may be displayed when a particular secondary selection area (or "category") 1212 is selected on the navigation object 1204. In this manner, users may efficiently and effectively generate customized GUI interfaces, dashboards, and the like.

Figure 11F:
FIG. 11F depicts an illustrative custom template configured to allow a user to enter vehicular accident trauma information according to some embodiments.

FIG. 11F depicts an illustrative custom template configured to allow a user to enter vehicular accident trauma information according to some embodiments. For example, the template may include elements for specifying the type of vehicle 1125a, the position of the vehicle/impact type 1125b, whether the accident involved a rollover 1125c, the number of vehicles involved in the accident 1125d, speed of the vehicle at the time of the accident 1125e, or the like.

Figure 12A:
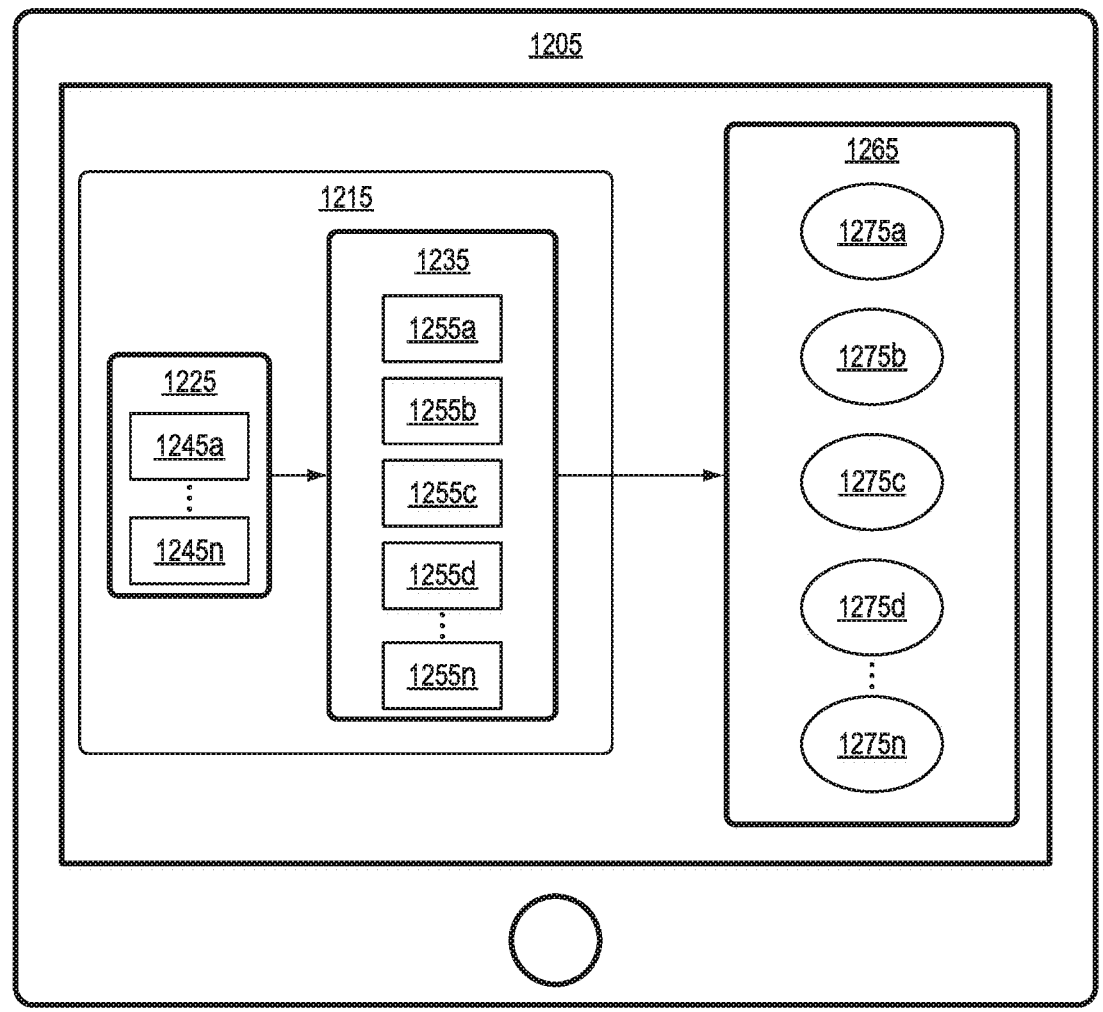
FIG. 12A depicts an illustrative graphical user interface according to some embodiments.

FIG. 12A depicts an illustrative graphical user interface according to some embodiments. As shown in FIG. 12A, a GUI may be presented on a display device of a client computing device 1205. For instance, a GUI may be displayed on a touch screen of a tablet computing device. The GUI may include a navigation object 1215 that includes a plurality of navigation levels, such as primary graphical objects (for example, a primary navigation level) 1225 and secondary graphical objects (for example, a secondary navigation level 1235). The navigation level is not limited to two navigation levels, as any number of navigation levels capable of operating according to some embodiments is contemplated herein. For example, the navigation object 1215 may include one, two, three, four, five, ten, fifteen, twenty, or any range of navigation levels between any two of these values. Each navigation level may include one or more selection areas 1245a-n, 1255a-n that may be selected by a user. In some embodiments, the presentation, configuration, and/or selection areas 1245a-n, 1255a-n of a navigation level 1225, 1235 may be specified by the system based on the state of a navigation level and/or the selection of a selection area. For example, selection by a user of a selection area 1245a-n on the primary navigation level 1225 may cause the presentation of the secondary navigation level 1235 and/or the display of particular selection areas 1255a-n on the secondary navigation level. In another example, selection of selection area 1245a may cause a particular secondary navigation level 1235 to be displayed that includes selection areas 1255a and 1255c. In a further example, selection of selection area 1245*n* may cause a particular secondary navigation level 1235 to be displayed that includes selection areas 1255*b* and 1255*n*.

The GUI depicted in FIG. 12A may include an information object 1265 that may include one or more information elements 1275*a-n*. The information object 1265 may be configured to display information, such as healthcare information received from a server computing device. In some embodiments, the information object 1265 may include one or more information elements 1275*a-n* configured to display data, such as data associated with a patient. The visibility of the information object 1265 and/or the particular displayed information elements 1275 may be determined based on the selected or active selection areas 1245*a-n*, 1255*a-n*. For instance, the selection by a user of selection area 1245*a* on the primary navigation level 1225 may cause a particular secondary navigation level 1235, with a particular set of selection areas 1255*a-n*, to be displayed on the GUI. For example, the primary navigation level 1225 may include a diagnostics selection area 1245*a-n* that, when active, may cause a diagnostics secondary navigation level 1235 to be displayed with selection areas 1255*a-n* for particular diagnostic tests.

Selection of a diagnostic test via the selection areas 1255*a-n* may cause an information object 1265 to be presented on the GUI that has information elements 1275*a-n* for displaying information associated with a particular diagnostic test for a subject patient. In some embodiments, portions of the information object 1265, including the information elements 1275*a-n* may be selectable by a user and, for example, selection thereof may cause the presentation of other GUI elements, including, without limitation, information objects, information elements, navigation objects, and/or navigation levels. In some embodiments, the information object 1265 or a portion thereof may include a flow chart, clinical practice guideline, or other treatment process. The use of multiple navigation levels and information objects, such as the primary navigation level 1225 and the secondary navigation level 1235, may allow a user to efficiently access and/or edit the vast amount information within the system in a minimal number of steps. For instance, in reference to FIG. 17A, selection of the "1°" selection area 1245 followed by selection of the "Start" selection area 1255 may cause the presentation of the "Treatments on Scene" information object 1265, which may allow full access to the information elements 1275 associated with treatments given to the patient at the scene of a trauma.

Although FIG. 12A and certain embodiments provided herein describe the primary graphical objects 1225 and the secondary graphical objects 1235 as navigation objects or levels, embodiments are not so limited as the primary graphical objects and the secondary graphical objects may include any GUI object capable of operating according to some embodiments. In some embodiments, the selection of a primary graphical object 1225 effects the presentation of, the data associated with, and/or the event associated with a selection of the one or more of the secondary graphical objects 1235. For example, selection of a first primary graphical object 1225 may cause a first secondary graphical object 1235 to be presented on the screen. Selection of the first secondary graphical object 1235 may cause a first selection event (for instance, navigation to a particular screen, data entry event, or the like). Selection of a second primary graphical object 1225 may cause a second and a third secondary graphical object 1235 to be presented on the screen. Selection of the second secondary graphical object 1235 may cause a second selection event and selection of the third secondary graphical object may cause a third selection events. In some embodiments, the primary graphical objects may be and/or may include selection areas 1245*a-n* and the secondary graphical objects 1235 may be and/or may include selection areas 1255*a-n*.

The navigation object 1215 may be configured in various shapes and/or forms, including a circle shape, a rectangular shape, a square shape, a menu form, and/or any other shape or form capable of operating according to some embodiments described herein. As shown in FIG. 12B, FIGS. 15A-15D, FIG. 16A, FIGS. 17A-17E, and FIGS. 23A-23E, the navigation object 1215 may have a circular or substantially circular shape. In some embodiments, the secondary navigation level 1235 may encompass, envelop, or otherwise surround the primary navigation level 1225, such as through the primary and secondary navigation levels being configured as concentric circles, rectangles, or other concentric shapes.

Figure 12B:
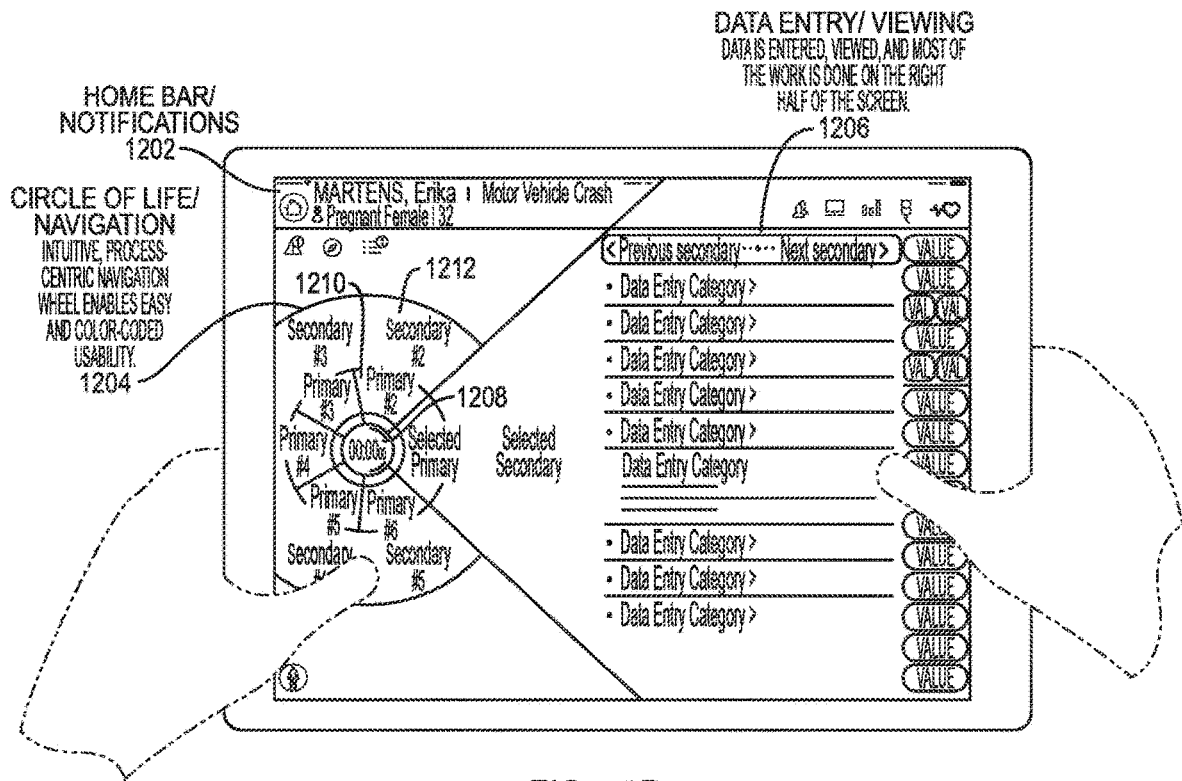
FIG. 12B depicts an illustrative overview dashboard according to some embodiments.

FIG. 12B depicts an illustrative overview dashboard according to some embodiments. As shown in FIG. 12B, an overview dashboard may include various GUI objects, such as a home bar 1202 (or notifications bar), a navigation object 1204 (or circle of life object or navigation wheel), and data entry objects 1206. In some embodiments, the navigation object 1204 may be launched responsive to an event, such as logging into the system, accessing a patient record, or the like. In some embodiments, the notifications bar 1202 may be configured to provide information relating to a subject patient associated with the dashboard and data associated therewith, such as information relating to the patient's name, physical condition (i.e. "pregnant female," and "age 32"), and source of trauma (e.g., "Motor Vehicle Crash"). In some embodiments, any alerts, messages, or other notifications may be presented on the notifications bar 1202, such as treatment instructions, vitals outside of threshold values, messages (e.g., "transport patient to OR"), or the like.

In some embodiments, the navigation object 1204 may include a timer 1208 configured to present a time associated with a procedure, patient, process, event, or the like. In some embodiments, the timer 1208 may be associated with a primary category 1210 and/or a secondary selection area 1212. Time has a major effect on the outcome of patient treatment, particularly in trauma situations. Accordingly, the timer 1208 may operate to provide a constant reminder of time passed since the occurrence of an event, such as a trauma suffered by a subject patient. In a trauma situation, stabilization within the first six hours increases the chance of long-term survival of the patient. As such, the timer 1208 may operate to provide medical professionals with a constant update on the time associated with treating the subject patient to allow the treatment team, among other things, to focus on time-based treatment goals. In some embodiments, multiple timers or timed events may be maintained within the system. Selection of a selection area 1210, 1212 may cause a corresponding timer 1208 to be displayed. In some embodiments, there is one main timer maintained within the system, for example, time elapsed since admission, time elapsed since trauma, or the like which the timer 1208 may display.

The data entry objects 1206 may allow a user to access and view health information relating to the patient, such as vitals, medications prescribed and/or taken, diagnostic tests, and trends thereof, or the like. For example, the data entry objects 1206 may include a selection object to view x-ray diagnostic tests relating to the subject patient.

Figure 12C:
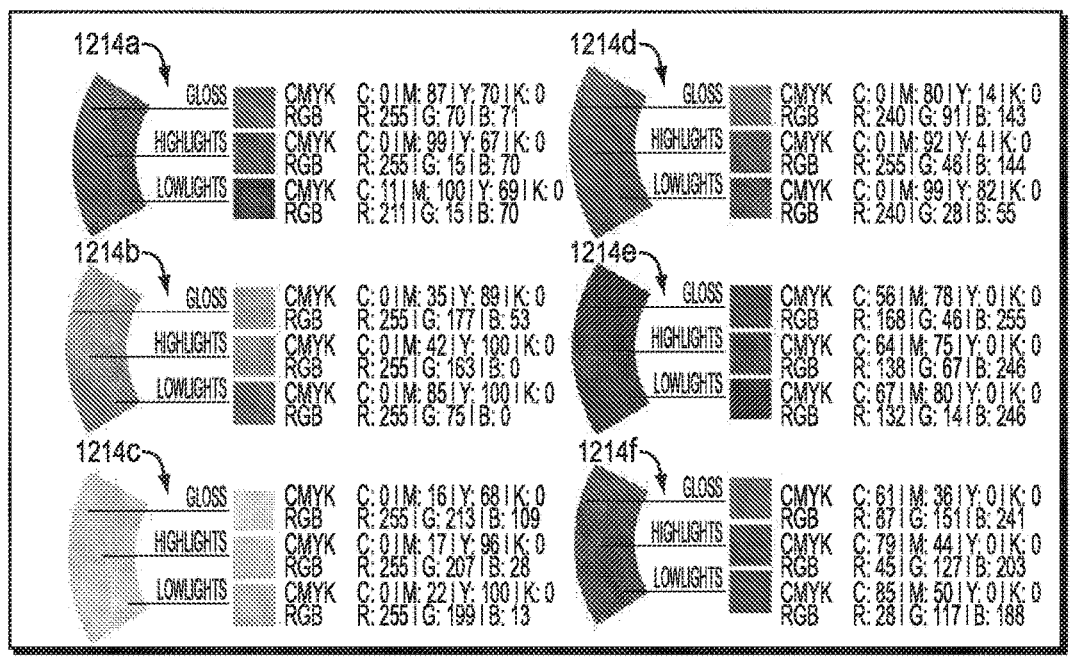
FIG. 12C depicts a color scheme used within the healthcare information application according to some embodiments.

FIG. 12C depicts a color scheme used within the healthcare information application according to some embodiments. As shown in FIG. 12C, colors and color schemes may be used to identify information, status, processes, categories, or the like. In this manner, medical professionals may be able to readily identify information associated with a patient, process, category, or the like through the use of colors. As such, through training and/or familiarity with the healthcare information application, medical professionals can make associations between displayed colors and information and/or the treatment of a patient, which may be more efficient and effective than viewing the same information through text, menus, or other means of communication. For instance, the colors may parallel the stabilization of a patient in a trauma situation. In another instance, the use of colors and their relationship with data within the healthcare information application may operate to connect the role of data within the healthcare information application and what is actually occurring in the real world. In some embodiments, colors may be associated with the primary categories 1210. For instance, "Start" may be associated with red 1214*a*, "1°" (primary survey, for example, airway, breathing, exposure, circulation, and disability assessments) may be associated with orange 1214*b*, "2°" (secondary survey) may be associated with yellow 1214*c*, "Flowsheet" may be associated with pink 1214*d*, "Review" may be associated with purple 1214*e*, and "Transfer" may be associated with blue 1214*f*.

Figure 12D:
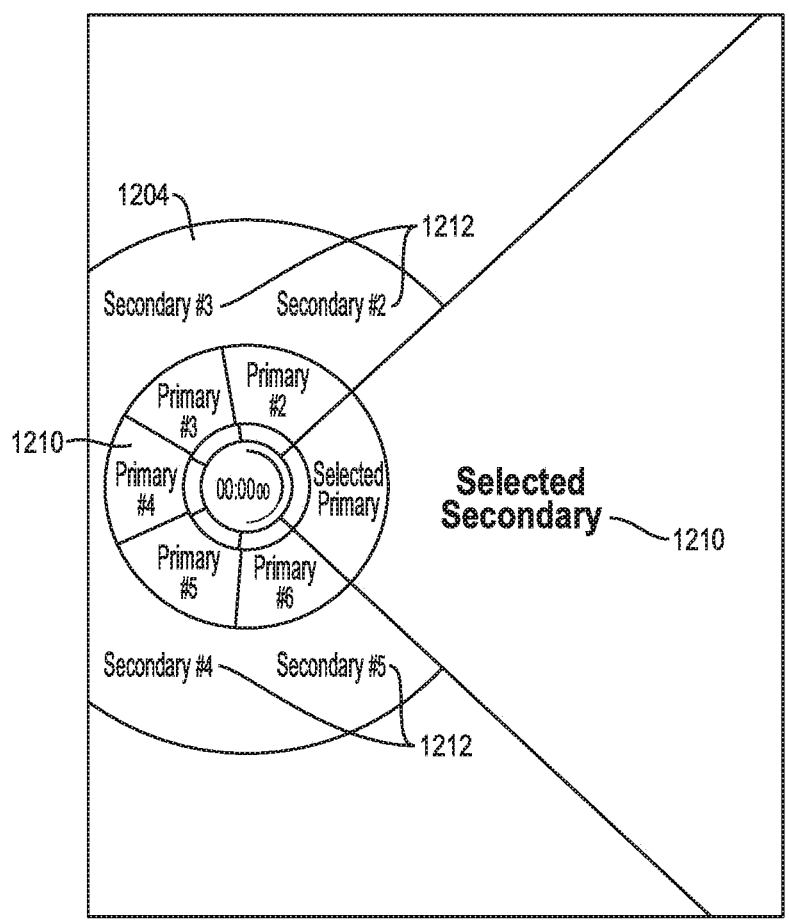
FIG. 12D depicts primary and secondary categories according to some embodiments.

As shown in FIG. 12D, the circular navigation object 1204 allows for intuitive, process-centric navigation. In some embodiments, the navigation object 1204 may include primary selection areas (or "categories") 1210 (for instance, "Primary #2," "Primary #3," etc.) that may be selected and/or ordered based on standard ordering or procedures and processes within a particular medical unit. In the embodiment depicted in FIG. 12D, the Primary #1 primary selection area 1210 has been selected and is the "Selected Primary" selection area. In some embodiments, the secondary selection areas 1212 may be presented based on the "Selected Primary" selection area 1210. For example, in a trauma application, primary selection areas 1210 may include "Start," "1°," "2°," "Flowsheet," "Review," and "Transfer." In some embodiments, the secondary selection areas 1212 may include subsections of a primary category. A user may select a primary selection area 1210 and a secondary treatment selection area 1212. The selected secondary treatment selection area 1216 may be expanded within the dashboard.

Figure 12E:
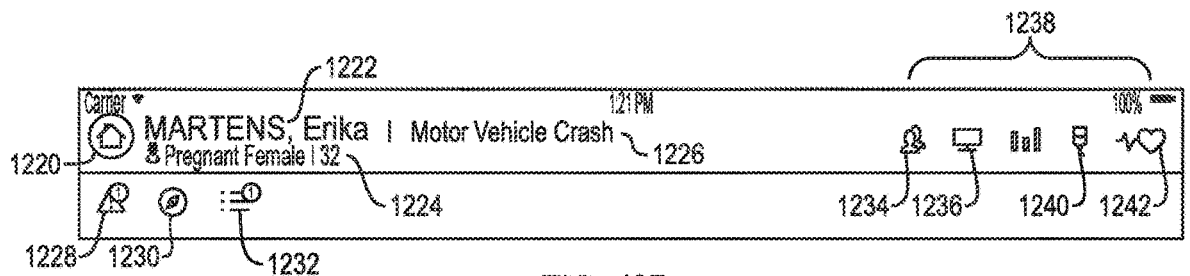
FIG. 12E depicts an illustrative navigation bar according to some embodiments.

FIG. 12E depicts an illustrative navigation bar according to some embodiments. As shown in FIG. 12E, the navigation bar may include a home button 1220 configured to navigate to a home screen, a patient name object 1222 and a patient details object 1224, and a method of trauma object 1226. The navigation bar may include a primary notification menu that may include an alerts object 1228 that may be selected to display current alerts, a clinical practice guideline object 1230 that may be selected to display active, relevant clinical practice guidelines, and a checklists object 1232 that may be selected to view current checklists. The navigation bar can also include a secondary notification menu that may include a team object 1234 that may be selected to view and/or assign members to a treatment team, a display object 1236 that may be selected to view and/or manage output displays, a reports object 1238 that may be selected to view and/or generate reports, a fluids object 1240 that may be selected to view and/or add fluid treatments, and a vitals object 1242 that may be selected to view and/or add vital sign values.

Figure 12F:
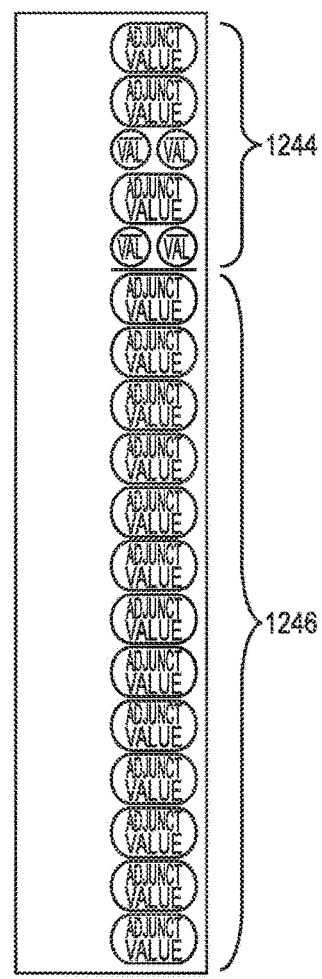
FIG. 12F depicts an illustrative adjuncts bar according to some embodiments.
Figure 20A:
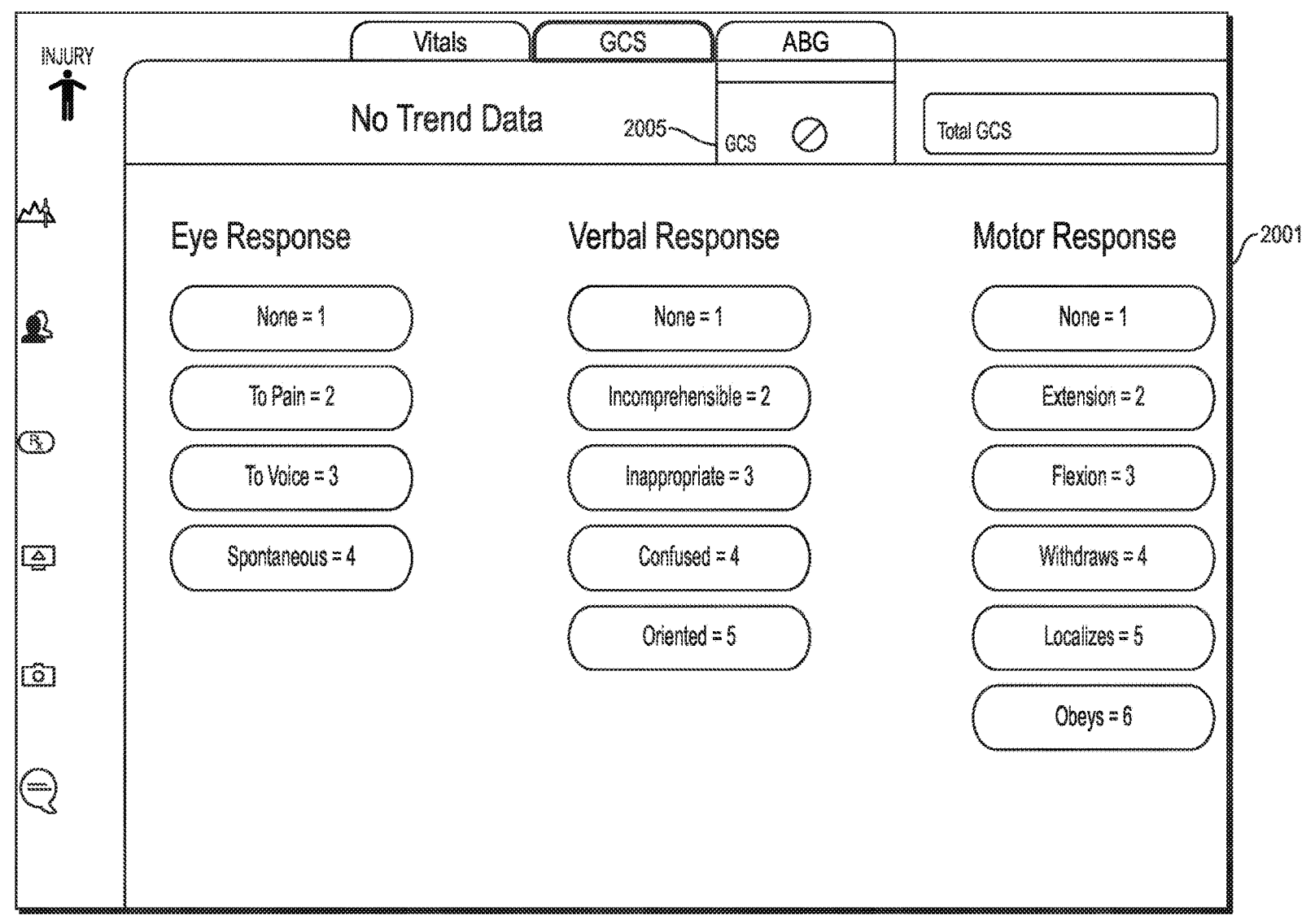
Figure 20B:
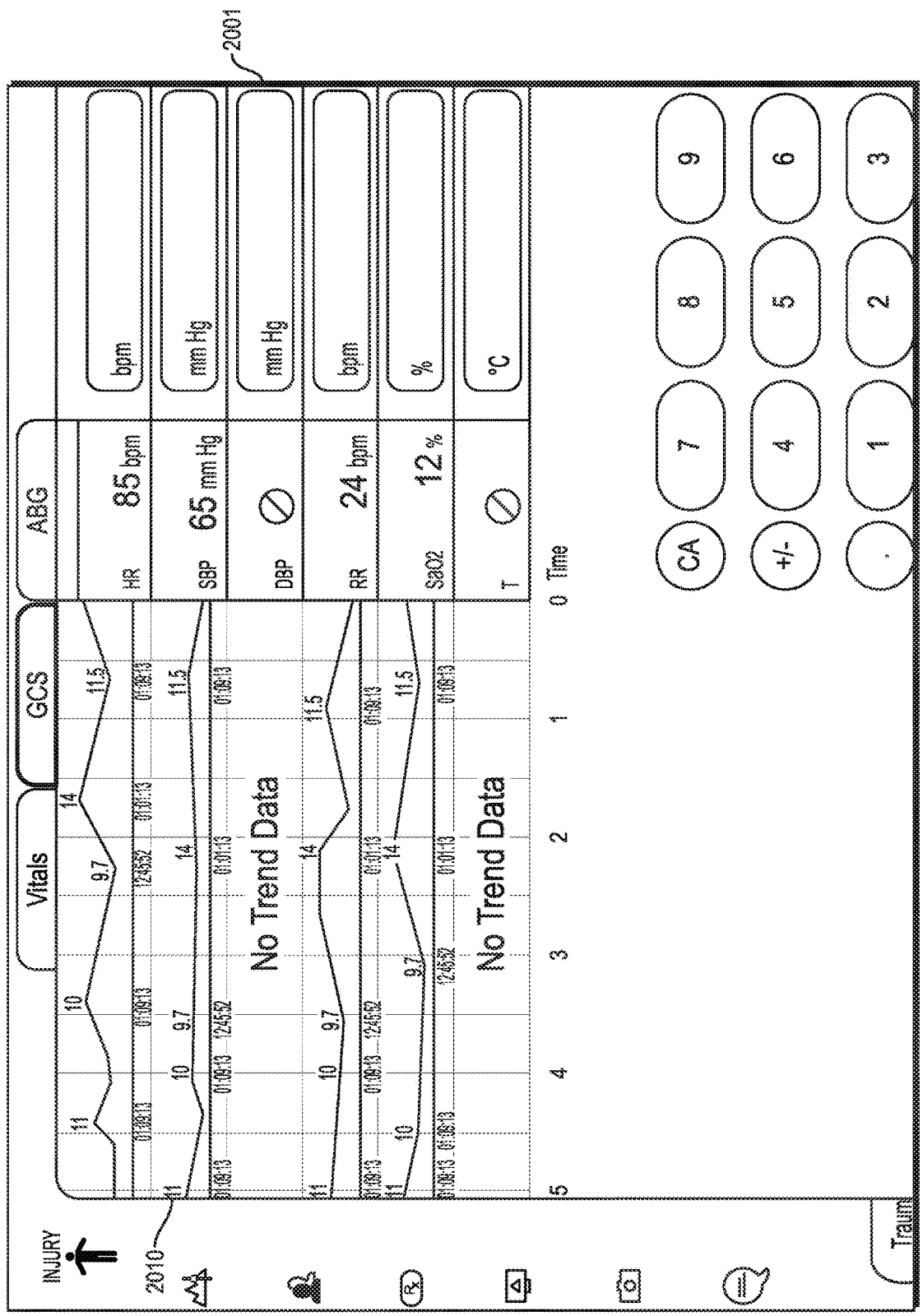

FIGS. 20A-20B depict an illustrative screen 2001 according to some embodiments for viewing and/or adding vital information 2005 and other patient information, such as Arterial Blood Gas (ABG), Glasgow Coma Scale (GCS) 2010, or the like. FIG. 12F depicts an illustrative adjunct bar according to some embodiments. The adjunct bar may include trending selection objects 1244 configured to display current and historical trend values, for example, in a graph format. Non-trending selection objects 1246 may also be presented on the adjunct bar configured to depict current values of specific adjunct selection objects (e.g., vitals). In some embodiments, colors may be used to provide information about the values, such as positive and/or desired values being colored green and negative and/or urgent values being colored red.

Figure 12G:
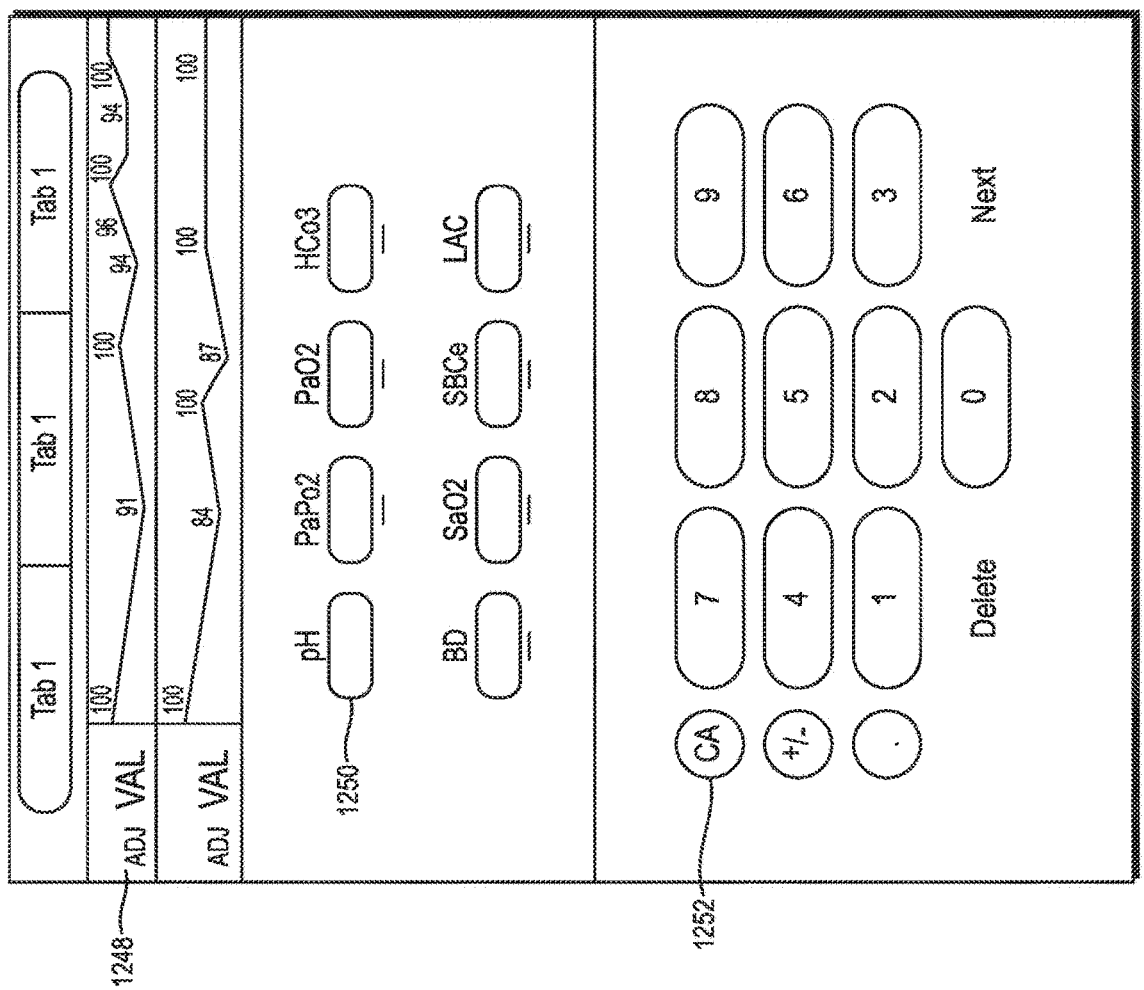
FIG. 12G depicts a trend display according to some embodiments.

FIG. 12G depicts a trend display according to some embodiments. As shown in FIG. 12G, a trend display may include a trending data section 1248. In some embodiments, the trending data section 1248 may be presented as an expanded panel from the data entry/viewing area 1206 depicted in FIG. 12C configured to present current and historical values in a trend graph. The trend display may include various trend fields 1250 that may be configured to streamline the data entry process by placing symbols, decimal points, and skipping between entry fields automatically for rapid entry of values. Non-limiting examples of trend fields 1250 may include pH, $PaPO_2$, $PaO_2$, $HCo_3$, BD, $SaO_2$, $SBCe$, and LAC. The trend display, as well as other screens and displays throughout the healthcare information application, may include a contextual calculator 1252 that may present values, operators, symbols, and layouts based on the context in which they are presented and/or associated content being displayed.

Figure 13A:
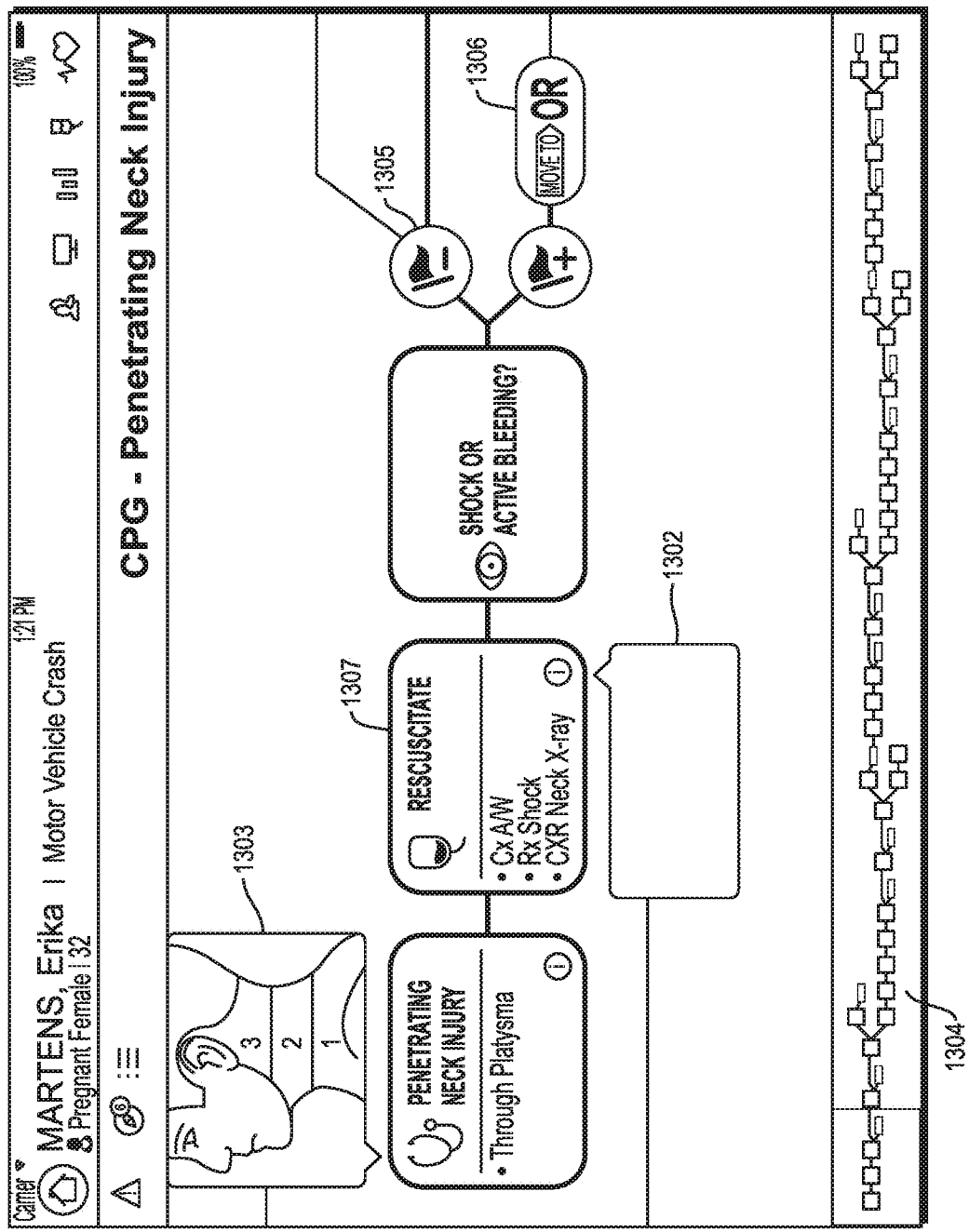
FIGS. 13A-13C depict illustrative clinical practice guidelines (CPG) process displays according to a first embodiment.
Figure 13B:
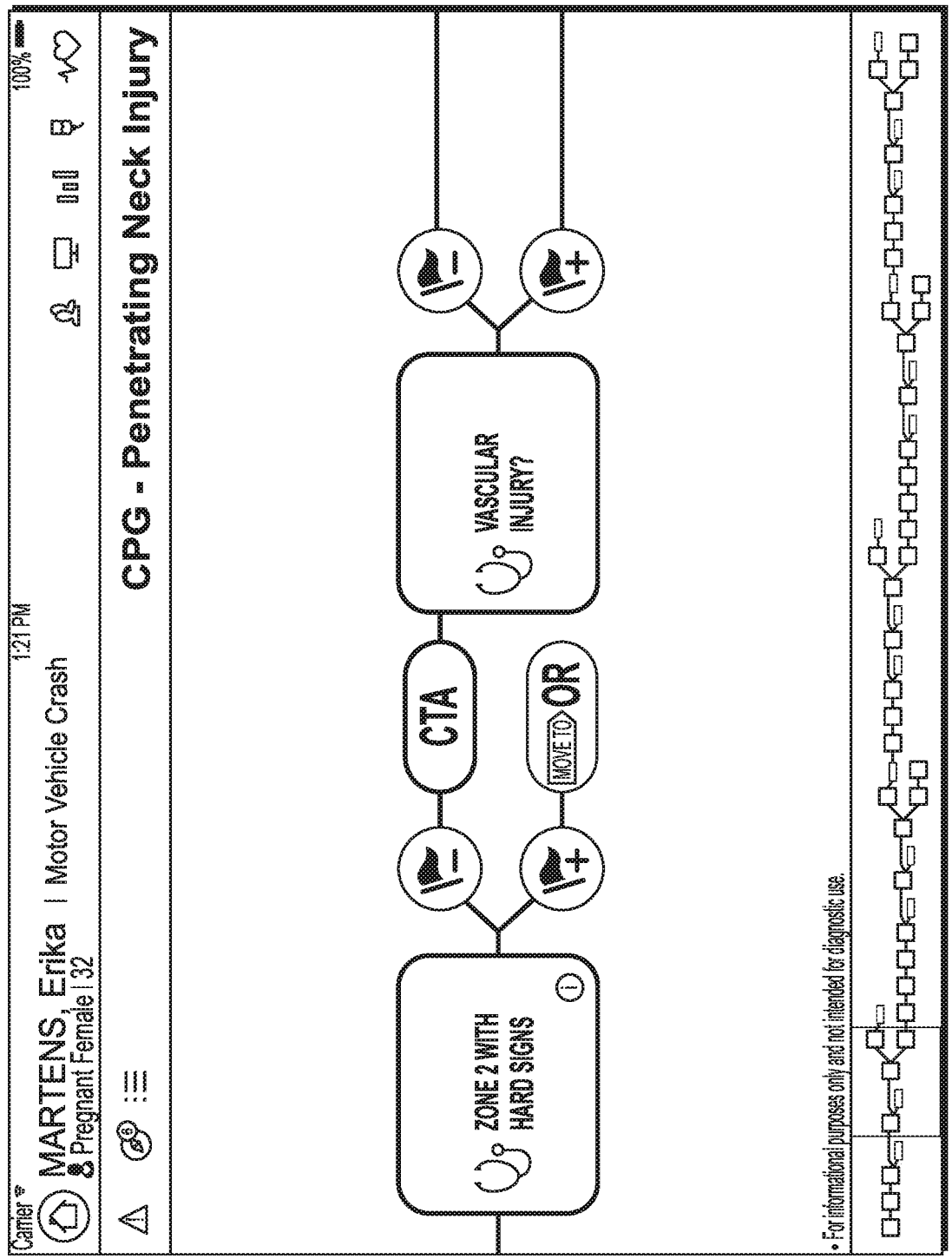
Figure 13C:
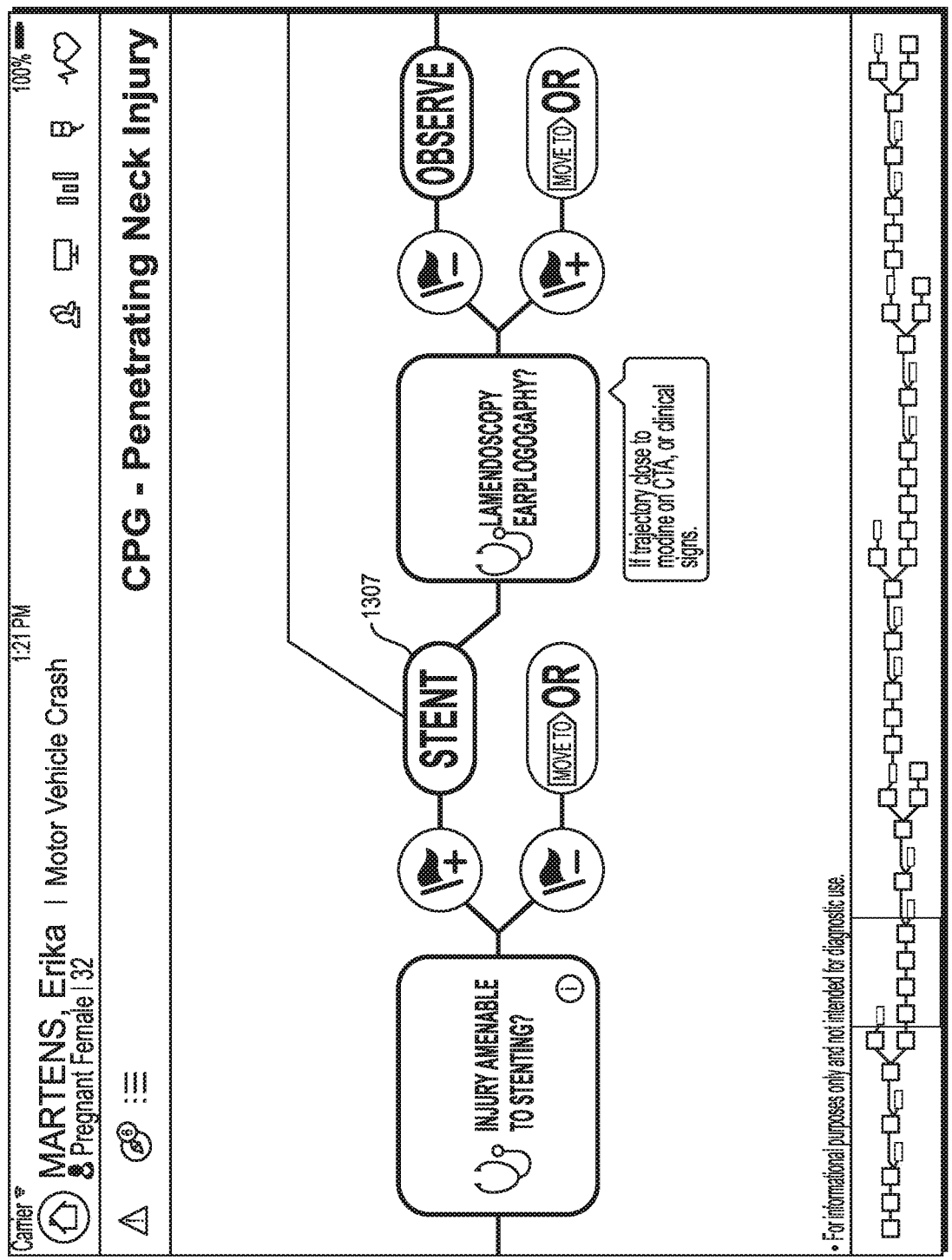
Figure 19:
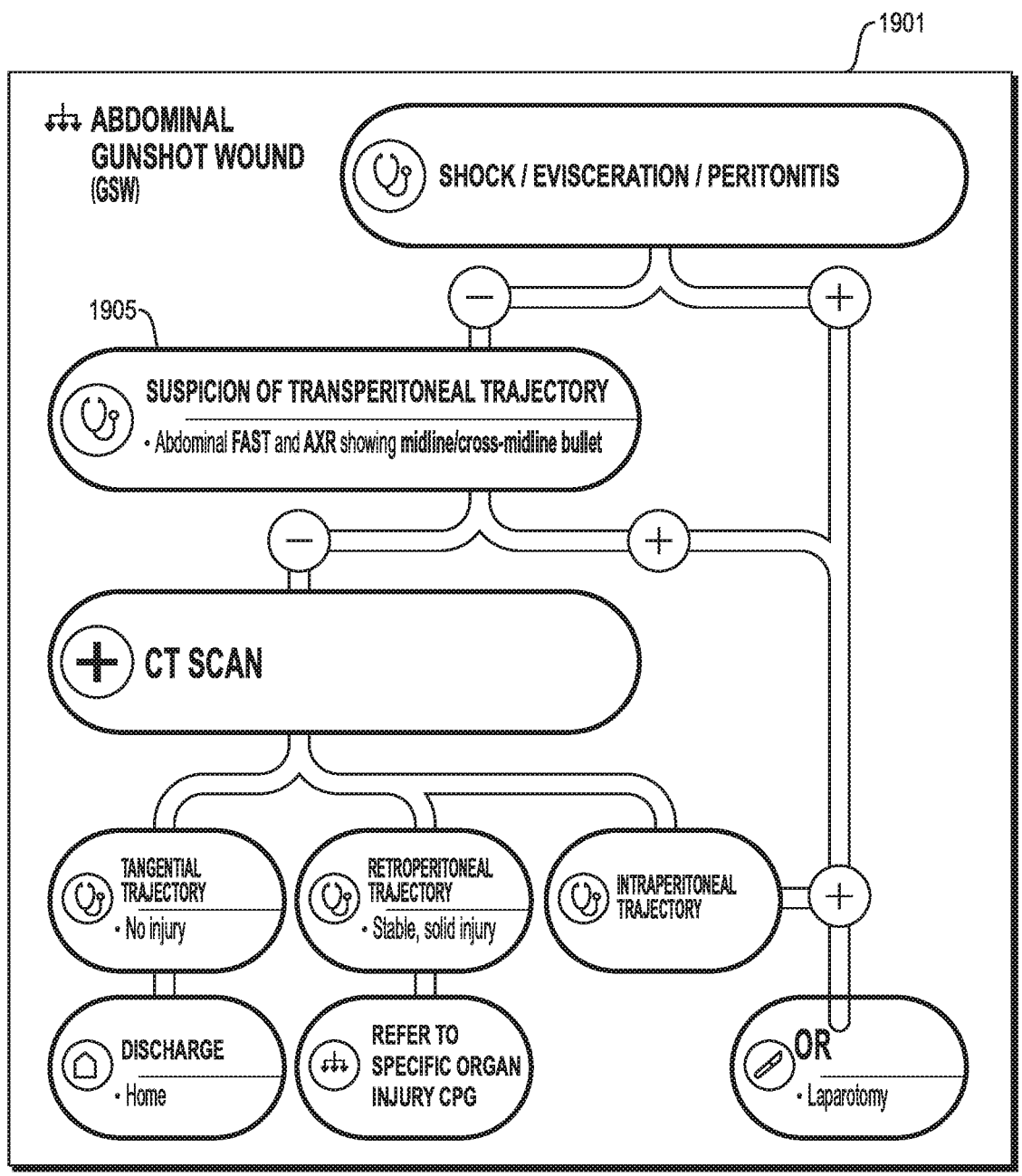
FIG. 19 depicts an illustrative screen depicting a clinical practice guidelines for a gunshot wound according to some embodiments.

FIGS. 13A-13C depict illustrative clinical practice guideline process displays according to a first embodiment. As shown in FIG. 13A, a clinical practice guideline process display may be presented with various steps or processes of a particular clinical practice guideline. In some embodiments, selection of an object (for example, "Penetrating Neck Injury" box) may operate to present further information 1302 about the particular object (for example, information regarding the types of neck injuries, typical symptoms, etc.). In some embodiments, the clinical practice guideline process display may include reference imagery 1303 associated with the clinical practice guideline. The clinical practice guideline process display may indicate which dashboard screen, category, or clinical practice guideline page a user was on for the particular clinical practice guideline, for instance, by using a background color coordinating therewith (e.g., a purple background for a Review category screen). A zoom map 1304 may present the various steps of the clinical practice guideline through selectable objects that may be selected to navigate to a particular step or section of the clinical practice guideline. Selection of a decision point 1305 may be configured to navigate to another page of the clinical practice guideline to continue with the clinical practice guideline process. If a patient transfer has occurred during the clinical practice guideline process, a transfer object 1306 may be selected to automatically generate a timestamp when the transfer occurred. As shown in FIGS. 13A and 13C, selection of a treatment object 1307 may generate a timestamp and record the treatment event. FIG. 19 depicts an illustrative screen 1901 depicting a clinical practice guideline 1905 for a gunshot wound according to some embodiments.

Figure 14A:
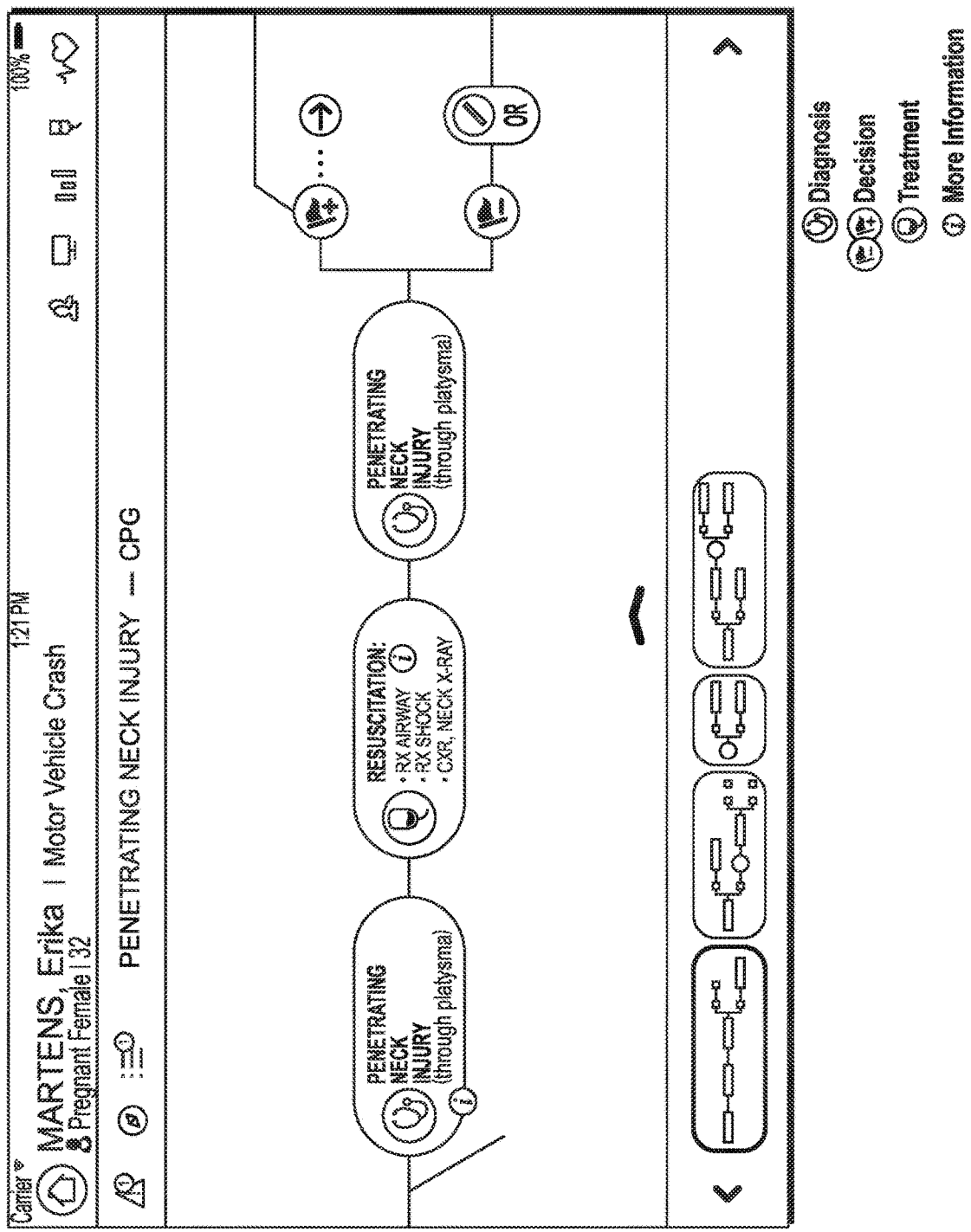
FIGS. 14A-14C depict illustrative clinical practice guidelines process displays according to a second embodiment.
Figure 14B:
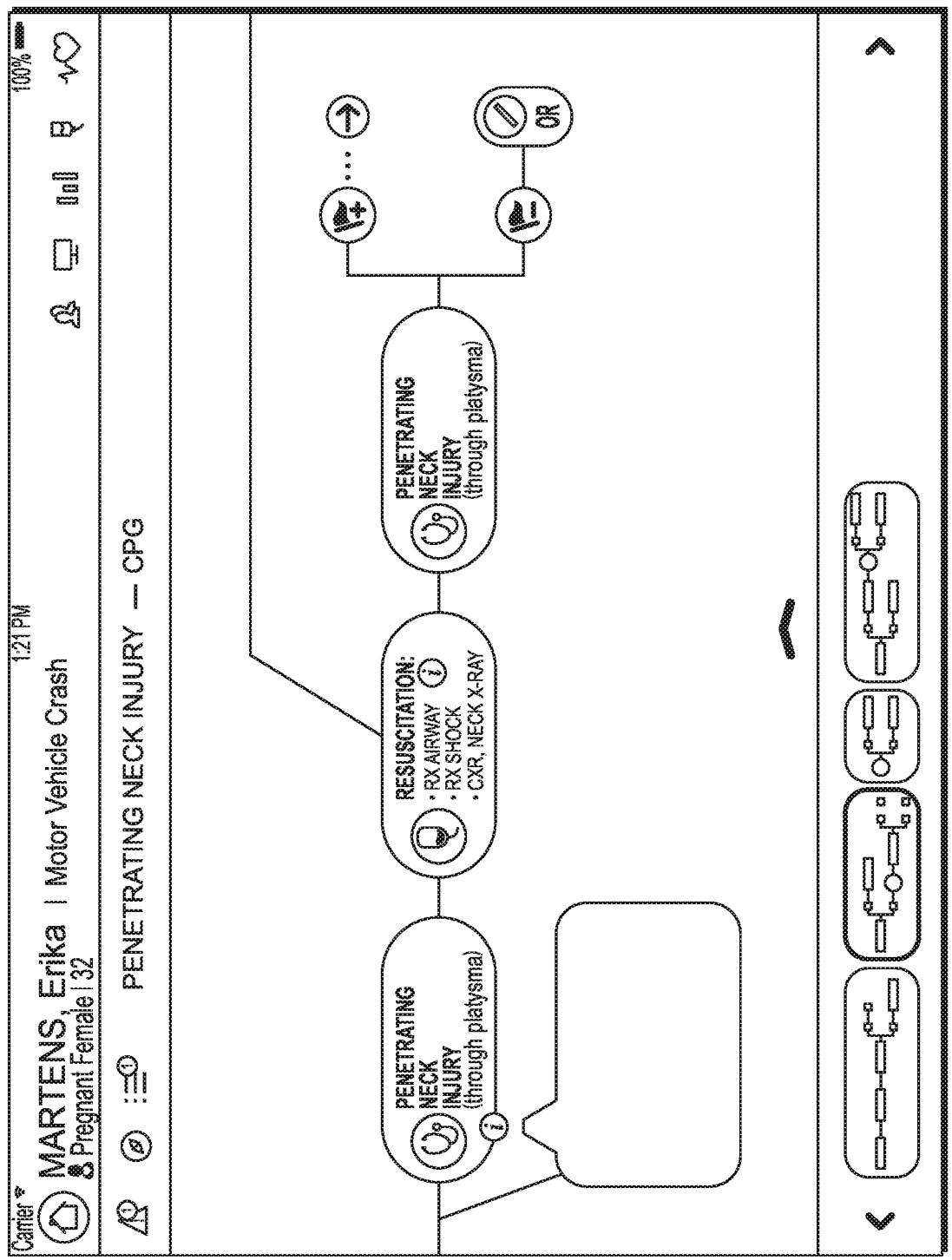
Figure 14C:
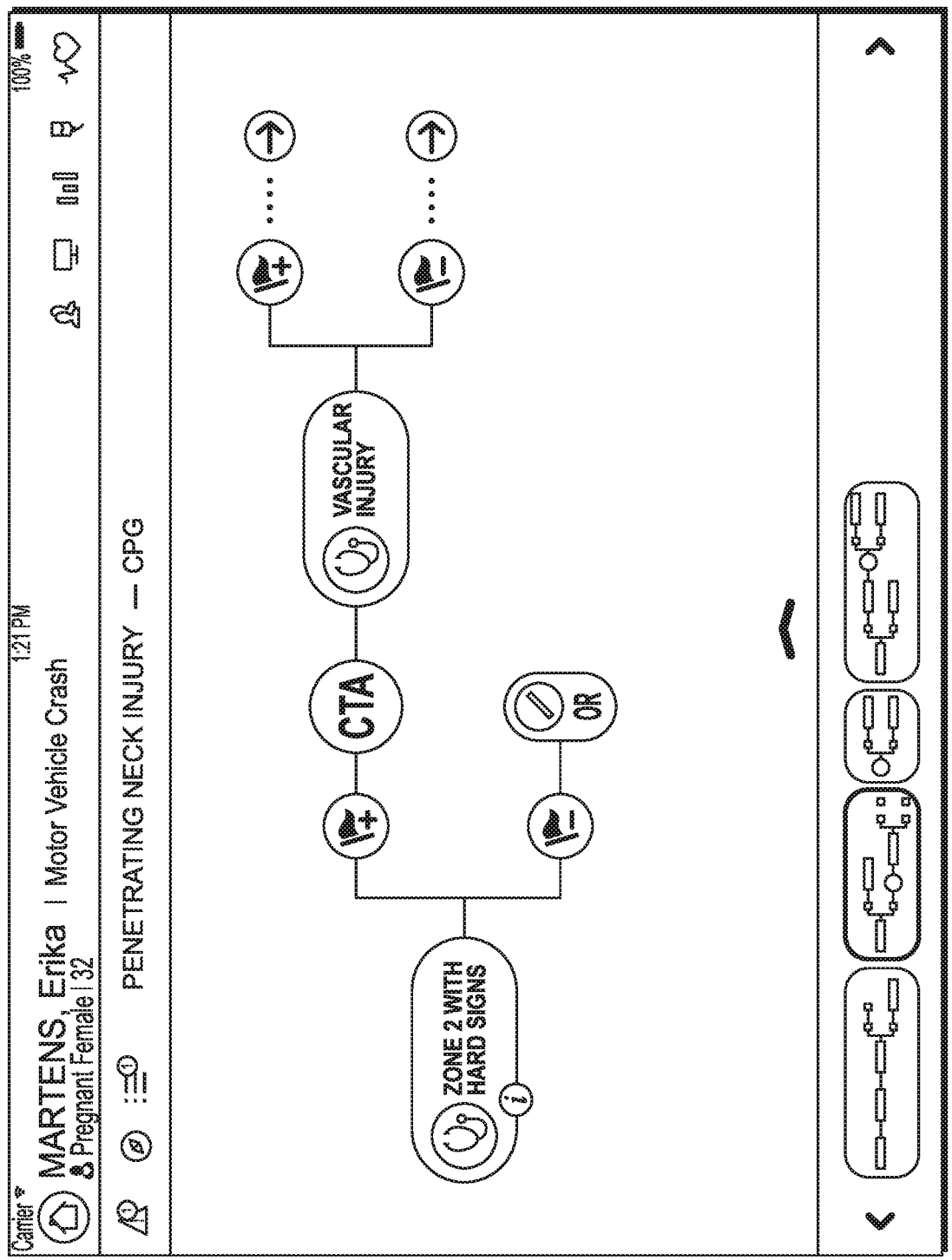

FIGS. 14A-14C depict illustrative clinical practice guideline process displays according to a second embodiment. In the clinical practice guideline process displays depicted in FIGS. 14A-14C, colors and icons may change for each category of the guideline. In some embodiments, the clinical practice guideline process displays may be configured to use color only for important and/or urgent decisions and/or actions (e.g., decisions 1305 or transfers 1306).

Figure 15A:
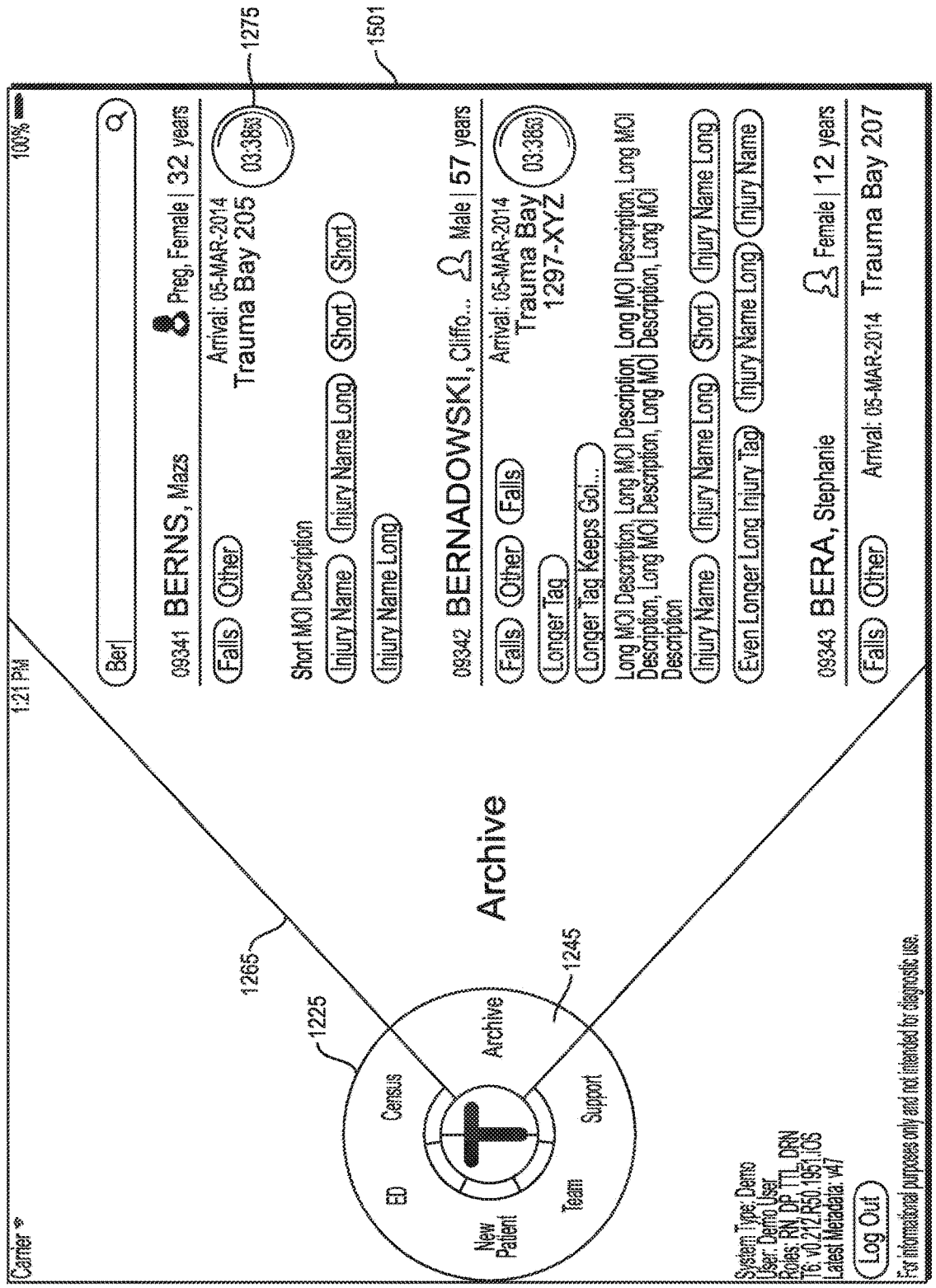

FIGS. 15A-15E depict various illustrative GUI screens that may be included in the health information application in addition and/or corresponding to screens, windows, GUIs, or the like described hereinabove. FIG. 15A depicts an illustrative archive screen 1501 according to some embodiments. The archive screen 1501 may be configured to present archive or historical information relating to patients and/or patient treatment.

In some embodiments, when a user logs into or otherwise access a system screen, the user may be presented with a navigation object, such as navigation object 1225. In some embodiments, the navigation object 1225 may include a set of selection areas 1245 configured based on default settings, user preference, historical information, location of computing device (for instance, a different set of selection areas may be used if the computing device is located in an emergency room, while another set of selection areas may be used if the computing device is located in an operating room). In some embodiments, the selection areas may include, without limitation, a "Welcome & Support" selection area, a "Team" selection area, an "Add Patient" selection area, an emergency department (ED) selection area, a "Census" selection area, and/or an "Archive" selection area.

Figure 15B:
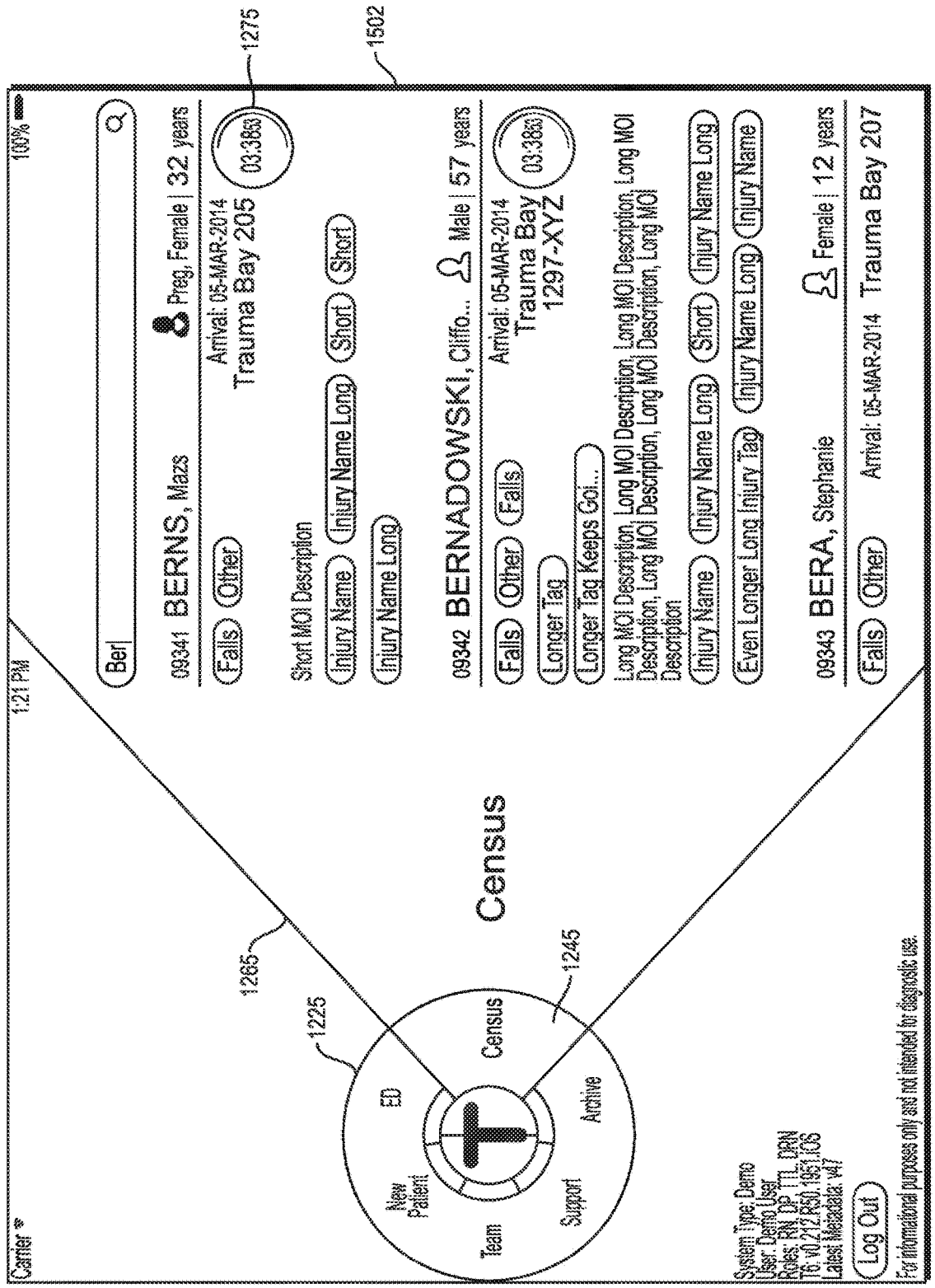

In reference to FIG. 12A, FIG. 15A depicts a navigation object 1225 with an active archive selection area 1245. Selection of the archive selection area 1245 causes an archive information object 1265 to be presented on the archive screen 1501 with various information elements 1275 displayed thereon. FIG. 15B depicts an illustrative census screen according to some embodiments. The census screen 1502 may be configured to provide information about patients receiving treatment at an entity, such as a healthcare facility and/or ER thereof. As shown in FIG. 15B, selection of the census selection area 1245 on the navigation object 1215 causes a census information object 1265 to be presented on the census screen 1502 with various information elements 1275 displayed thereon. In some embodiments, the census platform may include a dynamic document that is filled directly from the clinical documents (healthcare information) that may be configured to keep track of injuries and other issues and to facilitate seamless handover of the patient between treatment teams.

Figure 15C:
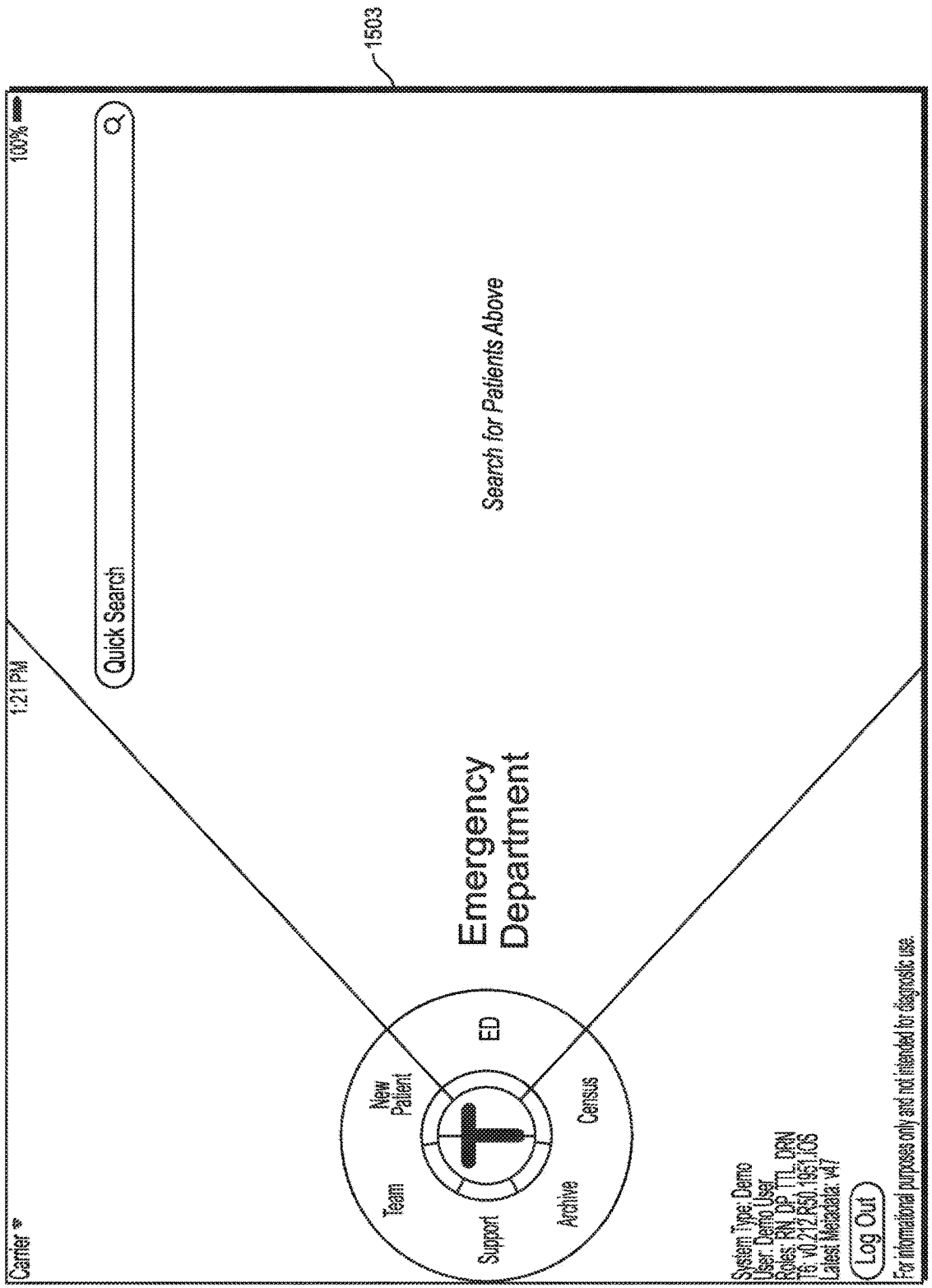

FIG. 15C depicts an illustrative emergency department screen according to some embodiments. The emergency department screen 1503 may be configured to provide information about the emergency department of an entity, such as patients being treated, medical staff and medical professionals, beds, wait times, or the like. In some embodiments, once patients are admitted in the emergency department via the system, their record may be transferred or otherwise associated with the Census platform (see FIGS. 23A-23E).

FIG. 15D depicts an illustrative team and roles screen according to some embodiments. The team and roles screen 1504 may be configured to provide information about a team of medical professionals and staff presently and/or previously treating patients and/or providing administrative or other support. Each team member may be listed along with their role and any other relevant information, such as contact information, expertise, education, experience, or the like. The team members may be filtered 1505 using various criteria, such as by area of expertise (e.g., hand surgery), category (e.g., physicians, nurses, or the like), availability (e.g., team members on-site, call schedules, shift assignments, or the like), or the like. A user may select team members objects 1509 to obtain further information and/or to designate members for a team. In some embodiments, selected team member objects 1509 may be highlighted, for instance, using different colors, font, background, or the like to make the team members more prominent for efficient recognition of an assembled team.

Figure 15E:
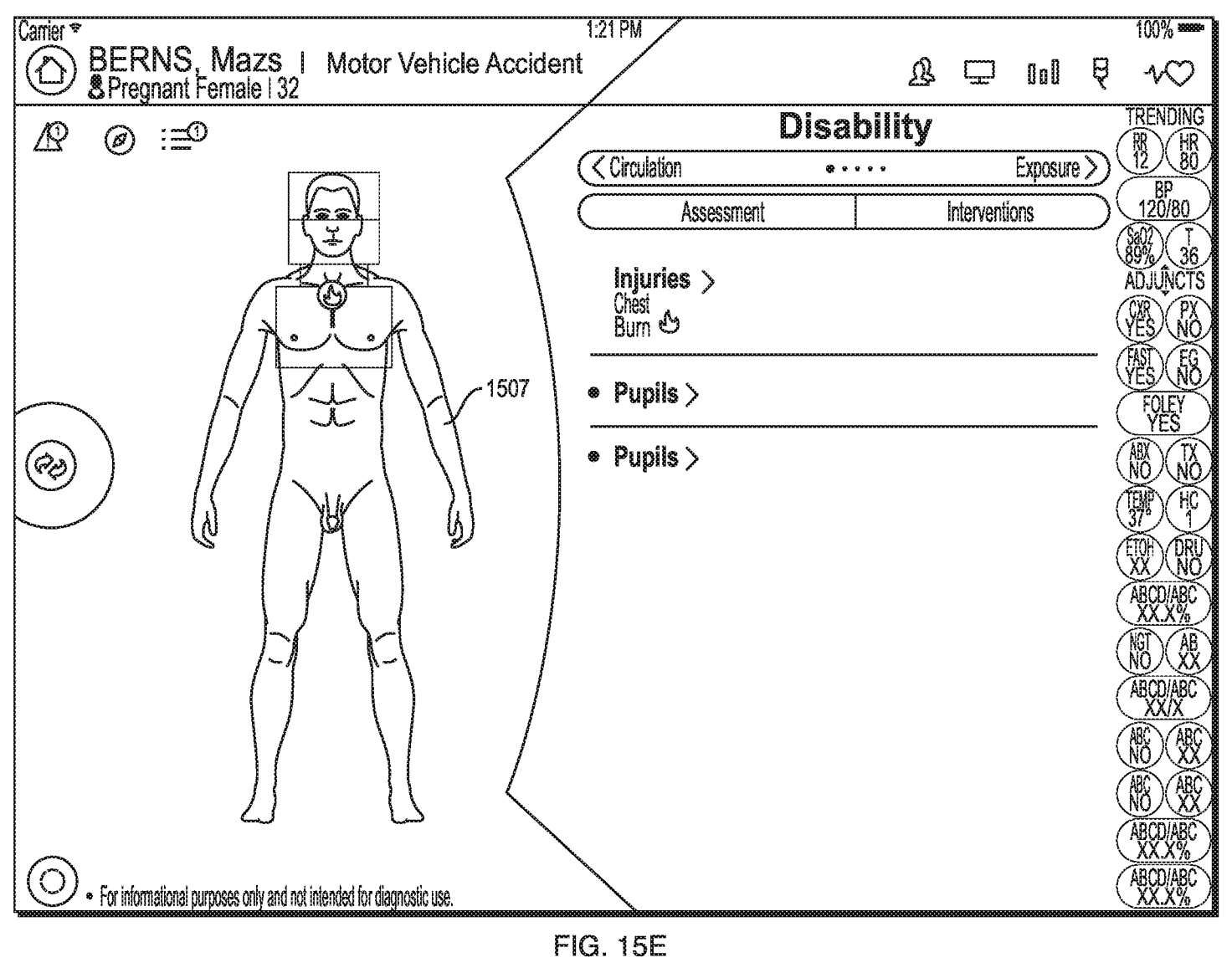
Figure 22:
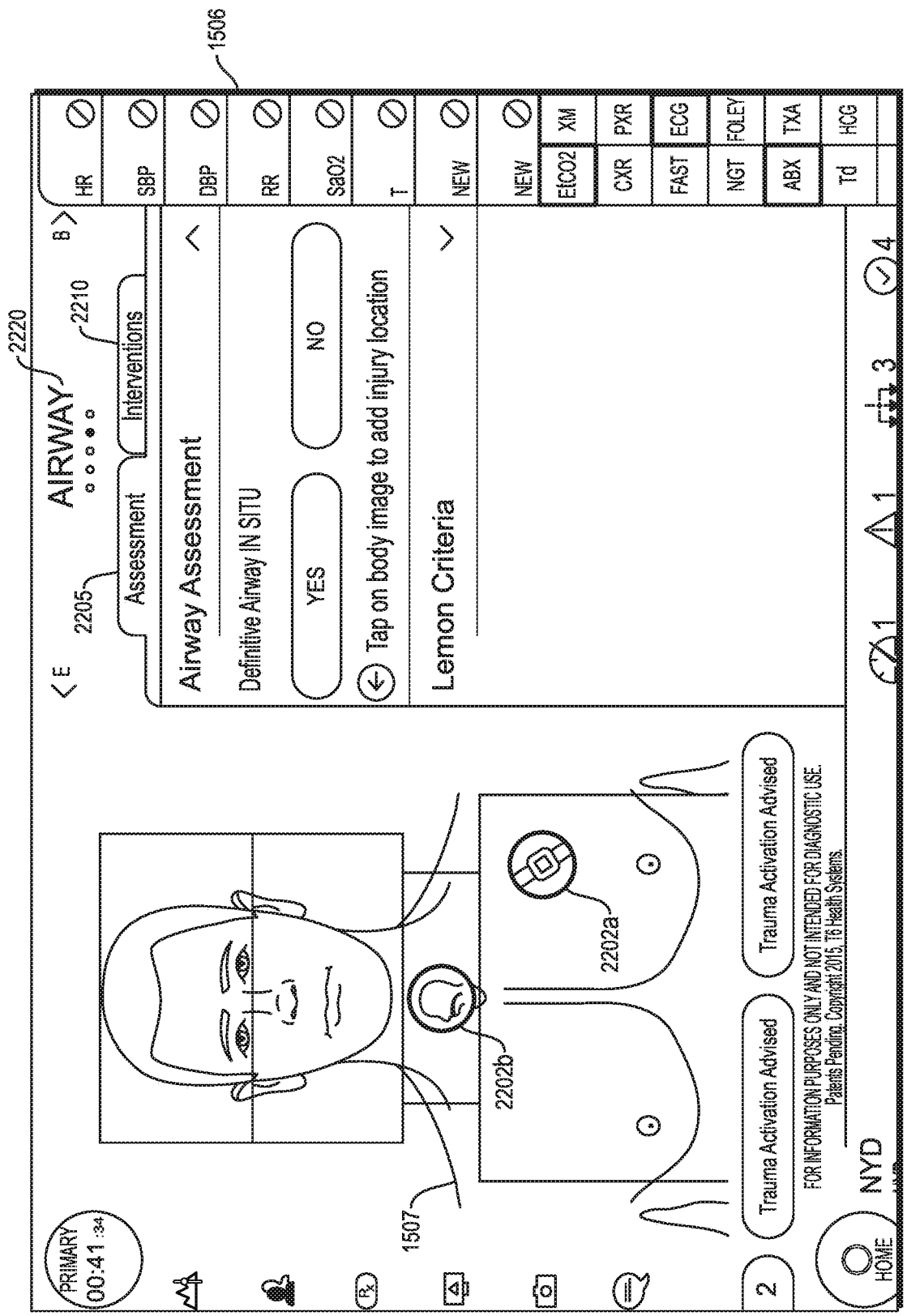
FIG. 22 depicts an illustrative trauma representation screen according to some embodiments.

FIG. 15E and FIG. 22 depict an illustrative trauma representation screen according to some embodiments. The trauma representation screen 1506 may include a patient representation 1507 ("trauma man") that may be configured to allow injuries or other traumas to be directly represented on a virtual patient. In some embodiments, various portions or segments of the patient representation 1507 may be selected and injuries and characteristics thereof specified for the particular area. For instance, a user may select the chest of the patient representation 1507, a designated portion thereof, and or some other selection object and input an injury associated with the chest and other information associated therewith (for instance, the severity of the injury, details of the injury, or the like). In some embodiments, selection of the chest of the patient representation 1507, the designated portion thereof, and or the some other selection object may present information previously entered regarding the injury associated with the chest. In this manner, information may be input using the patient representation 1507 and/or some other portion of the trauma representation screen 1506 and may be retrieved for viewing at a later time. In some embodiments, the symptoms and signs of the patient representation 1507 may be a trigger for generating or making accessible alerts, clinical practice guidelines, and checklists.

As shown in FIG. 22, the patient representation 1507 may include various information objects 2202a, 2202b, for example, relating to injuries, patient characteristics, trauma event characteristics (for instance, was a vehicle accident patient wearing a seatbelt 2202b). In some embodiments, the information objects 2202a, 2202b may be selectable. For example, selection of the airway information object 220a may cause an airway region 2220 to appear on the trauma representation screen 1506 to allow a medical professional to view and modify information relating thereto. For instance, the airway region 2220 may include airway assessment 2205 information objects and interventions 2210 information objects.

Figure 16A:
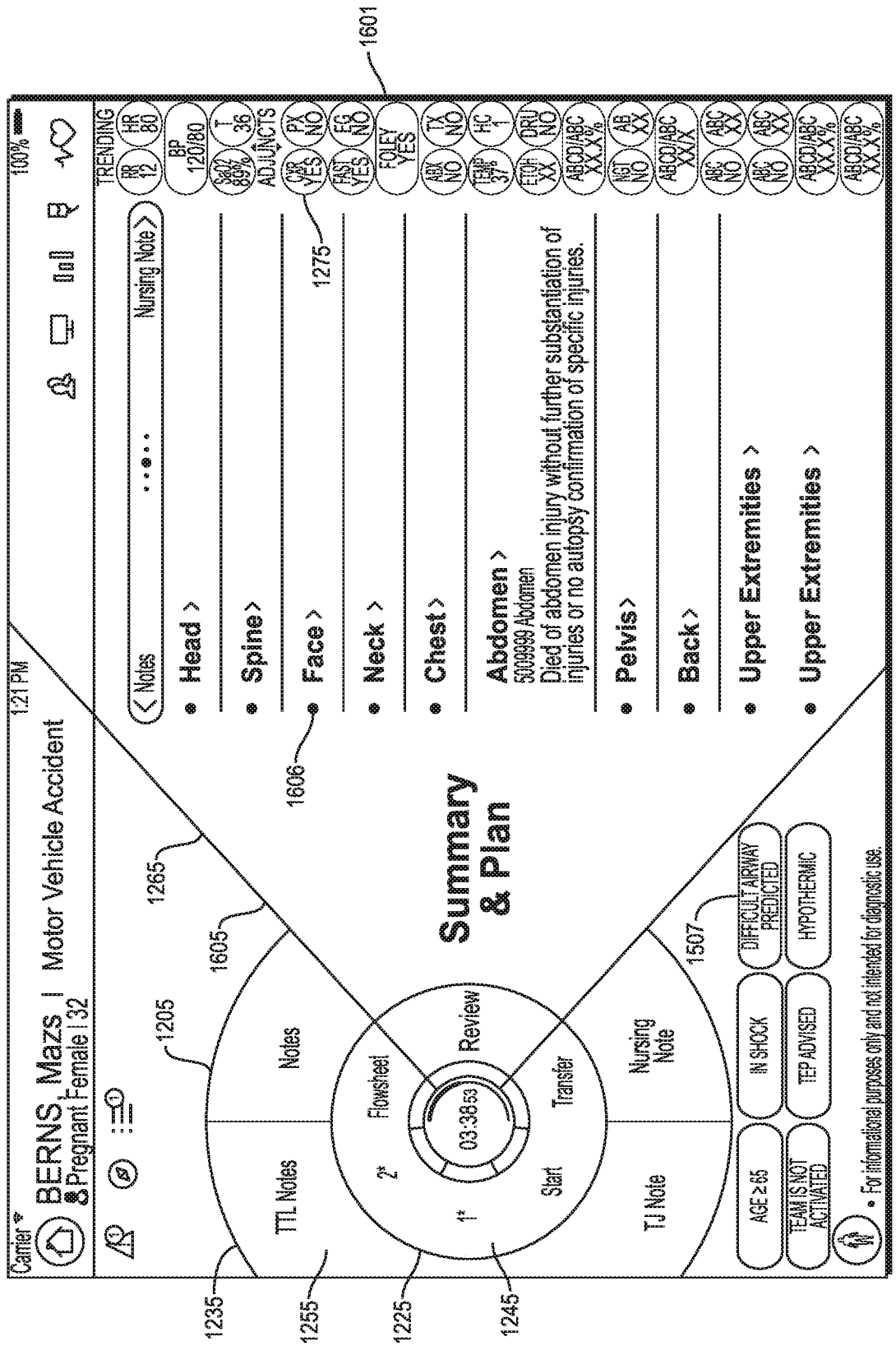
FIGS. 16A and 16B depict illustrative review category screens according to some embodiments.
Figure 16B:
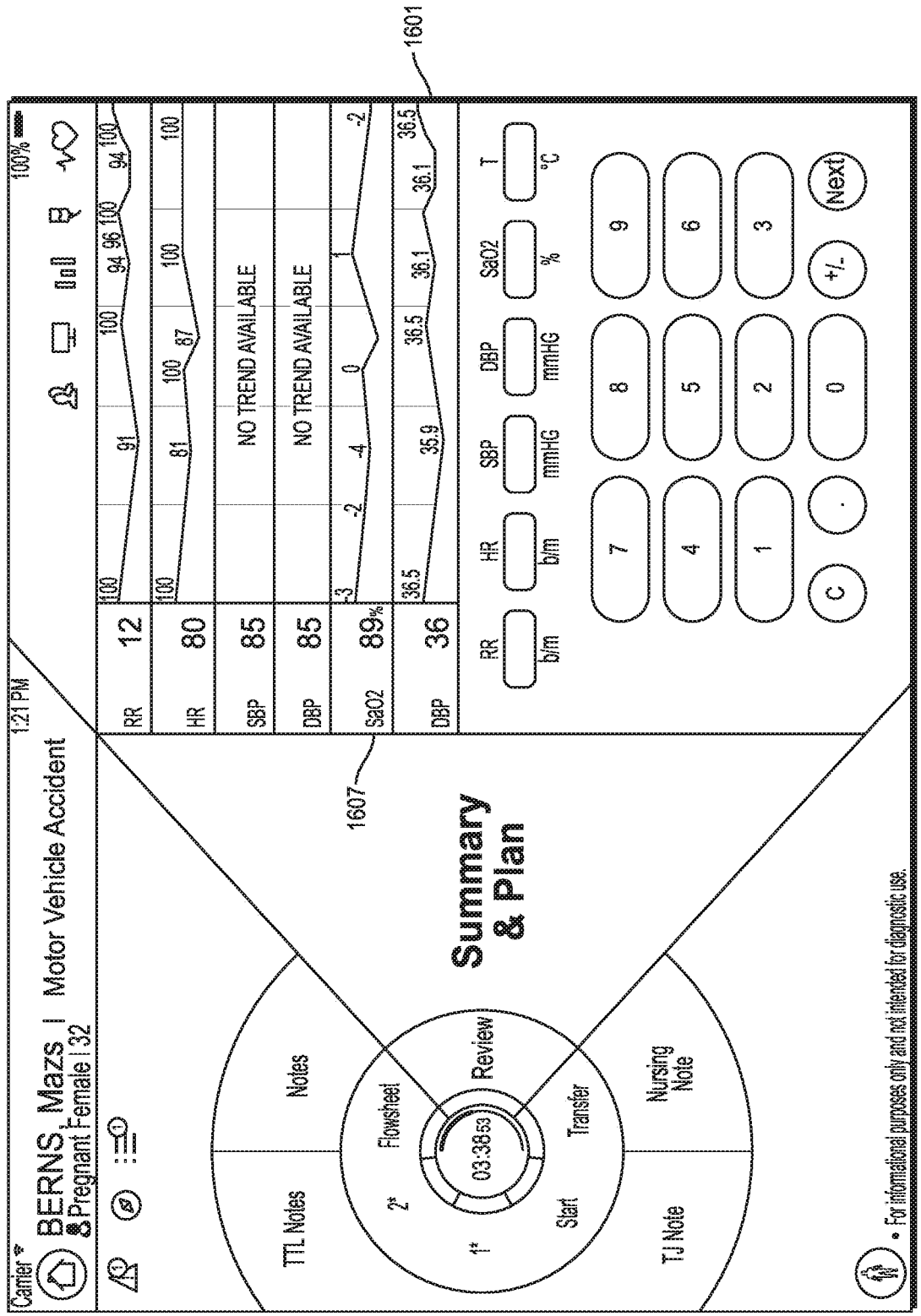

FIGS. 16A and 16B depict illustrative review category screens according to some embodiments. FIG. 16A depicts a review screen 1601 with a summary and plan display (or "wedge") 1605 (for instance, as an information object 1265) that may include summaries and/or plans for various portions of the human body. The review screen 1601 may include elements 1606 for specifying certain details regarding the patient and/or treatment thereof. In some embodiments, elements 1606 may be selectable to cause information relating to a particular element (for instance, the face or neck) to be presented on the screen 1601. In reference to FIG. 12A, FIG. 16A depicts a navigation object 1215 with a primary navigation level 1225 and a secondary navigation level 1235. The selection of the review selection area 1245 causes the selection areas 1255 associated with a review process to be displayed on the secondary navigation level 1235. Activation of the summary & plan selection area 1255 causes a summary & plan information object 1265 to be presented on the review screen 1601 with various information elements 1275 displayed thereon. FIG. 16B depicts a review screen 1601 with an associated trend display 1607 (for instance, as depicted in FIG. 12G).

Figure 17A:
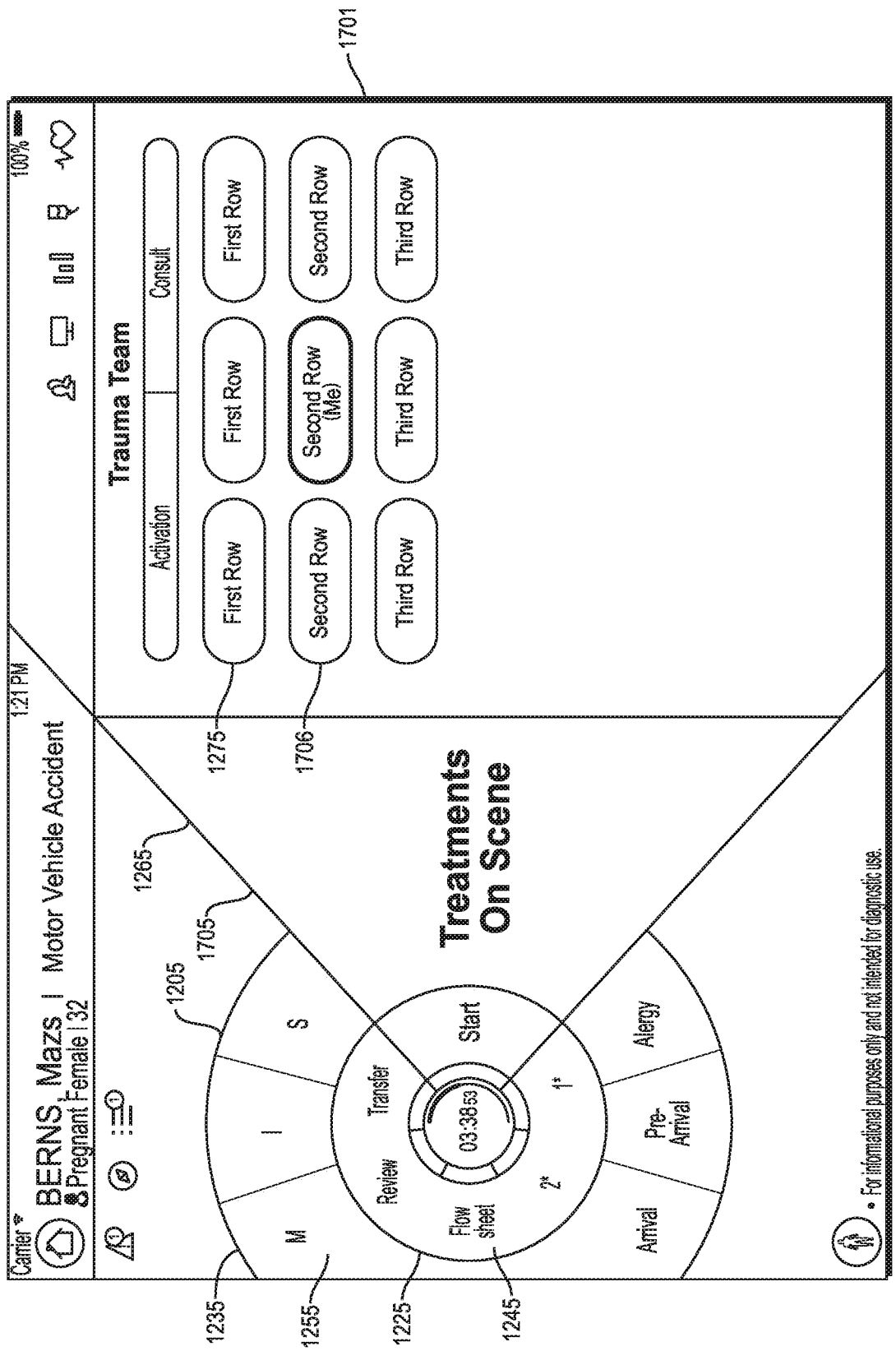
FIGS. 17A-17E depict illustrative start category screens according to some embodiments.

FIGS. 17A-17E depict illustrative start category screens according to some embodiments. As shown in FIG. 17A, a start screen 1701 may include a treatments on scene (TOS) display or wedge 1705. The TOS wedge 1705 may display a trauma team 1706 for treating a patient. In reference to FIG. 12A, FIG. 17A depicts a navigation object 1215 with a primary navigation level 1225 and a secondary navigation level 1235. The selection of the start selection area 1245 causes the selection areas 1255 associated with a start process to be displayed on the secondary navigation level 1235. Activation of the treatments on scene selection area 1255 causes a treatments on scene object 1265 to be presented on the start screen 1701 with various information elements 1275 displayed thereon.

Figure 17B:
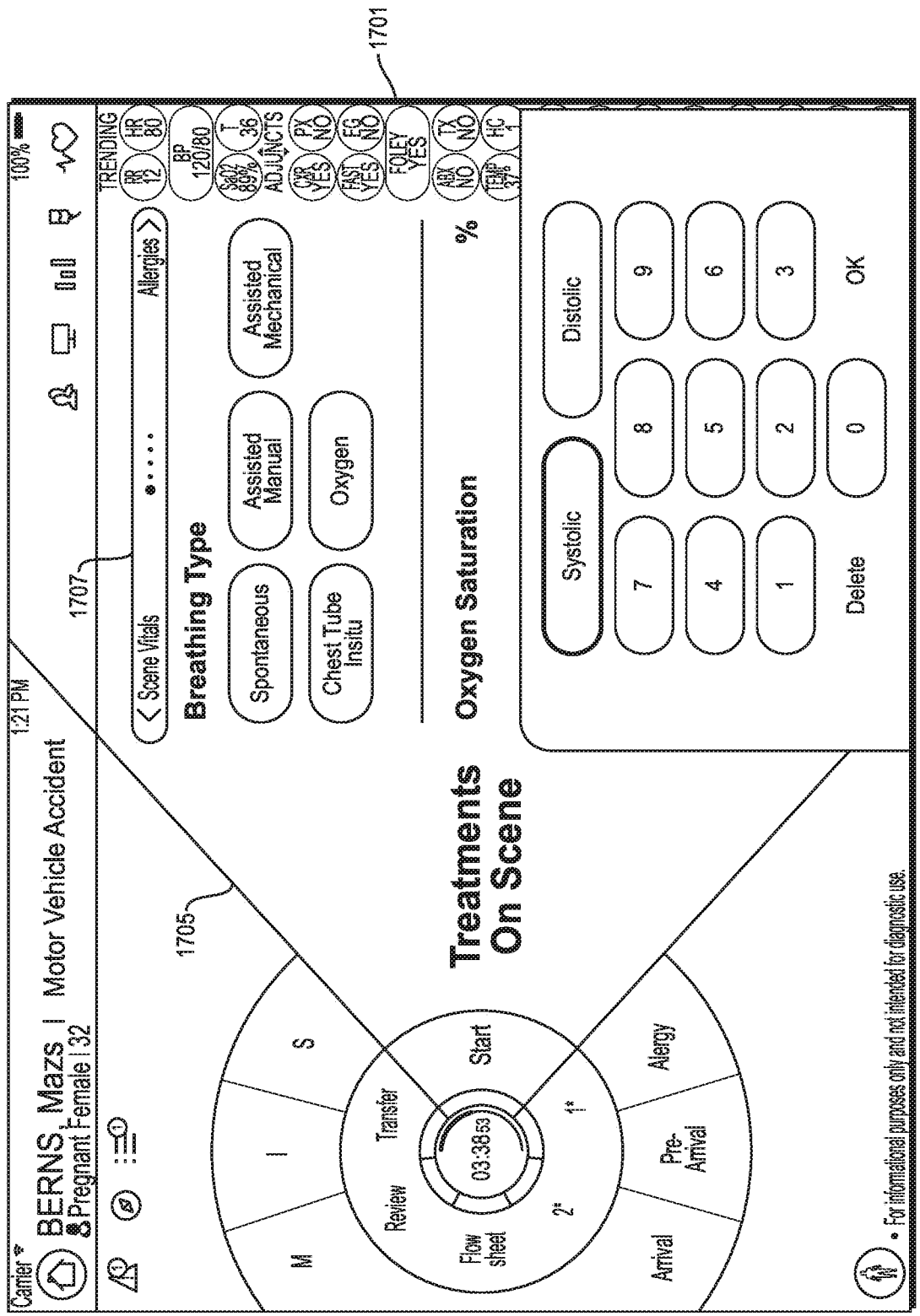
Figure 17C:
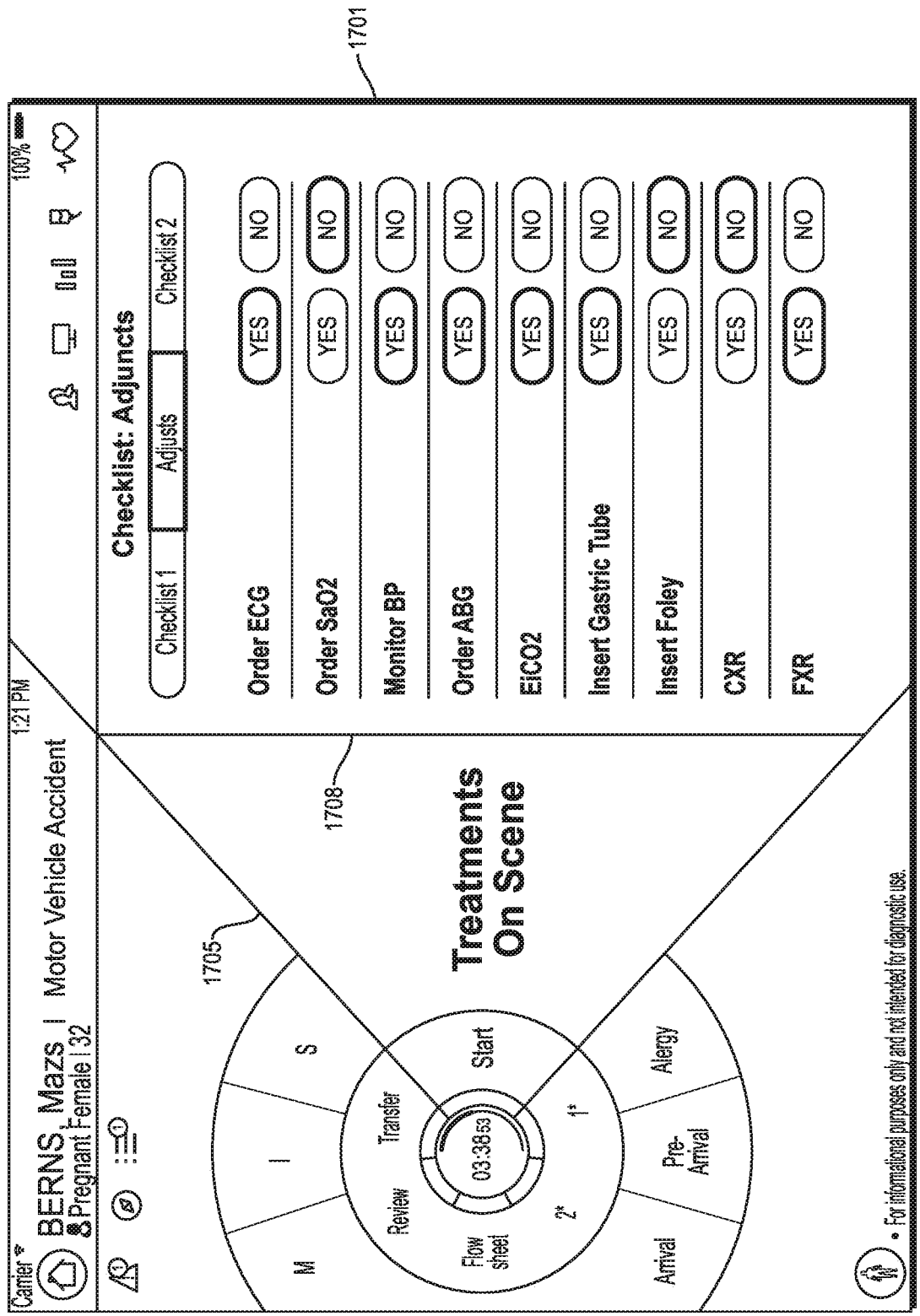
Figure 17D:
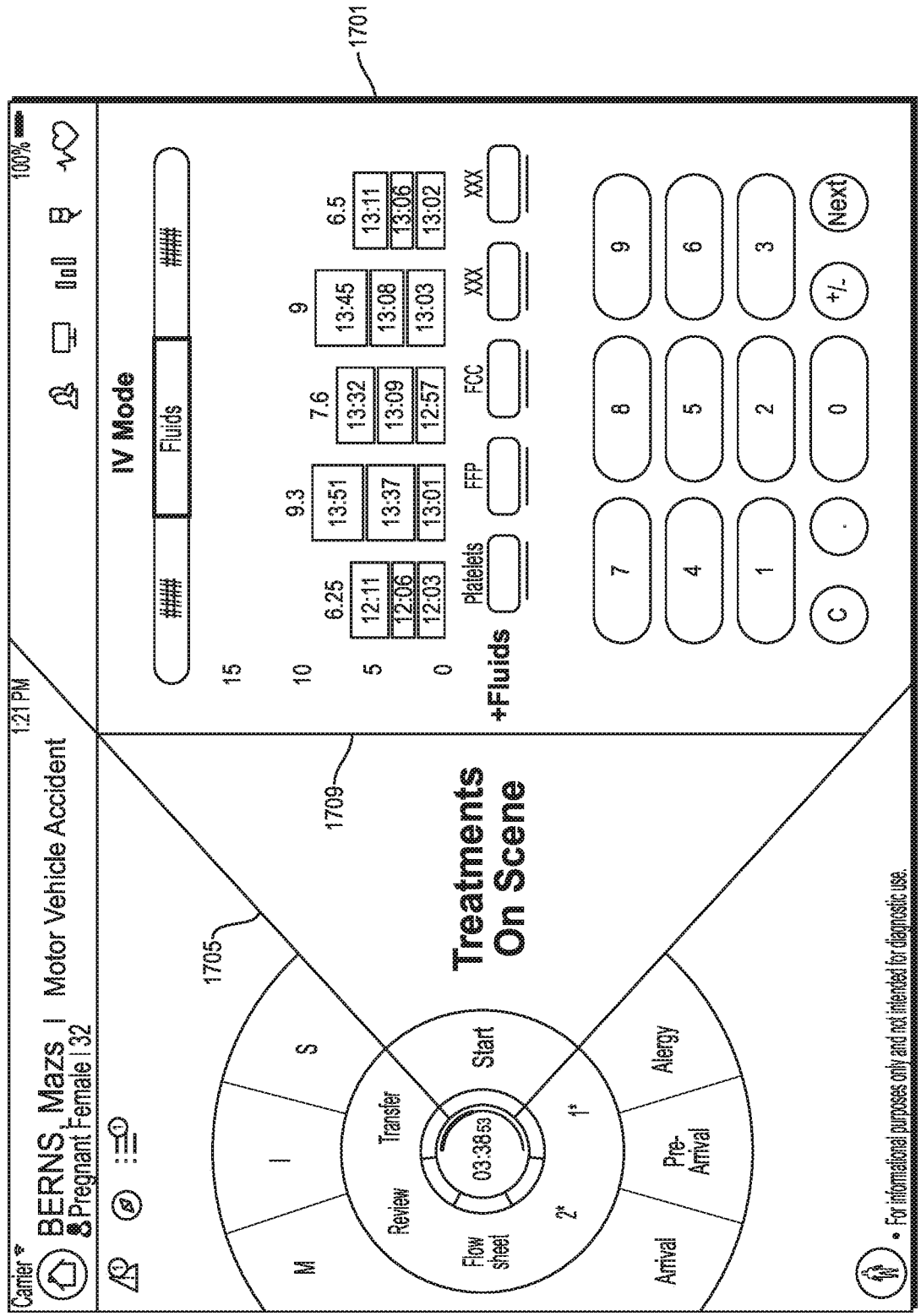
Figure 17E:
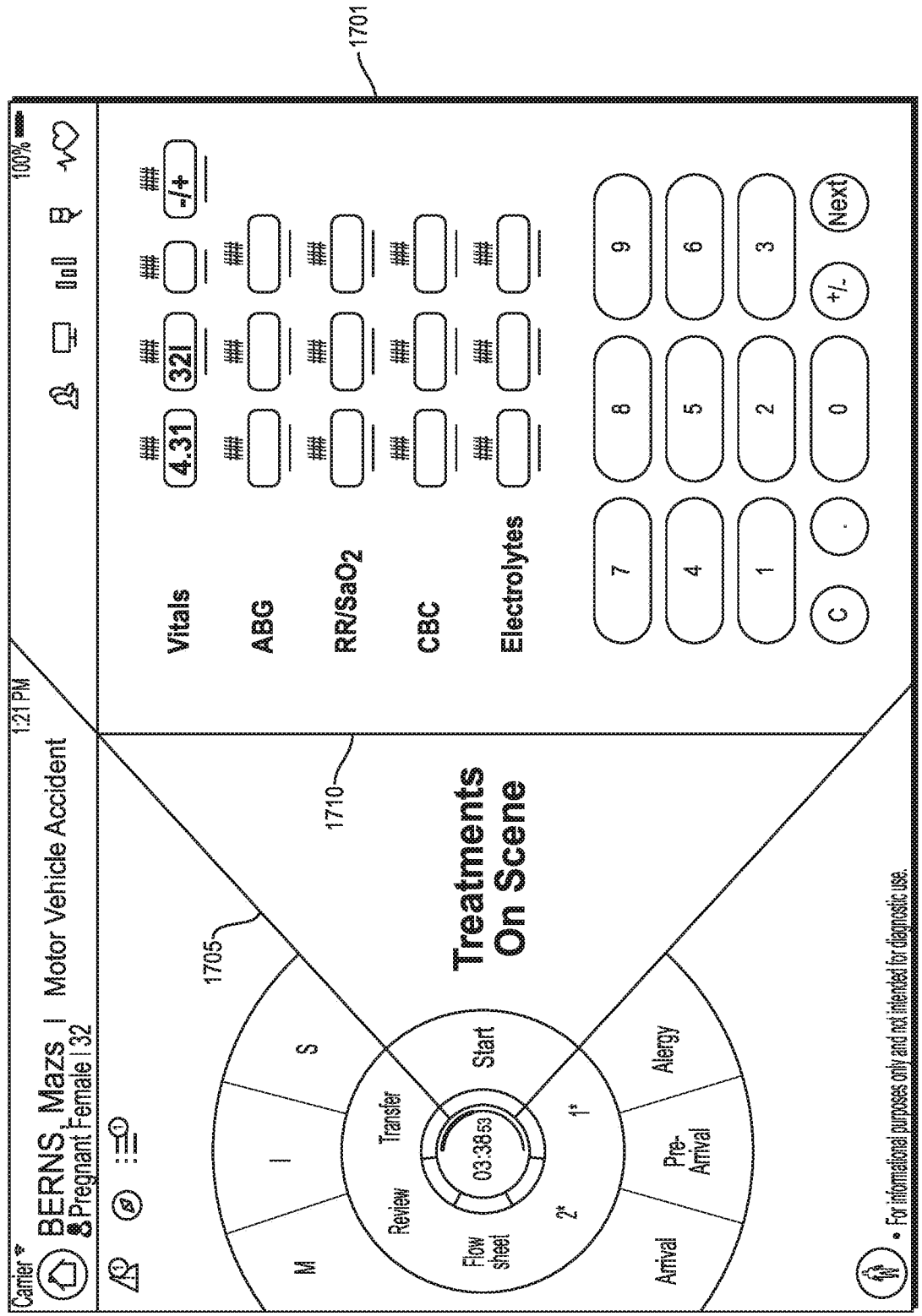

As shown in FIG. 17B, the TOS wedge 1705 may present patient's vitals information 1707, such as breathing type and oxygen saturation, or other related information (for example, allergies). The TOS wedge 1705 may provide for the viewing and/or entry of data. FIG. 17C depicts a TOS wedge 1705 that includes a checklist 1708, such as an adjuncts checklist. As shown in FIG. 17D, a TOS wedge 1705 may be configured to present fluid information 1709 for a patient. At least a portion of the fluid information 1709 may show the total fluids on a graph using individual boxes that indicate the time and the amount of fluid given at each fluid delivery event. FIG. 17E depicts a TOS wedge 1705 presenting a data entry screen 1710 for entering the vitals of a patient.

Figure 18A:
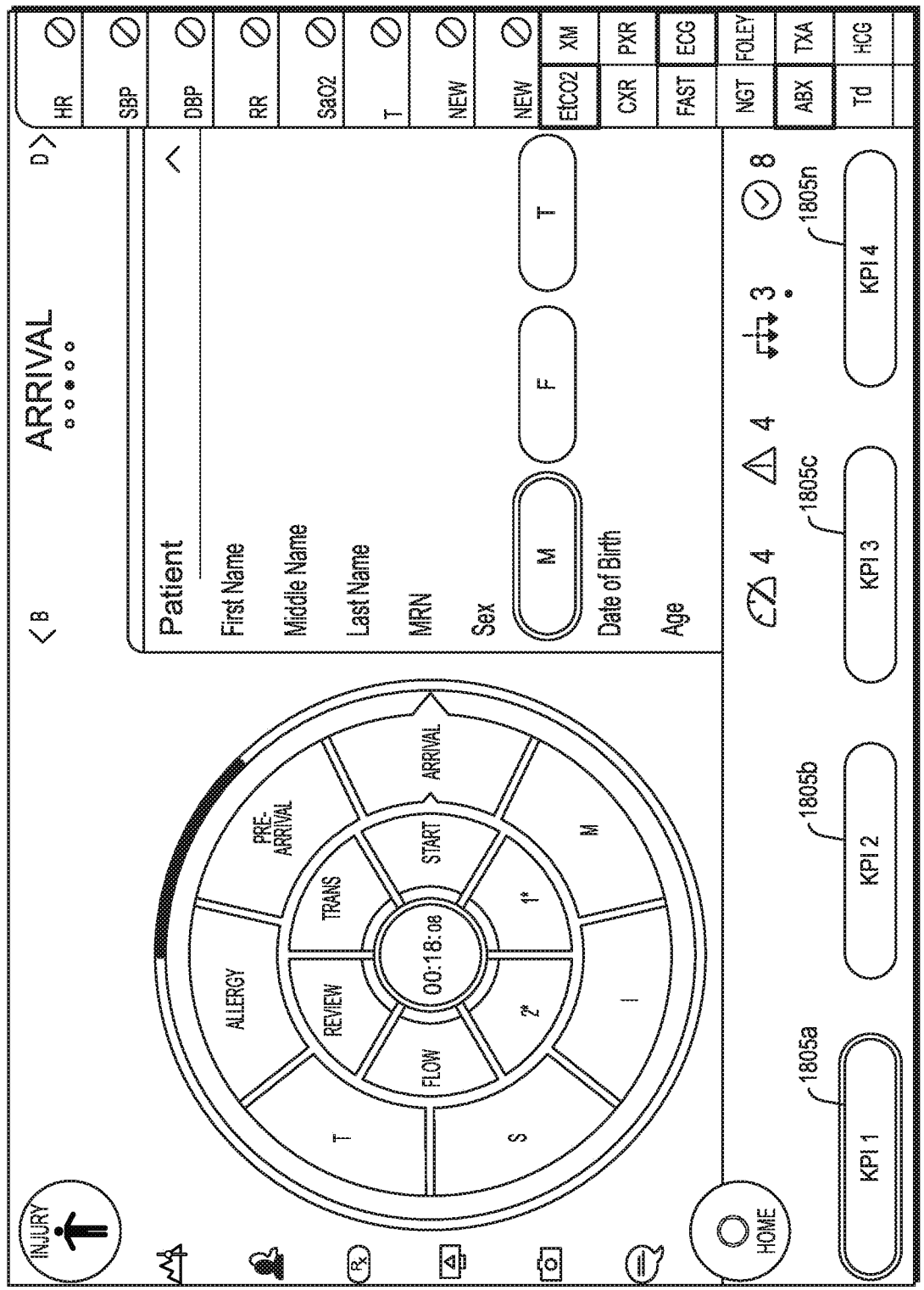
FIG. 18A depicts an illustrative key patient indicator screen according to some embodiments.

FIG. 18A depicts an illustrative screen 1801 that includes key patient indicators (KPIs) 1805a-n. In some embodiments, key patient indicators 1805a-n may include critical information elements regarding a patient, a trauma related to the patient, the physiological state of the patient, or the like. In some embodiments, the key patient indicators 1805a-n may include issues determined about a patient as the patient is going through an assessment, for example, by an emergency medical technician (EMT) team, and emergency room team, a surgical team, or the like. In some embodiments, the key patient indicators 1805a-n may be presented on the screen 1801 responsive to a user selection, such as a particular navigation selection area, a key patient indicator display object, or the like. In some embodiments, the key patient indicators 1805a-n may be presented on the screen 1801 by default if a key patient indicator exists. In some embodiments, the key patient indicators 1805a-n may be presented on the screen 1801 automatically due to a change in the key patient indicators, such as the addition of a new key patient indicator, a change in a key patient indicator (for instance, above or below a predetermined threshold), or the like. In some embodiments, an information element may be designated as a key patient indicator 1805a-n by a user. In some embodiments, the key patient indicators 1805a-n may be determined based on an analysis of the patient information, for example, based on historical information regarding key patient indicators used for other patients with similar physiological conditions, demographics, and/or medical conditions. In some embodiments, the key patient indicators 1805a-n may be determined based on an analysis of the patient information against a set of factors used to determine key patient indicators, for instance, a particular medical condition (for instance, broken vertebrae) may be a key patient indicator for a patient having a certain medical history and/or demographic information (for example, patients 65 years or older), but not for other patients with a different medical history and/or demographic information.

In some embodiments, the healthcare information application is able to generate or designate key patient indicators 1805a-n by recognizing and tagging key data elements, including combinations of data elements, that experienced clinicians often use to identify dangerous life threatening situations. The key patient indicators 1805a-n can be used by trauma teams as alerts about the potential severity of an injury, for instance, as a shorthand to communicate important issues quickly and efficiently and/or as triggers for immediate action. FIG. 18B lists illustrative and non-restrictive key patient indicators according to some embodiments.

Figure 21:
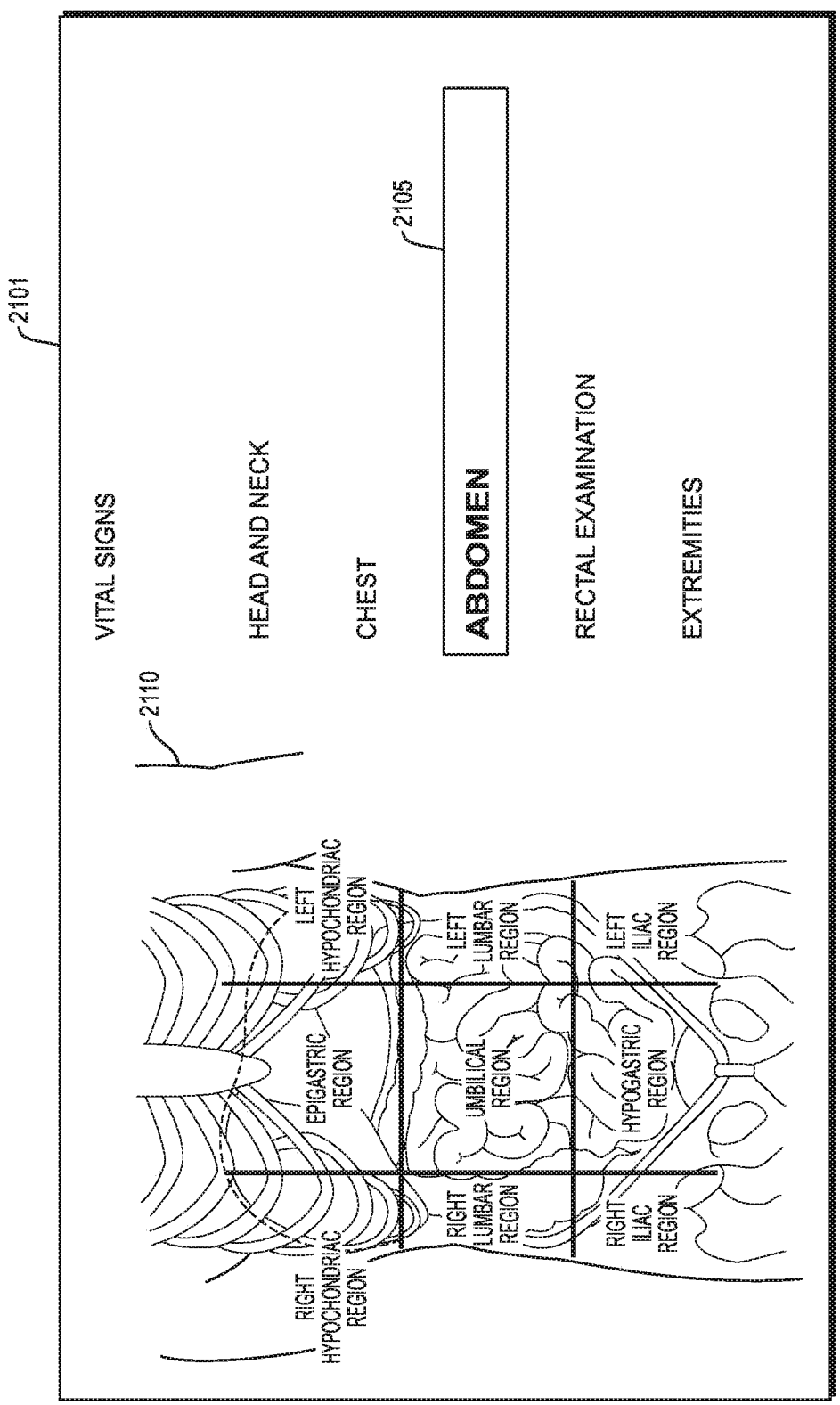
FIG. 21 depicts an illustrative screen for accessing various portions of the body of a patient via a graphical representation thereof.

FIG. 21 depicts an illustrative screen 2101 for accessing various portions of the body of a patient via a graphical representation 2110 thereof. As shown in FIG. 21, selection of a navigation object 2105, such as a navigation object for the abdomen, may cause the healthcare application to present a graphical representation 2110 of the corresponding portion of the body of the patient. In some embodiments, certain areas of the graphical representation 2110 may be selectable to input and/or access information relating thereto. For instance, a user may select the right lumbar region of the graphical representation to view healthcare information corresponding thereto.

Figure 23A:
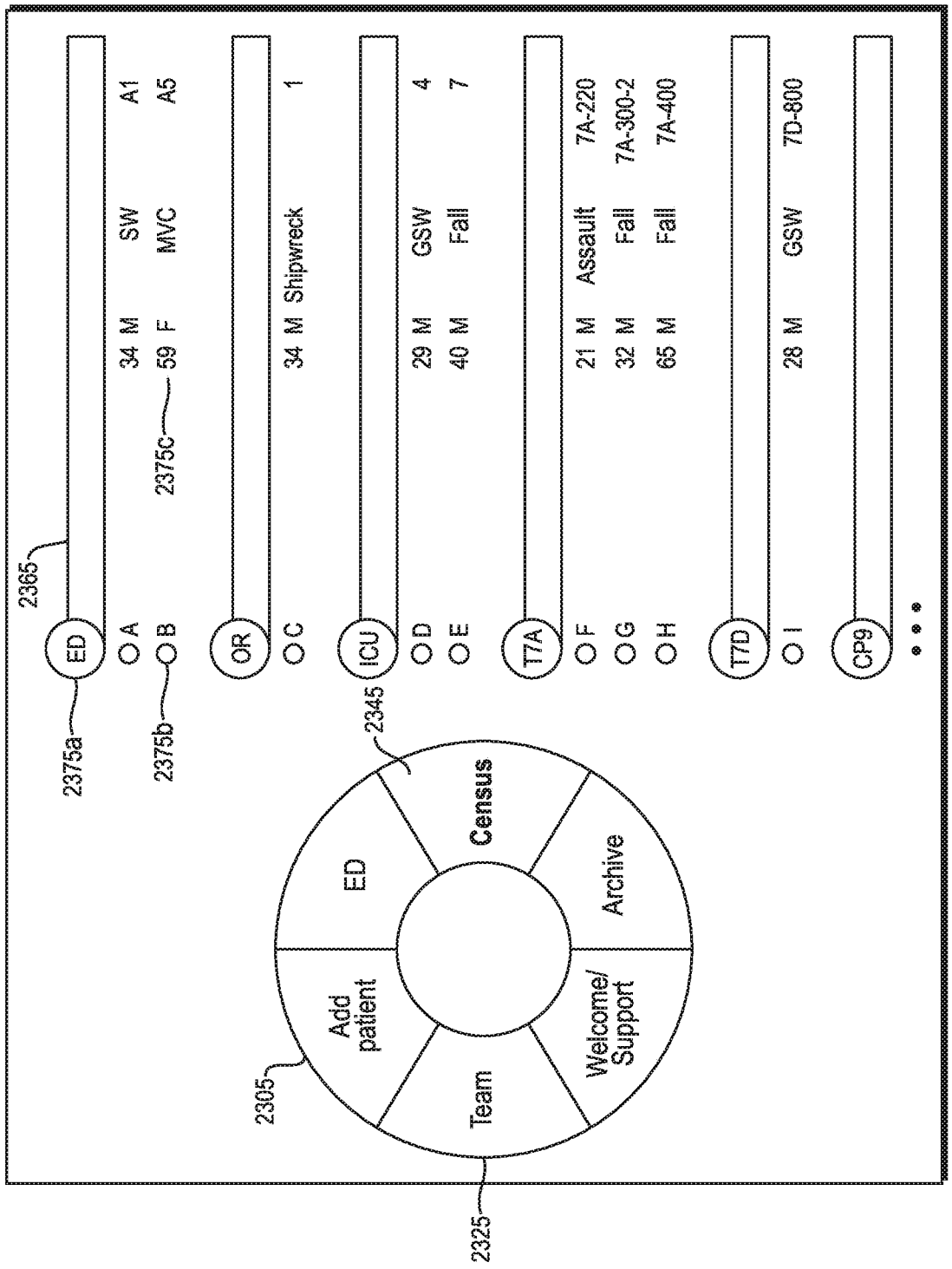
FIGS. 23A-23E depict an illustrative GUI platform according to some embodiments.

FIG. 23A depicts an illustrative GUI platform according to some embodiments. Multiple healthcare organizations, such as the World Health Organization, have identified timely and complete handover of a patient and patient information as a critical process in optimal patient care. In some embodiments, the census GUI platform may be configured as a mobile, electronic platform that healthcare professionals, such as physicians, may use to track their patients' progress in a healthcare facility, such as a hospital, and seamlessly hand over patient care to their colleagues. The census GUI platform may be configured to apply a highly intuitive user interface and real time analytics to support and enhance networks of communication and collaboration between teams in high intensity, multidisciplinary health systems.

As shown in FIG. 23A, a GUI may include a navigation object 2305 having a primary navigation level 2325. Selection of a census selection area 2345 may cause a patient information object 2365 to be presented on the GUI. In some embodiments, the patient information object 2365 may be configured as a patient list, such as a list of patients in a healthcare facility, a department (for instance, an emergency room), affiliated with a particular healthcare professional, combinations thereof, or the like. The patient information object 2365 may include various information elements, including, without limitation, an area where the patient is located 2375a (for instance, the emergency room, the operating room, a particular room, or the like), a patient identifier 2375b, and other patient information 2375c.

Figure 23B:
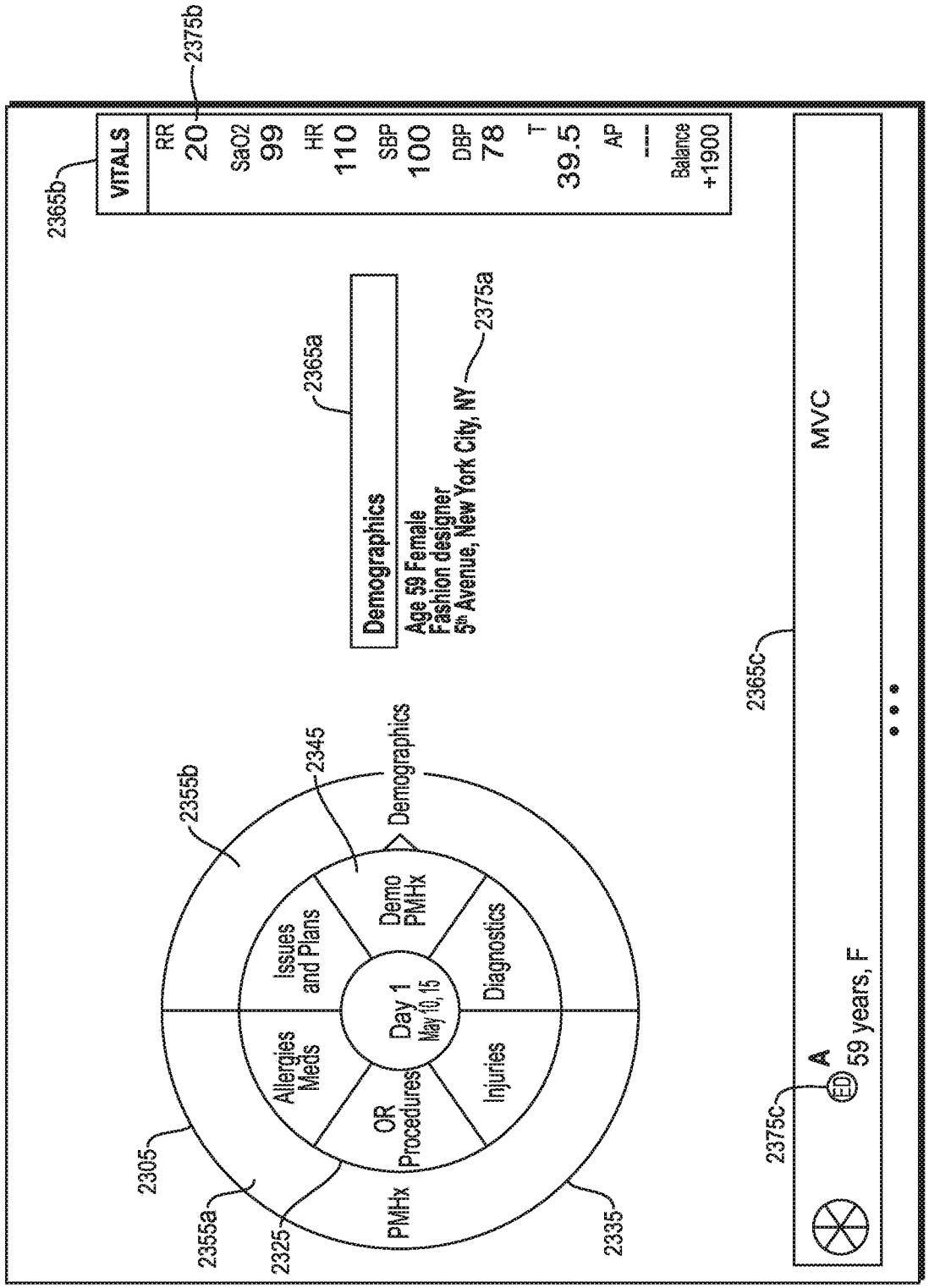
Figure 23C:
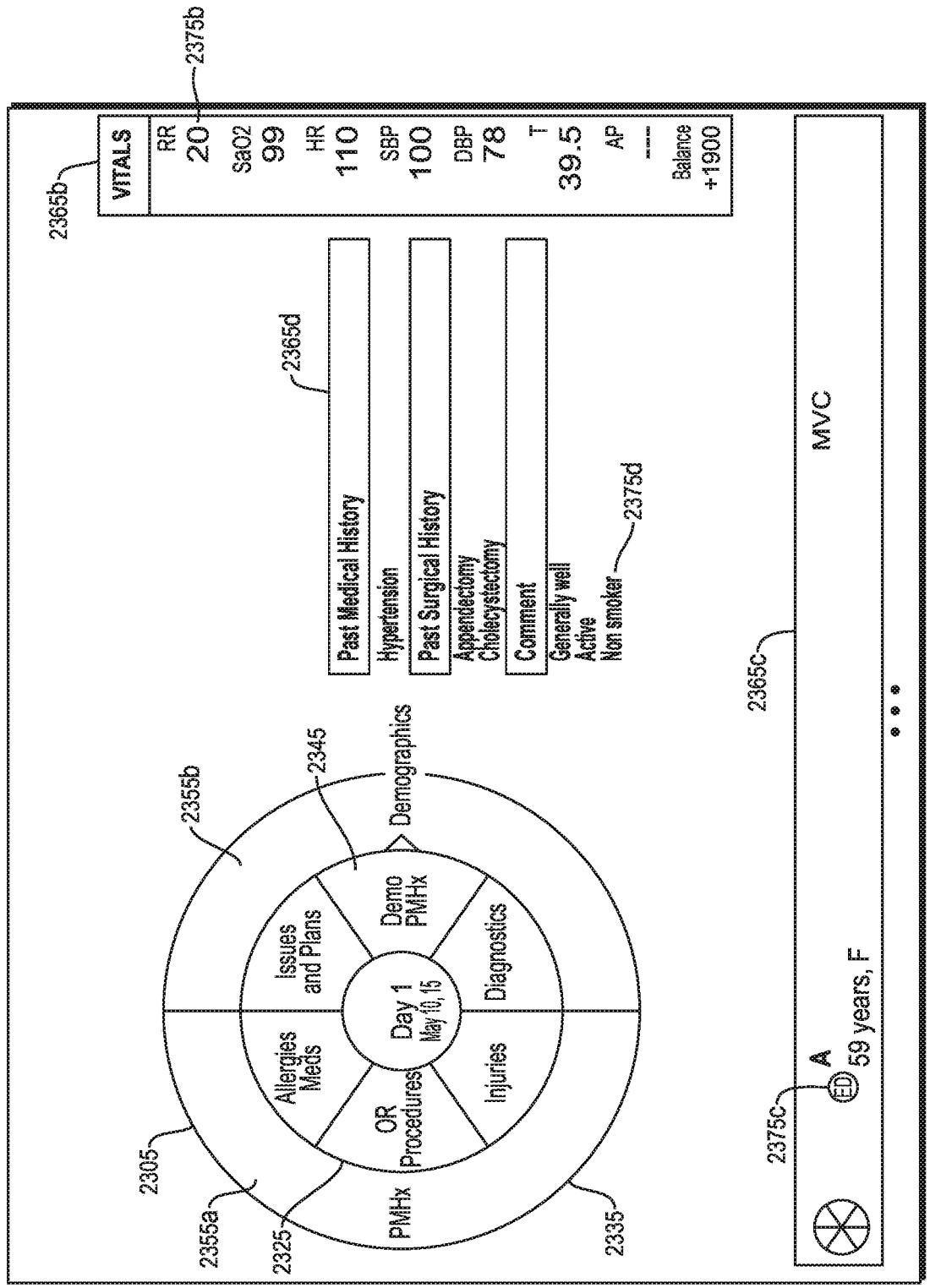

In some embodiments, selection of a patient information element 2375b may cause the presentation of an illustrative census GUI platform interface according to some embodiments as depicted in FIG. 23B, for example, configured to allow for access and control of information related to the patient. The GUI may include a navigation object 2305 that includes a primary navigation level 2325 and a secondary navigation level 2335. Selection of a demographics/patient history selection area 2345 may cause a patient medical history selection area 2355a and a demographics selection area 2355b to be presented on the secondary navigation level 2335. Selection of the demographics selection area 2355a may cause a demographics information object 2365 to be presented along with various demographics information elements 2375a. In addition, the GUI depicted in FIG. 23B may include a vitals information object 2365b with corresponding vitals information elements 2376b and a patient data information object 2365c along with corresponding patient data information elements 2375c. As shown in FIG. 23C, selection of the patient medical history selection area 2355a may cause a medical history information object 2365d with corresponding medical history information elements 2375d to be displayed on the GUI.

Figure 23D:
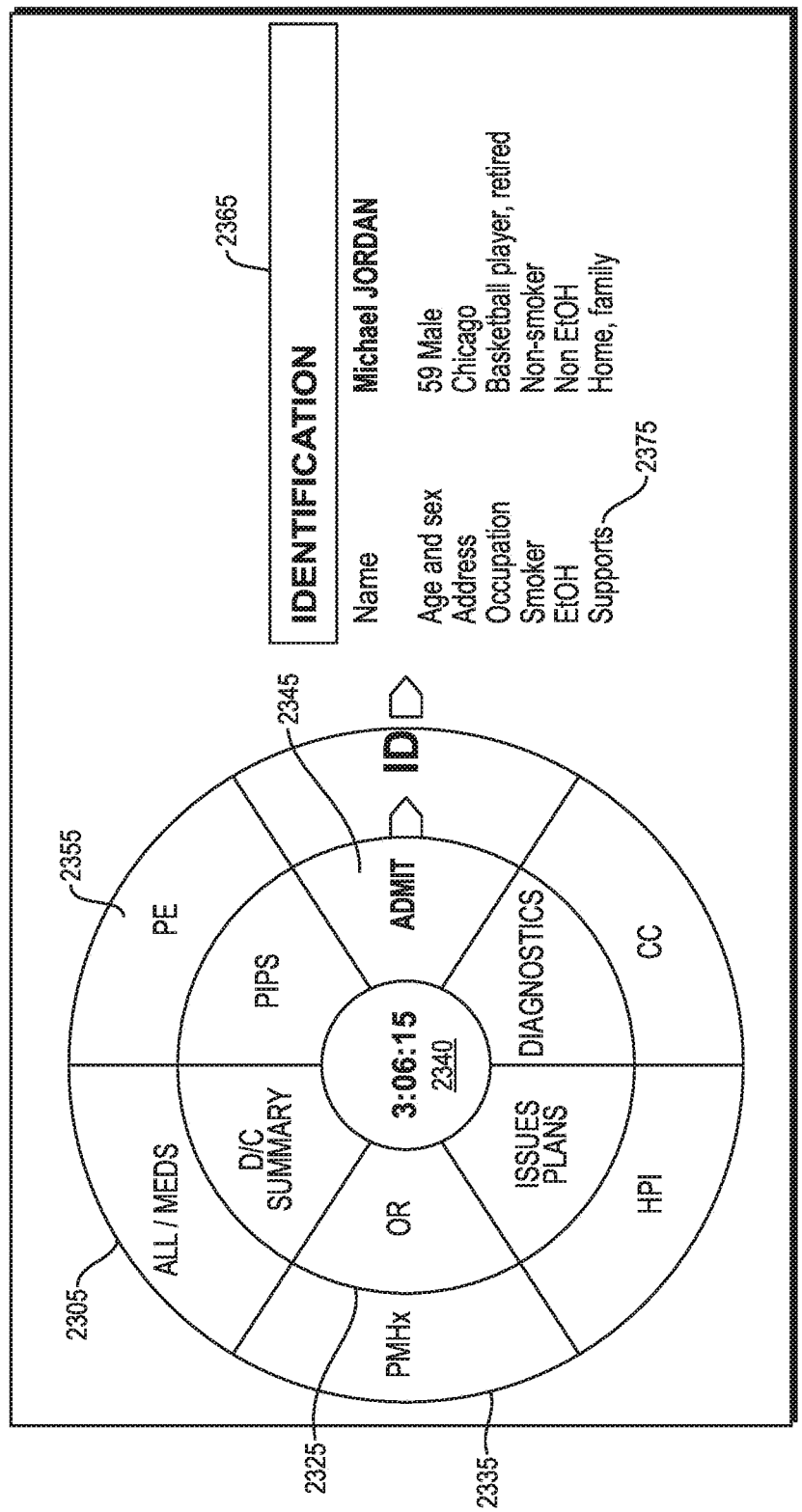
Figure 23E:
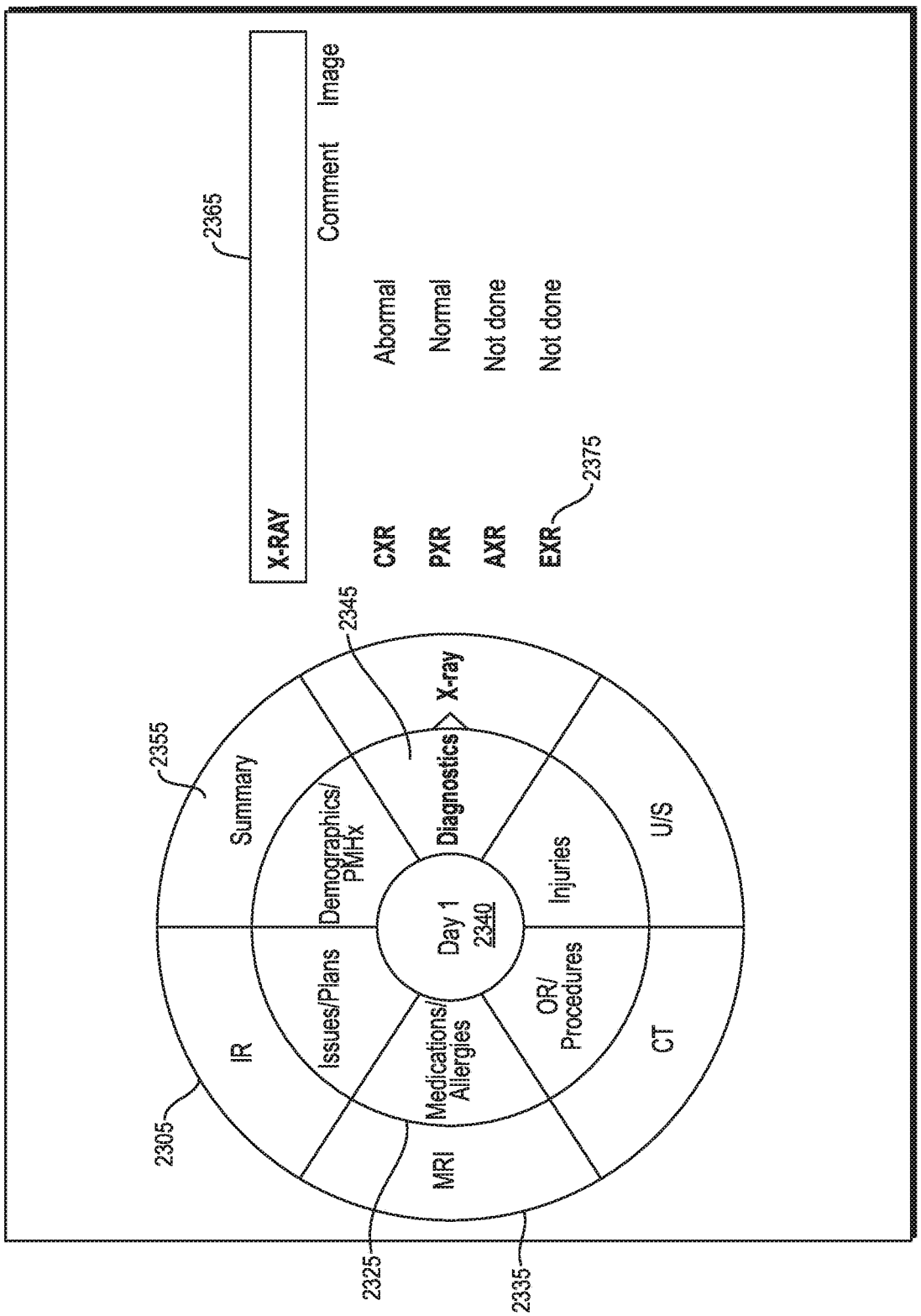

As shown in FIG. 23D, selection of the add (or admit) patient selection area 2345 depicted in FIG. 23A may cause an add patient GUI to be presented on a display element of a client computing device. In some embodiments, adding a patient may generate a new patient record. As shown in FIG. 23D, a timer 2340 may be depicted, for instance, on the navigation object 2305. In some embodiments, the timer 2340 may be configured to indicate the time elapsed since a particular event, such as a trauma to a patient, admission, countdown to surgery, or the like. In some embodiments, the duration and/or time scale of the timer 2340 may be determined based on the active selection area 2345 and/or 2355. In some embodiments, the timer 2340 may be based on phases, for instance, of a process. In some embodiments, the scale of the timer 2340 may be seconds, minutes, days, or some combination thereof. FIG. 23E depicts a screen presented responsive to selection of the diagnostics selection area 2345, for example, as depicted in FIG. 23B. As shown in FIG. 23E, selection areas 2355 may be presented on the secondary navigation level for various types of diagnostic tests. Selection of a diagnostic test selection area 2355 may cause a diagnostic test information object 2365 and corresponding information elements 2375 to be presented on the screen.

Figure 24:
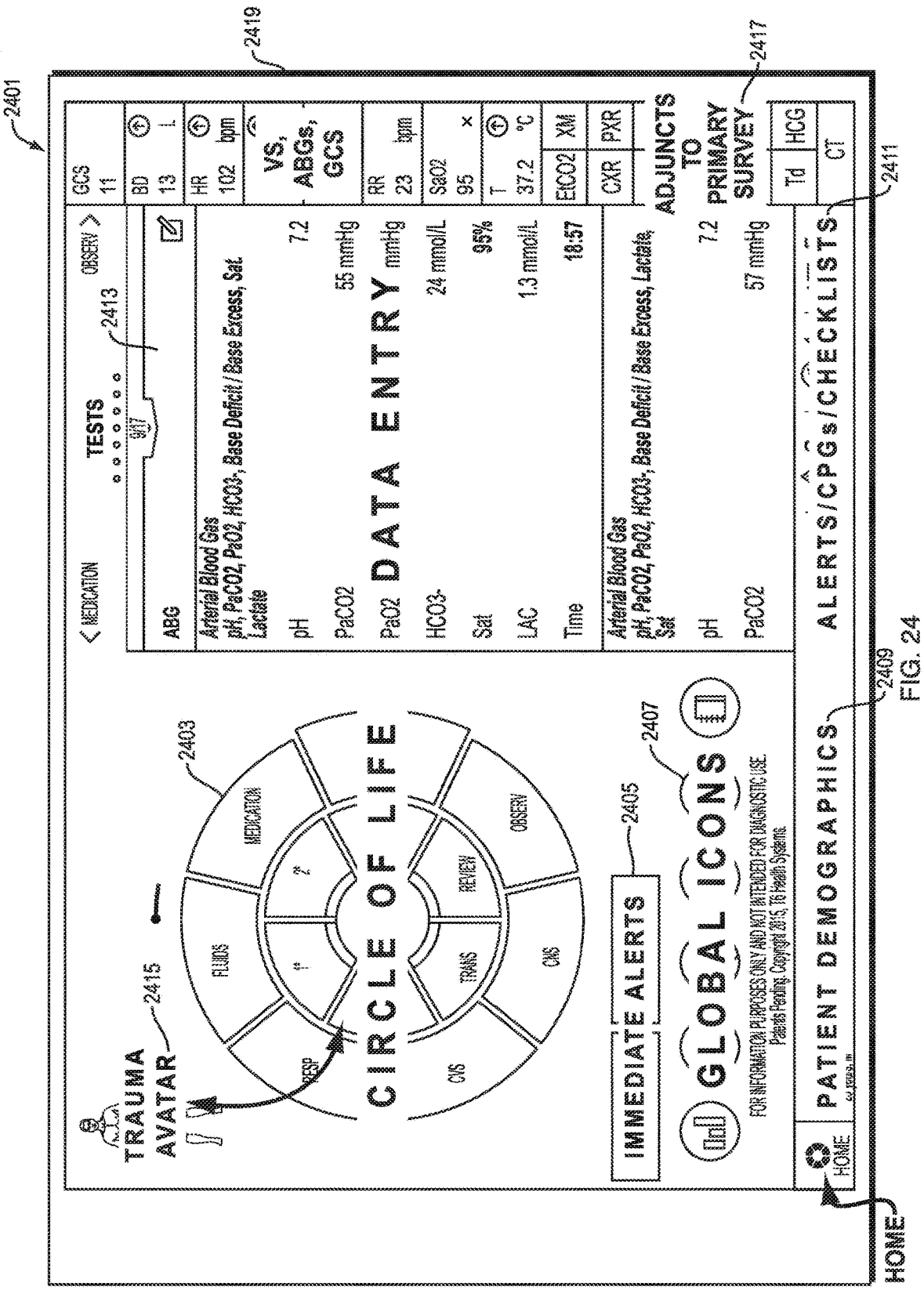
FIG. 24 depicts an illustrative screen template according to some embodiments.

FIG. 24 depicts an illustrative screen template according to some embodiments. Screens and GUI objects presented via the system according to some embodiments may be generated according to the template screen 2401 depicted in FIG. 24. For example, a screen may include a navigation object 2403 configured according to some embodiments, such as the "circle of life" configuration. The "circle of life" configuration, for example, in a trauma situation, provides a technological advantage as it corresponds to the clock-like progression or flow through the patient treatment process. A patient graphical representation (or "trauma man," "trauma avatar," or the like) object 2415 may be presented on the screen. In some embodiments, selection of the patient graphical representation object 2415 may cause a screen, such as the screen 1501 depicted in FIG. 15E, to be presented to a user with the patient representation 1507 GUI object. A section of the screen 2401 may include immediate alerts 2405 relating to the patient. In some embodiments, the immediate alerts 2405 may include key patient indicators, such as key patient indicators 1805a-n depicted in FIG. 18A. A portion of the screen 2401 may include patient demographic information objects 2409 with corresponding patient demographic information elements for a subject patient. The screen 2401 may also include an alerts, clinical practice guidelines, and checklists area 2411, a data entry/data access area 2413, an adjuncts to primary survey area 2417, and a vitals, Arterial Blood Gas (ABG), Glasgow Coma Scale (GCS) area 2419 configured according to some embodiments.

Figure 15F:
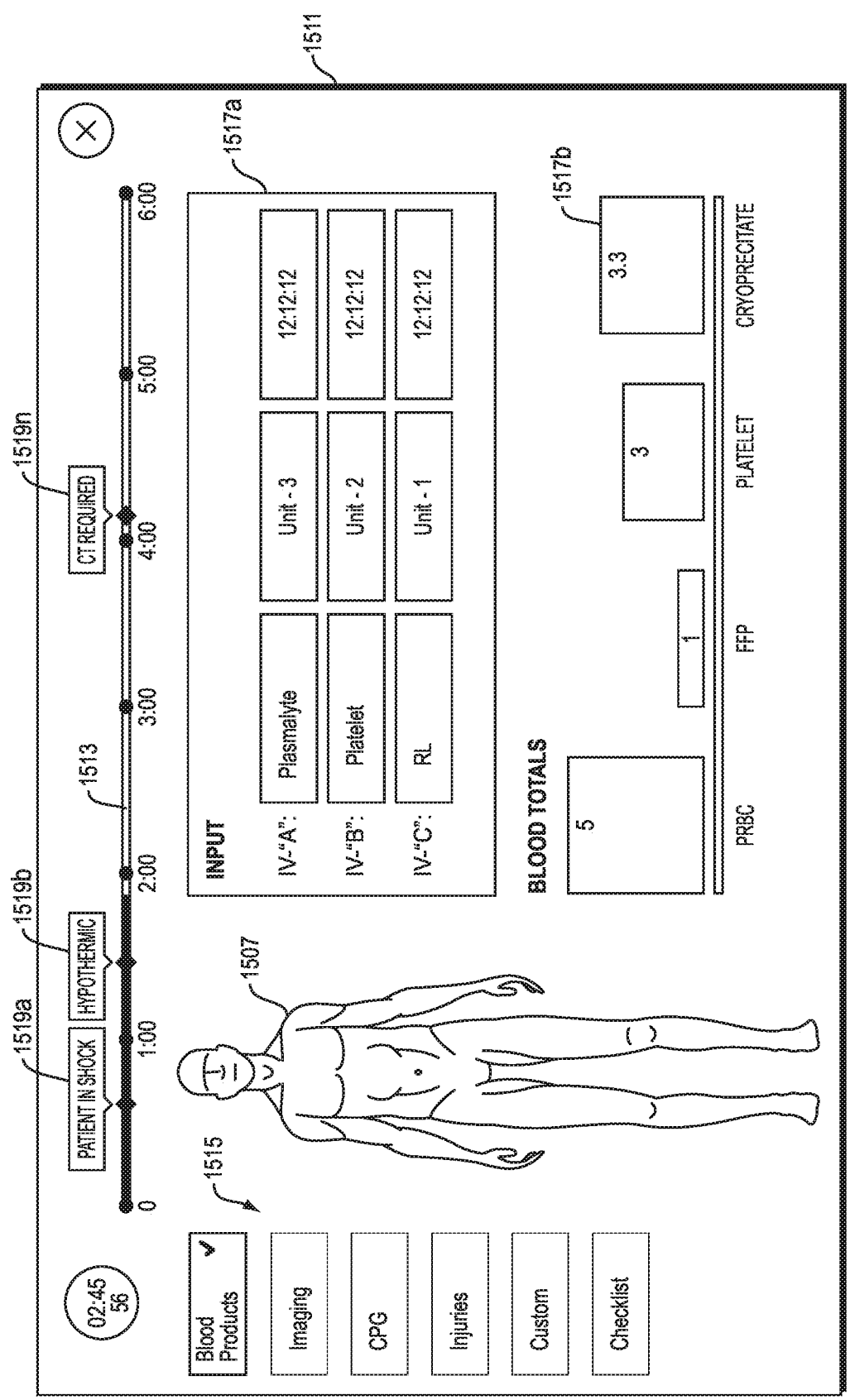

FIG. 15F depicts an illustrative patient information screen according to some embodiments. The patient information screen 1511 may be configured to present various patient conditions, such as a shock condition (for instance, a "shock dashboard"). The patient information screen may include selection objects 1515, selection of which may cause associated information objects 1517a, 1517b to be displayed on the patient information screen. In some embodiments, the patient information screen 1511 may include a timeline information object 1513 that may be configured to present a timeline of patient activity, as well as certain events or conditions 1519a-n that have occurred.

FIG. 25 depicts illustrative and non-restrictive technological advantages resulting from use of the system configured according to some embodiments.

Figure 26:
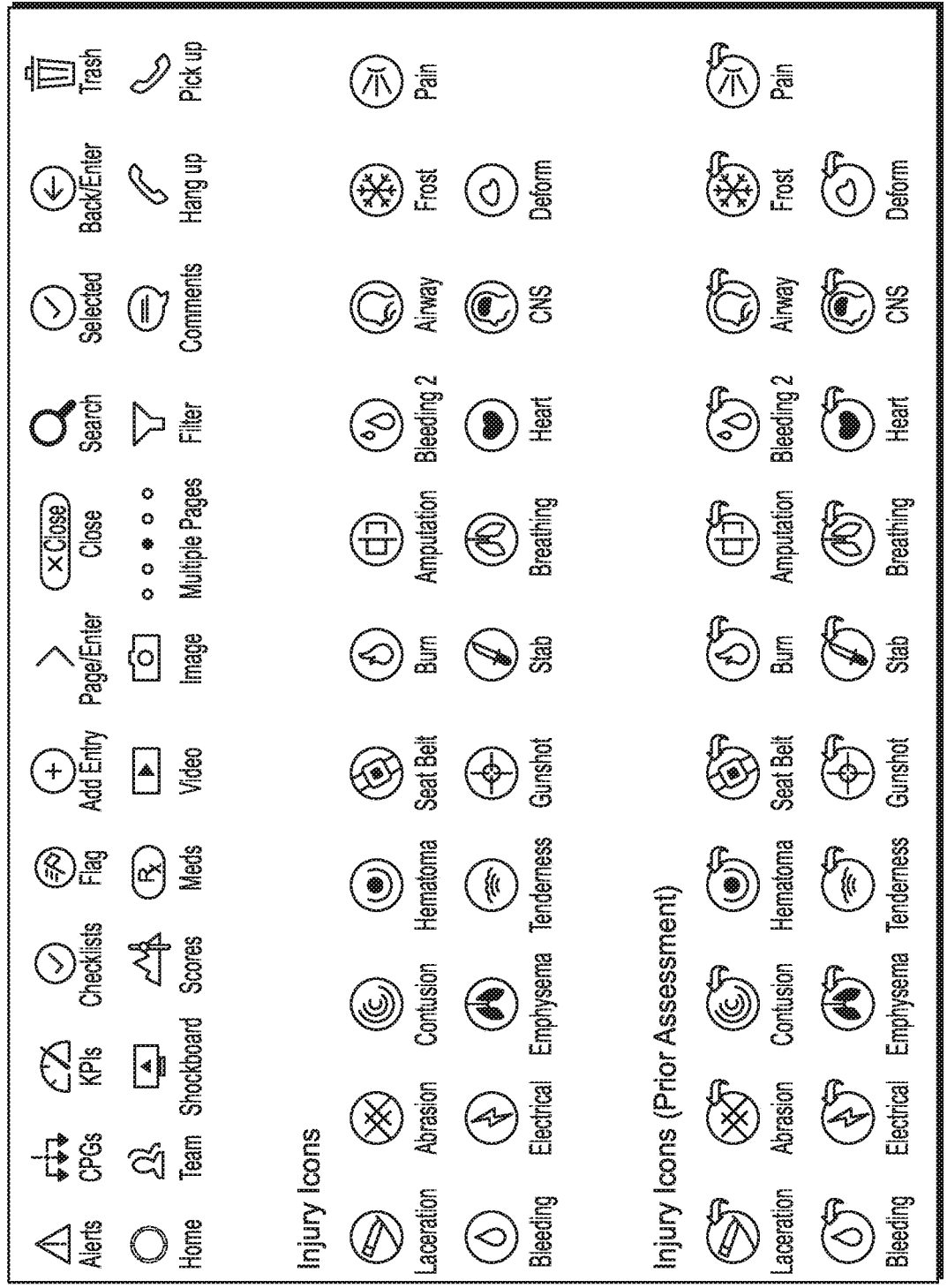
FIG. 26 depicts various symbols and icons that may be used within the healthcare information application to represent information and objects.

FIG. 26 depicts various symbols and icons that may be used within the healthcare information application to represent information, such as navigation objects, injury icons, or the like. In some embodiments, a user may select an icon for placement on a screen and/or a portion thereof, such as the patient representation 1507 to indicate the location and type of injury.

Figure 27:
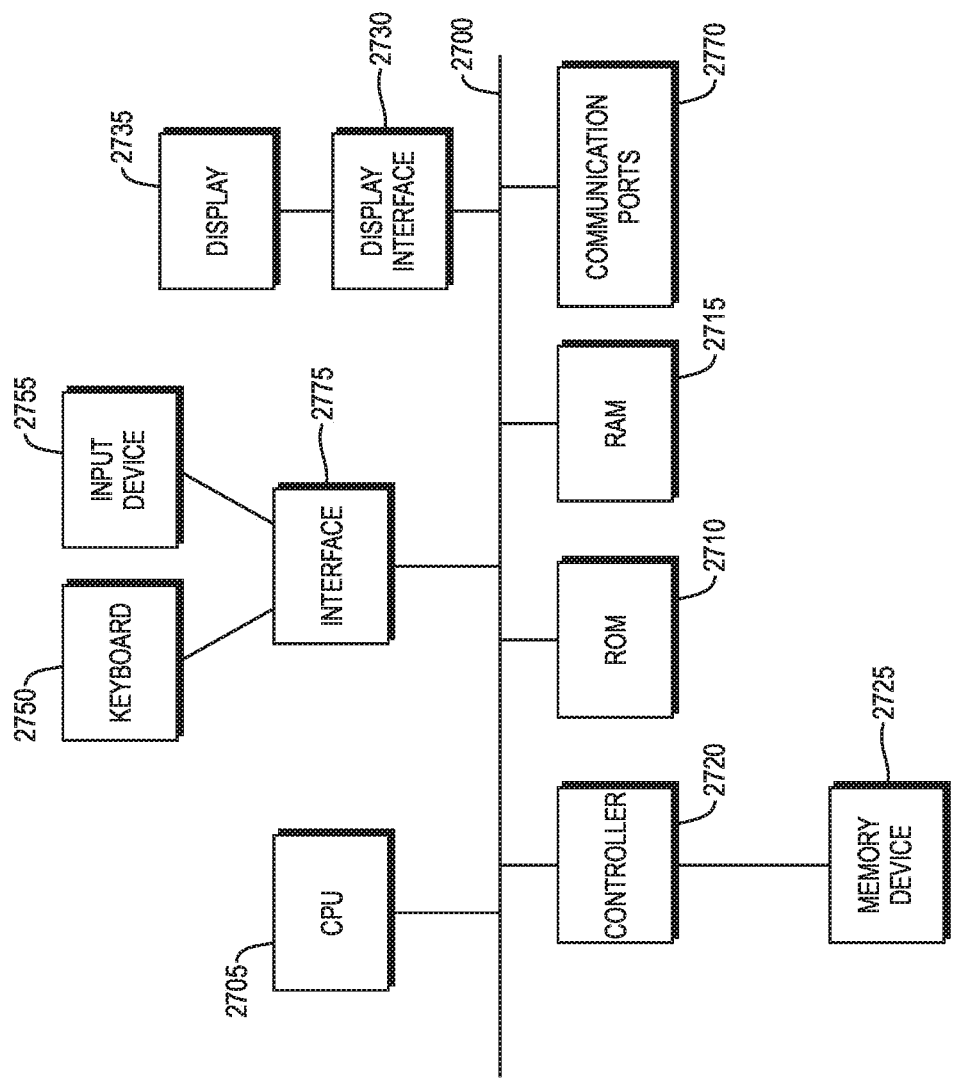
FIG. 27 illustrates various embodiments of a computing device for implementing the various methods and processes described herein.

FIG. 27 depicts a block diagram of exemplary internal hardware that may be used to contain or implement the various computer processes and systems as discussed above. A bus 2700 serves as the main information highway interconnecting the other illustrated components of the hardware. CPU 2705 is the central processing unit of the system, performing calculations and logic operations required to execute a program. CPU 2705 is an exemplary processing device, computing device or processor as such terms are used within this disclosure. Read only memory (ROM) 2730 and random access memory (RAM) 2735 constitute exemplary memory devices.

A controller 2720 interfaces with one or more optional memory devices 2725 to the system bus 2700. These memory devices 2725 may include, for example, an external or internal DVD drive, a CD ROM drive, a hard drive, flash memory, a USB drive or the like. As indicated previously, these various drives and controllers are optional devices. Additionally, the memory devices 2725 may be configured to include individual files for storing any software modules or instructions, auxiliary data, common files for storing groups of results or auxiliary, or one or more databases for storing the result information, auxiliary data, and related information as discussed above. For example, the memory devices 2725 may be configured to store healthcare information 325, healthcare analysis processes 330 and/or data contained in the data stores 115.

Program instructions, software or interactive modules for performing any of the functional steps associated with the analysis and presentation of healthcare information as described above may be stored in the ROM (read only memory) 2730 and/or the RAM (random access memory) 2735. Optionally, the program instructions may be stored on a tangible computer-readable medium such as a compact disk, a digital disk, flash memory, a memory card, a USB drive, an optical disc storage medium, such as a Blu-ray™ disc, and/or other recording medium.

An optional display interface 2730 may permit information from the bus 2700 to be displayed on the display 2735 in audio, visual, graphic or alphanumeric format. The information may include information related to a current job ticket and associated tasks. Communication with external devices may occur using various communication ports 2740. An exemplary communication port 2740 may be attached to a communications network, such as the Internet or a local area network.

The hardware may also include an interface 2745 which allows for receipt of data from input devices such as a keyboard 2750 or other input device 2755 such as a mouse, a joystick, a touch screen, a remote control, a pointing device, a video input device and/or an audio input device.

Computer program logic implementing all or part of the functionality previously described herein may be embodied in various forms, including, but in no way limited to, a source code form, a computer executable form, and various intermediate forms (for example, forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in a non-transitory form (for example, a source code form, a computer executable form, an intermediate form, or combinations thereof) in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by some embodiments described herein.

What is claimed is:

1. A healthcare information analysis and presentation system comprising: a processor; and a non-transitory, computer-readable storage medium in operable communication with the processor, wherein the computer-readable storage medium contains one or more programming instructions that, when executed, cause the processor to: receive point-of-care healthcare information associated with a patient in substantially real-time collected via at least one of a plurality of mobile computing devices; analyze the healthcare information to generate a patient profile of the patient, the patient profile comprising a physiological status, a physiological assessment, and a treatment assessment; store the patient profile in a centralized storage; generate at least one interactive graphical user interface element associated with the patient profile for presentation at a plurality of display devices associated with healthcare professionals involved with care of the patient, wherein the at least one interactive graphical user interface element allows the healthcare professionals to access physiological status, physiological assessment, and/or treatment assessment information from the patient profile via the centralized storage and to provide documentation information and communication information for consumption by at least one other healthcare professional regarding the care of the patient; update the patient profile in the centralized storage with the provided documentation and communication information to thereby provide selective access to the provided documentation and communication information from the patient profile via the centralized storage; and automatically update information displayed on at least one display device of a healthcare professional in substantially real-time based on the updated patient profile to provide up-to-date and dynamic information to the healthcare professional, wherein the updated information displayed on the at least one display device includes a graphical representation of a body of the patient and further includes at least one interactive icon depicted on each of a number of body parts for which information is available from the centralized storage, wherein each interactive icon includes a graphical representation of a type of injury associated with the body part and is selectively included in the information displayed on the at least one display device corresponding to a severity of the injury to the patient individually.

2. The system of claim 1, wherein the plurality of display devices comprise a monitor device.

3. The system of claim 1, wherein the healthcare information comprises at least one of surgeries, symptoms, type of injury, severity of injury, mechanism of trauma, and trauma location.

4. The system of claim 1, wherein the system is configured to be used for trauma healthcare services.

5. The system of claim 1, wherein the system is configured to be used for surgical healthcare services.

6. The system of claim 1, wherein the plurality of mobile computing devices comprise a smartphone and a tablet computing device.

7. The system of claim 1, wherein the healthcare information comprises user input and device input.

8. The system of claim 1, wherein the graphical user interface element comprises a dashboard.

9. The system of claim 8, wherein the dashboard is configured to receive health information user input through at least one field.

10. A computer-implemented method for analyzing and presenting health information, the method comprising, by a processor: receiving point-of-care healthcare information associated with a patient in substantially real-time collected via at least one of a plurality of mobile computing devices; analyzing the healthcare information to generate a patient profile of the patient, the patient profile comprising a physiological status, a physiological assessment, and a treatment assessment; storing the patient profile in a centralized storage; generating at least one interactive graphical user interface element associated with the patient profile for presentation at a plurality of display devices associated with healthcare professionals involved with care of the patient, wherein the at least one interactive graphical user interface element allows the healthcare professionals to access physiological status, physiological assessment, and/or treatment assessment information from the patient profile via the centralized storage and to provide documentation information and communication information for consumption by at least one other healthcare professional regarding the care of the patient; updating the patient profile in the centralized storage with the provided documentation and communication information to thereby provide selective access to the provided documentation and communication information from the patient profile via the centralized storage; and automatically updating information displayed on at least one display device of a healthcare professional in substantially real-time based on the updated patient profile to provide up-to-date and dynamic information to the healthcare professional, wherein the updated information displayed on the at least one display device includes a graphical representation of a body of the patient and further includes at least one interactive icon depicted on each of a number of body parts for which information is available from the centralized storage, wherein each interactive icon includes a graphical representation of a type of injury associated with the body part and is selectively included in the information displayed on the at least one display device corresponding to a severity of the injury to the patient individually.

11. The method of claim 10, wherein the plurality of display devices comprise a monitor device.

12. The method of claim 10, wherein the healthcare information comprises at least one of surgeries, symptoms, type of injury, severity of injury, mechanism of trauma, and trauma location.

13. The method of claim 10, wherein the method is configured to be performed for trauma healthcare services.

14. The method of claim 10, wherein the system is configured to be used for surgical healthcare services.

15. The method of claim 10, wherein the plurality of mobile computing devices comprise a smartphone and a tablet computing device.

16. The method of claim 10, wherein the healthcare information comprises user input and device input.

17. The method of claim 10, wherein the graphical user interface element comprises a dashboard.

18. The method of claim 17, wherein the dashboard is configured to receive health information user input through at least one field.

* * * * *